US012774449B2

(12) United States Patent
Haremaki et al.

(10) Patent No.: US 12,774,449 B2
(45) Date of Patent: Oct. 27, 2026

(54) SELF-ORGANIZING NEURAL ECTODERMAL LINEAGE CELLULAR STRUCTURES, AND COMPOSITIONS AND METHODS RELATING THERETO

(71) Applicant: THE ROCKEFELLER UNIVERSITY, New York, NY (US)

(72) Inventors: Tomomi Haremaki, New York, NY (US); Jakob Metzger, New York, NY (US); Fred Etoc, New York, NY (US); Ali Brivanlou, New York, NY (US)

(73) Assignee: THE ROCKEFELLER UNIVERSITY, New York, NY (US)

( * ) Notice: Subject to any disclaimer, the term of this patent is extended or adjusted under 35 U.S.C. 154(b) by 1194 days.

(21) Appl. No.: 17/621,328

(22) PCT Filed: Jun. 22, 2020

(86) PCT No.: PCT/US2020/038912

§ 371 (c)(1),
(2) Date: Dec. 21, 2021

(87) PCT Pub. No.: WO2020/257756

PCT Pub. Date: Dec. 24, 2020

(65) Prior Publication Data

US 2022/0403332 A1 Dec. 22, 2022

Related U.S. Application Data

(60) Provisional application No. 62/864,881, filed on Jun. 21, 2019.

(51) Int. Cl.
*C12N 5/0797* (2010.01)
*C12Q 1/02* (2006.01)

(52) U.S. Cl.
CPC .......... *C12N 5/0623* (2013.01); *C12Q 1/025* (2013.01); *C12N 2501/15* (2013.01); *C12N 2501/155* (2013.01); *C12Q 2600/112* (2013.01)

(58) Field of Classification Search
CPC .............................. C12N 5/0623; C12Q 1/025
IPC .............................. C12N 5/0623; C12Q 1/025
See application file for complete search history.

(56) References Cited

FOREIGN PATENT DOCUMENTS

| | | |
|---|---|---|
| WO | 2010096496 A2 | 8/2010 |
| WO | 2017147536 A1 | 8/2017 |

OTHER PUBLICATIONS

Wu et al. SNW1 Is a Critical Regulator of Spatial BMP Activity, Neural Plate Border Formation, and Neural Crest Specification in Vertebrate EmbryosPLoS Biol. Feb. 15, 2011;9(2):e1000593. (Year: 2011).*

"Disk-shaped." Merriam-Webster.com Dictionary, Merriam-Webster, https://www.merriam-webster.com/dictionary/disk-shaped. Accessed Apr. 17, 2025. (Year: 2025).*

George Britton, Idse Heemskerk, Rachel Hodge, Amina A Qutub, Aryeh Warmflash. A novel self-organizing embryonic stem cell system reveals signaling logic underlying the patterning of human ectoderm. Jan. 11, 2019. BioRxiv. (Year: 2019).*

CYTOOplates Motility User Manual (2014). (Year: 2014).*

Attisano, L. and Tuen Lee-Hoeflich, S., 2001. The smads. Genome biology, 2(8), pp. 3010-3011. (Year: 2001).*

Bragdon, B., Moseychuk, O., Saldanha, S., King, D., Julian, J. and Nohe, A., 2011. Bone morphogenetic proteins: a critical review. Cellular signalling, 23(4), pp. 609-620. (Year: 2011).*

Xue, X., Sun, Y., Resto-Irizarry, A.M., Yuan, Y., Aw Yong, K.M., Zheng, Y., Weng, S., Shao, Y., Chai, Y., Studer, L. and Fu, J., 2018. Mechanics-guided embryonic patterning of neuroectoderm tissue from human pluripotent stem cells. Nature materials, 17(7), pp. 633-641. (Year: 2018).*

Xue, X., Sun, Y., Resto-Irizarry, A.M., Yuan, Y., Aw Yong, K.M., Zheng, Y., Weng, S., Shao, Y., Chai, Y., Studer, L. and Fu, J., 2018. Mechanics-guided embryonic patterning of neuroectoderm tissue from human pluripotent stem cells. Nature materials, 17(7), Supplementary Materials. (Year: 2018).*

Zakrzewski, W., Dobrzyński, M., Szymonowicz, M. and Rybak, Z., 2019. Stem cells: past, present, and future. Stem cell research & therapy, 10(1), p. 68. (Year: 2019).*

CYTOOchips product website. Accessed from the Internet Oct. 14, 2025. <https://cytoo.com/our-products/cytoochips/> (Year: 2025).*

Chambers Stuart M et al, "Dual-SMAD Inhibition/WNT Activation-Based Methods to Induce Neural Crest and Derivatives from Human Pluripotent Stem Cells", Methods in Molecular Biology, 2016, vol. 1307, pp. 329-343.

S. Reichert et al, "A BMP regulatory network controls ectodermal cell fate decisions at the neural plate border", Development, 2013, vol. 140, No. 21, pp. 4435-4444.

(Continued)

*Primary Examiner* — Kara D Johnson
*Assistant Examiner* — Risa Takenaka
(74) *Attorney, Agent, or Firm* — Hoffmann & Baron LLP

(57) ABSTRACT

The present disclosure relates to a neural ectodermal lineage cellular structure, and compositions and methods related thereto. In some embodiments, the disclosure provides a geometrically isolated neural ectodermal lineage cellular structure (neuruloid) including spatially segregated neuroepithelial cells, sensory placodes, neural crest cells, and epidermal cells having radial organization around a lumen within the neuroepithelial cells. The disclosure also provides methods directed to forming the neural ectodermal lineage cellular structure. The disclosure also provides methods and platforms directed to the neural ectodermal lineage cellular structure.

17 Claims, 51 Drawing Sheets
(49 of 51 Drawing Sheet(s) Filed in Color)
Specification includes a Sequence Listing.

(56) References Cited

OTHER PUBLICATIONS

Alessia Deglincerti et al, "Self-Organization of Spatial Patterning in Human Embryonic Stem Cells", Current Topics in Developmental Biology, 2016, vol. 116, pp. 99-113.
Wilson PA et al, "Concentration-dependent patterning of the Xenopus ectoderm by BMP4 and its signal transducer Smad1", Development, 1997, vol. 124, No. 16, pp. 3177-3184.

* cited by examiner

G

CS12 days 26 - 30

J

F

B

F

G

G

A

C

H

A

Neuruloid, day7

| | RUES2 | 56CAG |
|---|---|---|
| # cells | 2,626 | 4,024 |
| # cells after QC | 2,591 | 4,005 |
| mean aligned reads/ cell | 67,640 | 45,403 |
| median UMIs/ cell | 18,369 | 10,548 |
| mean genes/ cell | 3,568 | 2,911 |

B

B

C

SELF-ORGANIZING NEURAL ECTODERMAL LINEAGE CELLULAR STRUCTURES, AND COMPOSITIONS AND METHODS RELATING THERETO

CROSS REFERENCE TO RELATED APPLICATIONS

The present application is a national stage application which claims priority from PCT Application No. PCT/US2020/038912 filed Jun. 22, 2020, which in turn claims priority from U.S. Provisional Application Ser. No. 62/864,881 filed Jun. 21, 2019. Applicant claims the benefits of 35 U.S.C. § 120 as to the PCT application and priority under 35 U.S.C. § 119 as to the said U.S. Provisional application, and the entire disclosures of all applications are incorporated herein by reference in their entireties.

SEOUENCE LISTING

The instant application contains a Sequence Listing, conforming to the rules of 37 CFR 1.821-1.825, submitted in ASCII text file format which is hereby incorporated by reference in its entirety. Said ASCII text format Sequence Listing, created on Jun. 22, 2020, is named 1119-59_PCT-Sequence Listing and is 8,100 bytes in size.

FIELD OF THE INVENTION

The present disclosure relates generally to a neural ectodermal lineage cellular structure, and compositions and methods related thereto. The disclosure provides a geometrically isolated neural ectodermal lineage cellular structure (neuruloid) including spatially segregated neuroepithelial cells, sensory placodes, neural crest cells, and epidermal cells having radial organization around a lumen within the neuroepithelial cells and methods directed to forming the neural ectodennal lineage cellular structure. The disclosure also provides methods and platforms directed to the neural ectodermal lineage cellular structure.

BACKGROUND

Neurulation is a key developmental transition which encompasses a series of highly orchestrated events giving rise to the formation of different ectodermal derivatives: neural progenitors, neural crest, sensory placodes, and epidermis (Ozair, M. Z., Kintner, C. & Brivanlou, A. H. (2013) Developmental biology 2:479-498) The emergence of these discrete fates occurs concomitantly with complex morphogenetic processes, leading to neural tube closure and spatial segregation of the four populations. Neurulation events, originally characterized in amphibians, are evolutionarily conserved (Chambers, S. M. et al. (2009) Nature biotechnology 27, 275-280; Ozair, M. Z. et al (2013) Stem cells 31:35-47) and have now been emulated to guide human Embryonic Stem Cells (hESCs) differentiation towards separate ectodermal lineages in vitro (Dincer, Z. et al. (2103) Cell reports 5:1387-1402; Tchieu, J. et al. (2017) Cell stem cell 21, 399-410 e397).

Inhibition of on-going TGFβ signalling induces the anterior neural plate by default neural induction (1-emmati-Brivanlou, A. & Melton, D. A. (1994) Cell 77:273-281; Munoz-Sanjuan, I. & Brivanlou, A. 1H. (2002) Nature reviews. Neuroscience 3:271-280). BMP4 signalling at the edge of the ectodermal domain acts as a morphogen to induce and pattern the medio-lateral aspects of the neural plate, with high signaling specifying epidermis, no signaling leading to neural fate, and intermediate levels generating neural crests and sensory placodes (Ozair, M. Z., Kintner, C. & Brivanlou, A. H. (2013) Developmental biology 2:479-498; Wilson, P. A., Lagna, G., Suzuki, A. & Hemrnati-Brivanlou, A. (1997) Development 124:3177-3184). Additionally, WN[1]T and FGF signalling have been linked to placode and neural crest specification in a range of model systems (Bhattacharyya, S. & Bronner-Fraser, M. (2004) Curr Opin Genet Dev 14:520-526; Litsiou, A., Hanson, S. & Streit, A. (2005) Development 132:4051-4062; Sauka-Spengler, T. & Bronner-Fraser, M. (2008) Nature reviews. Molecular cell biology 9:557-568; Betancur, P., Bronner-Fraser, M. & Sauka-Spengler, T. (2010) Proc Natl Acad Sci USA 107:3570-3575; Kwon, H. J., Bhat, N., Sweet, E. M., Cornell, R. A. & Riley, B. B. (2010) PLoS genetics 6:e1001133, doi:10.1371/journal.pgen.1001133; Schlosser, G. (2014) Developmental biology 3: 349-363). Together, these three major pathways orchestrate neurulation (Wilson, P. A., Lagna, G., Suzuki, A. & Hemmati-Brivanlou, A. (1997) Development 124:3177-3184; Stuhimiller, T. J. & Garcia-Castro, M. 1. (2012) Development 139:289-300; Reichert, S., Randall, R. A. & Hill, C. S. (2103) Development 140:4435-4444; Patthey, C. & Gunhaga, L. (2014) Experimental cell research 321:11-16; Leung, A. W. et al. (2016) Development 143:398-410). However, how their respective signaling activities are integrated in space and time to control both patterning and morphogenesis is unknown, especially in humans.

Many human genetic diseases that target the ectodermal compartment (such as Down's syndrome, DiGeorge's syndrome, and LEOPARD syndromes) are commonly accompanied by defects in multiple ectodermal compartments (Greenberg, F. (1993) Journal of medical genetics 30:803-806; Roizen, N. J. & Patterson, D. (2003) Lancet 361:1281-1289; Sarkozy, A., Digilio, M. C. & Dallapiccola, B. (2008) Orphanet journal of rare diseases 3:13). Likewise, pediatric cancers (such as neurofibromatosis) often affect multiple ectodermal derivatives, as do neural tube defects (Ferner, R. E. (2007) European journal of human genetics:EJHG 15:131-138; Greene, N. D. & Copp, A. J. (2014) Annual review of neuroscience 37:221-242). These conditions remain poorly understood, mostly because they have been studied in specific cell types rather than their global tissue context, in the presence of interactions between multiple ectodermal lineages.

Therefore, there remains a need for a tractable model of human neurulation as well as early human neural development disorders.

SUMMARY OF THE INVENTION

The invention relates to a neural ectodermal lineage cellular structure, and compositions and methods related thereto.

In one aspect, the invention provides methods of forming a neural ectodermal lineage cellular structure ("neuruloid"). The methods typically include the steps of: (a) culturing mammalian stem cells seeded on a circular micropattern substrate under conditions of dual SMAD inhibition such that a colony comprising a lumen is formed; and (b) culturing the colony in the presence of a bone morphogenetic protein (BMP) under conditions under which neurulation occurs, thereby forming a neural ectodermal lineage cellular structure. Exemplary methods of forming neuruloids are further described in the Detailed Description and numbered embodiments 1 to 150, infra.

In one aspect, the invention provides neuruloids formed from mammalian cells on a circular micropattern substrate. Such neuruloids generally include spatially segregated neuroepithelial cells, sensory placodes, neural crest cells, and epidermal cells, and whose cells display radial organization around a lumen within the neuroepithelial cells. Exemplary methods of forming neuruloids are further described in the Detailed Description and numbered embodiments 151 to 174, infra.

The present invention further provides methods of screening for agents that modify neuruloid phenotypes in order to identify active agents. In some embodiments, the screening is performed to identify a candidate therapeutic to determine whether exposure of a cell culture to a test agent during, before and/or after neuruloid formation reverses a disease phenotype in the neuruloid. In other embodiments, the screening is performed to determine whether exposure of a cell culture to a test agent during, before and/or after neuruloid formation results in an abnormal phenotype, for example to identify whether a substance is a teratogen. In various embodiments, the culture is exposed to a test agent for at least 1 day, at least 2 days, or at least 3 days during neuruloid formation, and up to the entire period of neuruloid formation.

Thus, in one aspect, the invention provides methods of determining whether a test agent is biologically active against a disease phenotype.

The methods can include (a) culturing a first mammalian stem cell population under conditions that in the absence of the test agent result in the formation of a first neuruloid that exhibits a disease phenotype, (b) exposing the culture of step (a) to the test agent, and (c) determining whether the test agent partially or wholly reverses a disease phenotype associated with a second neuruloid obtained from a second mammalian stem cell population cultured under the same conditions as the first mammalian stem cell population but not exposed to the test agent, thereby determining whether the test agent is biologically active against the disease phenotype. Exemplary methods of determining whether a test agent is biologically active against a disease phenotype are further described in the Detailed Description and numbered embodiments 175 to 191, infia.

In another aspect, the invention provides methods of determining whether a test agent causes a developmental defect. The methods can include (a) culturing a mammalian stem cell population under conditions that in the absence of the test agent result in the formation of a neuruloid as described herein, (b) exposing the culture of step (a) to the test agent, and (c) determining whether the test agent partially or wholly disrupts formation of the neuruloid, thereby determining whether the test agent causes a developmental defect. Exemplary methods of determining whether a test agent causes a developmental defect are further described in the Detailed Description and numbered embodiments 192 to 201, infia.

In one aspect, the invention provides a screening platform for identifying an agent that is biologically active against a disease phenotype comprising: (a) a first neuruloid as described herein whose cells comprise a genetic mutation associated with a disease, and (b) a second neuruloid as described herein whose cells lack the genetic mutation associated with the disease but are otherwise isogenic to the first neuruloid. Exemplary screening platforms are further described in the Detailed Description and numbered embodiments 202 to 206, infra.

DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

The invention relates to a neural ectodermal lineage cellular structure, and compositions and methods related thereto. As used herein, the neural ectodermal lineage cellular structure is also referred to as a "neuruloid".

In one aspect, the invention provides methods of forming neuruloids. The methods typically include the steps of (a) culturing mammalian stem cells seeded on a circular micropattern substrate under conditions of dual SMAD inhibition such that a colony comprising a lumen is formed; and (b) culturing the colony in the presence of a bone morphogenetic protein (BMP) under conditions under which neurulation occurs, thereby forming a neuruloid.

The neural ectodermal lineage cellular structure of the present invention can be generally characterized as comprising a multicellular structure having neuroepithelial cells that are the innermost cells in the structure and surround a lumen.

In particular, neuruloids according to the present invention can include spatially segregated neuroepithelial cells, sensory placodes, neural crest cells, and epidermal cells having radial organization around a lumen within the neuroepithelial cells.

The lumen is in the center of the neuroepithelial cells; the neural crest cells are adjacent to and around the neuroepithelial cells; the sensory placodes are within and surrounded by the neural crest cells; and the epidermal cells are the outermost cells of the structure and axially overlay the other cell types in the neuruloid. Neuruloids can in some instances include two sensory placodes.

Figure 13:
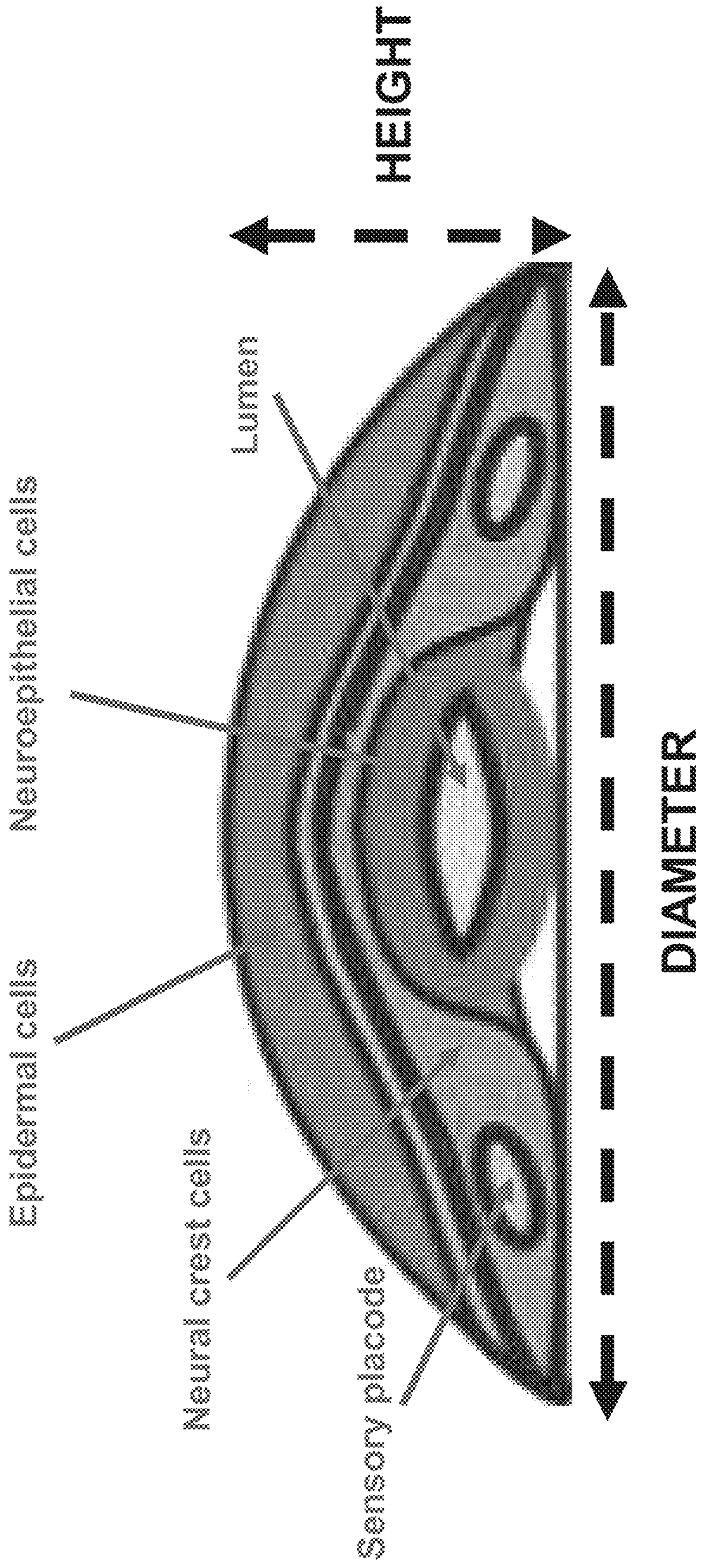
FIG. 13 depicts an exemplary embodiment of a neural ectodermal lineage cellular structure according to the present invention. The neuroepithelial cells are the innermost cells in the structure and surround a lumen. The lumen is in the center of the neuroepithelial cells; the neural crest cells are adjacent to and around the neuroepithelial cells; the sensory placodes are within and surrounded by the neural crest cells; and the epidermal cells are the outermost cells of the structure and axially overlay the other cell types in the neural ectodermal lineage cellular structure. The neural ectodermal lineage cellular structure shown in FIG. 13 includes two sensory placodes.

In an exemplary embodiment, the cells of a neuruloid of the disclosure are arranged substantially as shown in FIG. 13.

The neural ectodermal lineage cellular structure disclosed herein can be in the form of a tri-dimensional disc-shape.

In some embodiments, neuruloids of the disclosure have a diameter ranging from 80 μm to 1000 μm, 80 μm to 750 μm, or 200 μm to 600 μm, or any range bounded by any two of the foregoing values. In some embodiments, the neural ectodermal lineage cellular structure disclosed herein has a diameter of about 500 μm.

The neuruloids disclosed herein can have a height ranging, for example, from 10 μm-100 μm (e.g., 40 μm-60 μm). In some embodiments, the neuruloids disclosed herein have a height of about 50 μm.

In some embodiments, the epidermal cells of the neuruloids are arranged in a single layer.

The cells of a neuruloid can be identified by certain expression markers characteristic of the particular cell or lineage ("lineage markers" for convenience). For example, neuroepithelial cells express PAX6, sensory placode cells express SIX1, neural crest cells express SOX10, and epidermal cells express TFAP2A.

The term "marker" or "biomarker" refers generally to a DNA, RNA, protein, carbohydrate, or glycolipid-based molecular marker, the expression or presence of which in a cultured cell population can be detected by standard methods (or methods disclosed herein) and is consistent with one or more cells in the cultured cell population being a particular type of cell. The marker may be a polypeptide expressed by the cell or an identifiable physical location on a chromosome, such as a gene, a restriction endonuclease recognition site or a nucleic acid encoding a polypeptide (e.g., an mRNA) expressed by the native cell. The marker may be an expressed region of a gene referred to as a "gene expression marker", or some segment of DNA with no known coding function. The biomarkers may be cell-derived, e.g., secreted, products.

In order to identify the cell types within a neuruloid, the stem cells that are differentiated into neuruloids can be engineered to express a detectable protein, e.g., fluorescent protein, under the control of one or more lineage marker proteins.

Accordingly, the one or more lineage markers can be fluorescent markers. The one ore more lineage markers can include one or more sequences encoding one or more fluorescent proteins operably linked to the PAX6 promoter, N-CAD promoter, SOX10 promoter, or a combination thereof. Exemplary fluorescent proteins include GFP and variants such as YFP and RFP, DsRed, mPlum, mCherry, YPet, Emerald, CyPet, T-Sapphire, and Venus.

Alternatively, the lineage markers can be detected using one or more antibody directed against the markers. Antibodies suitable for particularly detecting the markers, such as antibodies directed against PAX6, N-CAD or SOX10, are known and available in the art. For example, marker antibodies can be utilized using immunofluorescence, including as described herein. Alternatively, probe molecules specific for the markers or suitable to detect marker RNA or protein expression can be utilized.

In accordance with the methods of forming neuruloids provided herein, in a first step mammalian stem cells seeded on a circular micropattern substrate are cultured under conditions of dual SMAD inhibition such that a colony comprising a lumen is formed. In step (a), mammalian stem cells are seeded on a circular micropattern substrate and cultured under conditions of dual SMAD inhibition such that a colony comprising a lumen is formed.

The mammalian stern cells used in the methods of forming neuruloids described herein can be from primary culture cells. Alternatively, the mammalian stem cells used in the methods of forming neuruloids described herein can be immortalized cells. The primary culture cells and the immortalized cells can be stem cells, e.g., totipotent stem cells or pluripotent stem cells. For example, the following cells can be used, pluripotent stein cells, induced pluripotent stem cells (iPSCs), adult stern cells, embryonic stem cells, or non-embryonic stem cells. In some embodiments the stem cells are human stem cells or human embryonic stein cells (hESC). In some embodiments, the cells are embryonic stem cells. In other embodiments, the cells are non-embryonic stem cells, for example adult stein cells. In some embodiments, the stein cells are induced pluripotent stem cells. Preferably, the stern cells are of human origin.

Established cell lines can be used. Established stem cell lines, particularly established human stem cell lines, are known and available. Examples of established cell lines include RUES1, RUES2, and RUES3 (rues.rockefeller).

The mammalian stem cells used in the methods of forming neuruloids described herein can contain one or more genetic mutations associated with a disease or condition. The genetic mutations can be introduced into the mammalian stem cell lines prior to culturing using known and available methods, particularly including gene replacement technologies. For example, the genetic mutations can be introduced into the mammalian stem cells prior to culturing (e.g., using CRISPR-Cas9 or TALEN). As another example, the mammalian stem cells can be iPSCs from subjects that have a disease or condition. Alternatively, the mammalian stem cells can be normal cells. As used herein, "normal" cells refer to WT cells that do not contain one or more genetic mutation associated with a disease or condition to be studied.

In some embodiments, the mammalian stem cells have one or more mutations associated with a neurodegenerative disorder, for example, Huntington's disease, Alzheimer's disease, Parkinson's disease, Rett syndrome, or amyotrophic lateral sclerosis (ALS). In some embodiments, the mammalian stem cells have one or more mutations associated with Huntington's disease. In some embodiments, the mammalian stem cell has one or more mutations associated with Huntington's disease and encodes a Huntingtin protein with an expanded polyglutamine repeat. See, e.g., WO/2017/147536. The polyglutamine repeat can have, for example, 42-150 glutamine residues (e.g., 42, 45, 48, 50, 56, 58, 67, 72, 74, or 150 glutamine residues). The polyglutamine repeat can have at least 42 repeats. The polyglutamine repeat can be 42 repeats or greater. In other embodiments, the mammalian stem cells have one or more mutations associated with Alzheimer's disease, Parkinson's disease, Rett syndrome, or amyotrophic lateral sclerosis (ALS).

In some embodiments, the mammalian stem cells have one or more mutations associated with a psychiatric disease. Examples of psychiatric diseases include schizophrenia, bipolar disorder, and epilepsy.

In some embodiments, the mammalian stem cells have one or more mutations associated with autism spectrum disorder, e.g., mutations associated with Fragile X syndrome. Such mutations typically entail an expansion of the CGG triplet repeat within the FMR1 (fragile X mental retardation 1) gene on the X chromosome.

In some embodiments, the mammalian stem cells have one or more mutations associated with cancer. In some embodiments, the mammalian stem cells have one or more mutations associated with predisposition to cancer or cancer risk, or one or more or a combination of cancer-linked mutations.

In some embodiments, the mammalian stem cells have one or more mutations associated with an infectious disease.

In some embodiments, the mammalian stem cells have one or more mutations associated with cystic fibrosis.

In the methods of forming neuruloids described herein, mammalian stem cells, e.g., as described above, can be seeded on a circular micropattern substrate under conditions of dual SMAD inhibition.

The term "micropattern" refers to a pattern having features on the microscale. For example, a micropattern can include repeating circles or spheres having a diameter on the micrometer scale, or a micropattern can include repeating lines having line widths on the micrometer scale, or a micropattern can include repeating units, e.g., squares, triangles, diamonds, rhomboids, or other two- or three-dimensional geometric shapes, said shapes having at least one feature, e.g., height, width, length, etc. on the micrometer scale. Other micropatterns are contemplated for use in the methods of the disclosure and can include free-form shapes and/or geometries, etc. Micropatterns can be generated using art-recognized micro-patterning techniques including, but not limited to lithography, stenciling, etching, and the like.

The circular micropattern substrate can be, for example, a slide, cover slip, or multi-well plate. In some embodiments, the circular micropattern substrate comprises a layer of porous material. Examples of suitable porous material includes a Matrigel, Cultrex, and Geltrex basement membrane matrix. In some embodiments, the circular micropattern substrate and/or the porous material, if present, is coated with a matrix-forming material. Examples of suitable matrix-forming material includes poly-D-lysine, poly-L-lysine, fibronectin, collagen, laminin, laminin-511 (LN-511), laminin-521 (LN-521), poly-L-ornithine, and any combination thereof.

In some embodiments, the circular micropattern substrate includes 1,000 to 10,000 circular micropatterns.

In some embodiments, each circular micropattern has a diameter ranging from 150 am to 1000 μm, 200 μm to 750 pum, 400 μm to 600 μm, or any range bounded by any two of the foregoing values. In some embodiments, each circular micropattern has a diameter of 400 to 600 μM. In some embodiments, each circular micropattern has a diameter of about 500 μM.

In some embodiments, the mammalian stem cells are seeded on a micropattern substrate at a density of 500 to 5000 cells per circular micropattern. In some embodiments, the mammalian stem cells are seeded on a micropattern substrate at a density of 1000 to 5000 cells per circular micropattern. In some embodiments, the mammalian stem cells are seeded on a micropattern substrate at a density of 500 to 3000 cells per circular micropattern.

In some embodiments, 100,000 to 1,000,000; 400,000 to 800,000; or 400,000 to 600,000 mammalian stem cells are seeded onto the micropattern substrate. In some embodiments, 400,000 to 600,000 mammalian stem cells are seeded onto the micropattern substrate. In some embodiments, about 500,000 mammalian stem cells are seeded onto the micropattern substrate.

SMAD inhibition includes blocking two signaling pathways that utilize SMADs for transduction. These two signaling pathways include the bone morphogenetic protein (BMP) pathway and the transforming growth factor-β (TGFB) pathway. An example of a BMP inhibitor includes LDN193189 and noggin protein. The noggin protein is preferably a vertebrate noggin protein. The noggin protein may be a vertebrate noggin protein, wherein the vertebrate is human, mouse, or *Xenopus*. The BMP inhibitor is preferably a BMP type I receptor inhibitor. In an embodiment, the BMP inhibitor is a BMP type I receptor inhibitor. In an embodiment, the BPM inhibitor is a BMP type I receptor inhibitor and inhibits ALK2 and ALK3. An example of a TGF-β inhibitor is SB431542. The TGF-β inhibitor is preferably an inhibitor of TGF-β receptor I, such as TGF-β superfamily type I activing receptor kinase receptor. The TGF-β inhibitor may be a TGF-β type I receptor-like kinase (ALK) receptor inhibitor and may inhibit ALK4, ALK5 and ALK7. In some embodiments, the TGF-β inhibitor is a TGF-β RI/ALK5 inhibitor. Suitable such inhibitors are known. The TGF-β inhibitor may be SB431542, S13525334, Galunisterib, GW788388, RepSox (SJN 2511) or R-268712. The TGF-β inhibitor may be A 83-01. The TGF-β inhibitor may be S13431542.

In some embodiments, mammalian stem cells are seeded onto the circular micropattern substrate prior to the dual SMAD inhibition conditions described above.

The cells can be cultured on the micropattern substrate until a colony comprising a lumen is formed. Such a colony may occur within a period of 3 to five days. In some embodiments, the mammalian stem cells are cultured for a period of 2 days to 6 days, 2 days to 5 days, 3 days to 4 days, or 3 days to 10 days.

A colony comprising a lumen can include neural progenitor cells that express Pax6. The colony can further display a radial organization. The cells at the center of the colony can express N-CADHERIN (N-CAD).

In some embodiments, SMAD inhibition includes blocking the bone morphogenetic protein (BM P) pathway with one or more BMP inhibitor. In some embodiments, conditions of dual SMAD inhibition includes a first medium including a BMP inhibitor having a concentration range of 0.1 μM to 0.5 μM, 0.1 μM to 0.4 μM, 0.1 μM to 0.3. 0.1 βM to 0.2 βM, or any range bounded by any two of the foregoing values. In some embodiments a BMP inhibitor is LDN193189. In some embodiments, conditions of dual SMAD inhibition includes a first medium including LDN193189 having a concentration range of 0.1 μM to 0.5 μM, 0.1 μM to 0.4 μM, 0.1 μM to 0.3, 0.1 μM to 0.2 μM, or any range bounded by any two of the foregoing values. In some embodiments, the first medium includes LDN193189 at a concentration of about 0.2 μM.

In some embodiments, SMAD inhibition includes blocking the transforming growth factor-β (TGFB) pathway with one or more TGFB pathway inhibitor. In some embodiments, conditions of dual SMAD inhibition includes a first medium including a TGF-β inhibitor having a concentration range of about 0.1 μM to 20 μM, 1 μM to 15 μM, 1 μM to 12 μM, 2 μM to 12 μM, 3 μM to 12 μM, 4 μM to 12 μM, 6 μM to 12 μM, 6 μM to 10 μM, 7 μM to 10 μM, 8 μM to 10 μM, 9 μM to 10 μM, or any range bounded by any two of the foregoing values.

In some embodiments a TGF-β inhibitor is S13431542. In some embodiments, conditions of dual SMAD inhibition includes a first medium including S13431542 having a concentration range of about 0.1 μM to 20 μM, 1 μM to 15 μM, 1 μM to 12 μM, 2 μM to 12 μM, 3 μM to 12 μM, 4 μM to 12 μM, 6 μM to 12 μM, 6 μM to 10 μM, 7 μM to 10 μM, 8 μM to 10 μM, 9 μM to 10 μM, or any range bounded by any two of the foregoing values. In some embodiments, the first medium includes S13431542 at a concentration of about 10 μM.

The first medium can include both a BMP inhibitor and a TGF-β inhibitor, for example, at concentrations within any of the ranges described above. The first medium can include both LDN193189 and SB431542, for example, at concentrations within any of the ranges described above.

In methods of forming neuroloids as provided herein, after the mammalian stem cells are seeded on a circular micropattern substrate under conditions of dual SMAD inhibition such that a colony comprising a lumen is formed, the colony is cultured in the presence of a bone morphogenetic protein (BMP) under conditions under which neurulation occurs, thereby forming a neuruloid. In some embodiments, after the mammalian stem cells are seeded on a circular micropattern substrate under conditions of dual SMAD inhibition such that a colony comprising a lumen is formed, the colony can be cultured in a second medium including bone morphogenic protein (BMP) under conditions which neurulation occurs to form a neuruloid as described above. In some embodiments, the colony is cultured in the second medium for a period of 3 days to 4 days, 5 days to 6 days, 7 days to 8 days, 9 days to 10 days, or 11 days to 15 days. In some embodiments, the colony is cultured in the presence of a BMP for a period of 3 days to 4 days, 5 days to 6 days, 7 days to 8 days, 9 days to 10 days, or 11 days to 15 days.

A preferred BMP is BMP4. The BM1P4 used can be a vertebrate BMP4 protein, for example, human, mouse, or xenopous BMP4.

In some embodiments, the second medium includes BMP4 at a concentration range of 1 to 100 ng/ml, 3 ng/ml to 90 ng/ml, 3 ng/ml to 80 ng/ml, 3 ng/ml to 70 ng/ml, 3 ng/ml to 50 ng/ml, 3 ng/ml to 25 ng/ml, 3 ng/ml to 15 ng/ml, 3 ng/ml to 13 ng/ml, 10 ng/ml to 50 ng/ml, 13 ng/ml to 50 ng/ml, or any range bounded by any two of the foregoing values. In some embodiments, the second medium includes BMP4 at a concentration of about 3 ng/nl, 13 ng/ml, or 50 ng/ml.

In some embodiments, after a colony comprising a lumen is formed, the colony is cultured in the presence of a bone morphogenetic protein (BMP) and in the presence of a TGF-β inhibitor under conditions under which neurulation occurs, thereby forming a neuruloid. The second medium can, in some embodiments, include a TGF-β inhibitor (e.g., SB431542) in addition to the BMP.

In some embodiments, the second medium includes SB431542 at a concentration range of 0.1 μM to 20 μM, 1 μM to 15 μM, 1 μM to 12 μM, 2 μM to 12 μM, 3 μM to 12 μM, 4 μM to 12 μM, 6 μM to 12 μM, 6 μM to 10 μM, 7 μM to 10 μM, 8 μM to 10 μM, 9 μM to 10 μM, or any range bounded by any two of the foregoing values. In some embodiments, the second medium includes SB431542 at a concentration of about 10 μM.

Appropriate culture conditions for mammalian cells are well known in the art or can be determined by the skilled artisan (see, for example, Animal Cell Culture: A Practical Approach 2$^{nd}$ Ed., Rickwood, D. and Hames, B. D., eds. (Oxford University Press: New York, 1992)), and vary according to the particular cell selected. Commercially available media can be utilized. Non-limiting examples of media include, for example, Dulbecco's Modified Eagle Medium (DMEM, Life Technologies), Dulbecco's Modified Eagle Medium/Nutrient Mixture F-12 (DMEM/F-12, Life Technologies), Minimal Essential Medium (MEM, Sigma, St. Louis, Mo.), and hepatocyte medium.

The media described above can be supplemented as necessary with supplementary components or ingredients, including optional components, in appropriate concentrations or amounts, as necessary or desired. Cell medium solutions provide at least one component from one or more of the following categories: (1) an energy source, usually in the form of a carbohydrate such as glucose; (2) all essential amino acids, and usually the basic set of twenty amino acids plus cysteine; (3) vitamins and/or other organic compounds required at low concentrations; (4) free fatty acids or lipids, for example linoleic acid; and (5) trace elements, where trace elements are defined as inorganic compounds or naturally occurring elements that are typically required at very low concentrations, usually in the micromolar range.

The medium also can be supplemented electively with one or more components from any of the following categories: (1) salts, for example, magnesium, calcium, and phosphate; (2) hormones and other growth factors such as, serum, insulin, transferrin, epidermal growth factor, and fibroblast growth factor; (3) protein and tissue hydrolysates, for example peptone or peptone mixtures which can be obtained from purified gelatin, plant material, or animal byproducts; (4) nucleosides and bases such as, adenosine, thymidine, and hypoxanthine; (5) buffers, such as HEPES; (6) antibiotics, such as gentamycin or ampicillin; (7) cell protective agents, for example, pluronic polyol; and (8) galactose.

In an aspect, the invention includes neuruloids formed from mammalian cells on a circular micropattern substrate (e.g., formed by a method of forming a neuruloid as described herein). Neuruloids of the disclosure typically include spatially segregated neuroepithelial cells, sensory placodes, neural crest cells, and epidermal cells, and whose cells display radial organization around a lumen within the neuroepithelial cells. Neuruloids of the disclosure typically include spatially segregated neuroepithelial cells, sensory placodes, neural crest cells, and epidermal cells, wherein the cells display radial organization around a lumen within the neuroepithelial cells. In one embodiment, the mammalian cells are human cells.

In some embodiments, the invention includes a neuruloid as described above.

In some embodiments, the invention includes a neuruloid obtained or obtainable by the methods described above.

In an aspect, the invention provides a method of determining whether a test agent is biologically active against a disease phenotype comprising: (a) culturing a first mammalian stem cell population that in the absence of test agent forms a neuruloid that exhibits a disease phenotype with the test agent so as to form a first neuruloid, and (b) culturing a second mammalian stem population (c) determining whether the test agent partially or wholly reverses a disease phenotype associated with a second neuruloid obtained from a second mammalian stem cell population cultured under the same conditions but which is not exposed to the test agent, thereby determining whether the test agent is biologically active against the disease phenotype.

In one aspect, the invention provides a method of determining whether a test agent is biologically active against a disease phenotype comprising: (a) culturing a first mammalian stern cell population under conditions that in the absence of the test agent result in the formation of a first neuruloid that exhibits a disease phenotype, (b) exposing the culture of step (a) to the test agent, and (c) determining whether the test agent partially or wholly reverses a disease phenotype associated with a second neuruloid obtained from a second mammalian stem cell population cultured under the same conditions but which is not exposed to the test agent, thereby determining whether the test agent is biologically active against the disease phenotype.

In some embodiments, the second mammalian stem cell population is cultured under the same conditions as the first mammalian stem cell population to obtain a second neuruloid whose cells comprise the same genetic mutation as the first mammalian stem cell population.

In some embodiments, the second mammalian stem cell population is cultured concurrently with the first mammalian stem cell population.

In some embodiments, a third mammalian stern cell population whose cells lack the genetic mutation is cultured under the same conditions as the first mammalian stem cell population to obtain a third neuruloid. The third mammalian stern cell population may be cultured concurrently with the first mammalian stein cell population.

In some embodiments, the method further includes evaluating whether the test agent alters a non-disease phenotype in the third neuruloid.

In some embodiments, the mammalian stein cells are cultured under conditions described above and/or result in the product of a neuronal ectodermal lineage cell structure described above.

In some embodiments, step (b) is performed concurrently with step (a). In some embodiments, step (b) is performed concurrently with only part of step (a). In some embodiments, step (b) is performed concurrently with the entirety of step (a).

In an aspect, the invention provides a method of determining whether a test agent is biologically active against a disease phenotype comprising: (a) culturing a first mammalian stem cell population under conditions that in the absence of the test agent result in the formation of a first neuruloid that exhibits a disease phenotype, (b) exposing the culture of step (a) to the test agent, (c) culturing a second mammalian stem cell population in the absence of the test agent under conditions that result in the formation of a second neuruloid that exhibits a disease phenotype, and (d) determining whether the test agent partially or wholly reverses a disease phenotype associated with the first neuruloid, thereby determining whether the test agent is biologically active against the disease phenotype.

In some embodiments, the invention provides a method of determining whether a test agent is biologically active against a disease phenotype, wherein the disease is a genetic disorder associated with Huntington's disease and the disease phenotype is a phenotype associated with Huntington's disease. In some embodiments, the disease phenotype may be caused by an exogenous agent, for example, a teratogen or a pathogen.

As used herein, "teratogen" includes any environmental factor that can cause an abnormality in form (e.g., a birth defect) or function (e.g., mental retardation) in an exposed embryo or fetus. The term encompasses any compound that can cause abnormalities in a fetus exposed to the compound.

As used herein, "pathogen" includes any organism that exists within a host cell, either in the cytoplasm or within a vacuole, for at least part of its reproductive or life cycle. Examples of pathogens include bacteria, viruses, fungi, and intracellular parasites.

The exogenous agent can be present during the culturing of the first mammalian stem cell population, as described above. In some embodiments, the first mammalian stem cell population is cultured for a period of time before addition of the exogenous agent.

A test agent can be considered biologically active against a disease phenotype if the test agent partially or wholly reverts the disease phenotype to the wild type or non-disease phenotype.

In one aspect, the invention provides a method of determining whether a test agent causes a developmental defect, comprising: (a) culturing a mammalian stem cell population under conditions that in the absence of the test agent result in the formation of a neural ectodermal lineage cellular structure described herein, (b) exposing the culture of step (a) to the test agent, and (c) determining whether the test agent partially or wholly disrupts formation of the neural ectodermal lineage structure, thereby determining whether the test agent causes a developmental defect.

In some embodiments, the mammalian stem cell population is a normal stem cell population.

In some embodiments, the mammalian stem cells are cultured under conditions described above and/or result in the product of a neuruloid described above.

In some embodiments, step (b) is performed concurrently with step (a). In some embodiments, step (b) is performed concurrently with only part of step (a). In some embodiments, step (b) is performed concurrently with the entirety of step (a).

In some embodiments, the method is carried out at different concentrations of the test agent. In some embodiments, the different concentrations of the test agent are tested concurrently or serially.

In some embodiments, the method of determining whether a test agent causes a developmental defect described above further comprises determining the teratogenic concentration of a test agent that disrupts formation of the neuruloid.

In one aspect, the invention provides a screening platform for identifying an agent that is biologically active against a disease phenotype comprising: (a) a first neuruloid structure described herein whose mammalian cells comprise a genetic mutation associated with a disease, and (b) a second neuruloid as described herein whose mammalian cells lack the genetic mutation associated with the disease but are otherwise isogenic to the first neural ectodermal lineage cellular structure.

In some embodiments, the genetic mutation is associated with a neurodegenerative disorder. In some embodiments, the neurodegenerative disorder is Huntington's disease.

In some embodiments, the mammalian cells encode a Huntingtin protein with an expanded polyglutamine repeat, wherein the polyglutamine repeat includes 42-150 glutamine residues (e.g., 42, 45, 48, 50, 56, 58, 67, 72, 74, or 150 glutamine residues). In some embodiments, the mammalian cells encode a Huntingtin protein with an expanded polyglutamine repeat including 42 or more glutamine residues. In some embodiments, the mammalian cells encode a Huntingtin protein with an expanded polyglutamine repeat at least 42 glutamine residues. In some embodiments, the mammalian cells encode a Huntingtin protein with an expanded polyglutamine repeat including 56 or more glutamine residues. In some embodiments, the mammalian cells encode a Huntingtin protein with an expanded polyglutamine repeat including 72 or more glutamine residues.

The screening platforms described herein can be used, for example, to screen one or more agents to identify one or more agents biologically active against a disease phenotype. "Screening" refers to the process in which one or more properties of one or more molecules are determined. For example, typical screening processes include those in which one or more properties of one or more molecules that are members of one or more libraries are determined.

A "library" refers to a collection of at least two different molecules, such as small molecule compounds, proteins, peptides, or nucleic acids. For example, a library typically includes at least about 10 different molecules. Large libraries typically include at least about 100 different molecules, more typically at least about 1,000 different molecules. For some applications, the library includes at least about 10,000 or more different molecules.

"Selection" refers to the process in which one or more molecules are identified as having one or more properties of interest. Thus, for example, one can screen a library with a screening platform of the disclosure to determine one or more properties of one or more library members, such as reversion of a disease phenotype to a WT (non-disease) phenotype or toxicity. If one or more of the library members is/are identified as possessing a property of interest (e.g., reversion of a disease phenotype to a WT phenotype), it can be selected. Selection can include the isolation of a library member and further testing, e.g., in an animal model. Further, selection and screening can be, and often are, simultaneous.

Cells having the same or closely similar genotypes can be considered "isogenic." For example, a normal stem cell can be modified to have a disease form of a gene, and the resulting modified cell line can be considered isogenic to the normal cell line. As another example, a stem cell line having a mutant gene associated with a disease phenotype can be corrected to provide a stem cell line having a non-disease phenotype that is isogenic to the parental stein cell line. Other variations may include the incorporation of one, two three or more markers, and/or one or more variations unintentionally introduced when modifying the parental cell line (e.g., an off-target mutation introduced when using CRISPR-Cas9 mediated gene editing). The resulting cell will still be considered isogenic to the cell from which it was modified. In some of the methods described herein, an isogenic control cell or an isogenic wild-type cell is used. Cell line pairs (and organoids made from such cell line pairs) that are isogenic, e.g., they share the same genetic background except for one or a small number (such as 2, 3, 4, 5, or 10) of variances (for example variances that are introduced by genetically modifying the cell), allow for the study of specific genetic variances compared to the wild-type cells and alleviate complications introduced by comparing different patient cells which can vary by a multitude of genetic features (especially but not exclusively genetic features that are not known).

SPECIFIC EMBODIMENTS

The present disclosure is exemplified by the specific embodiments below.

1. A method of forming a neural ectodermal lineage cellular structure, comprising:
   - (a) culturing mammalian stem cells seeded on a circular micropattern substrate under conditions of dual SMAD inhibition such that a colony comprising a lumen is formed; and
   - (b) culturing the colony in the presence of a bone morphogenetic protein (BMP) under conditions under which neurulation occurs, thereby forming a neural ectodermal lineage cellular structure.

2. The method of embodiment 1, wherein the colony produced in step (a) comprises neural progenitor cells.

3. The method of embodiment 2, wherein the neural progenitor cells express Pax6.

4. The method of any one of embodiments 1 to 3, wherein the colony produced in step (a) displays radial organization.

5. The method of embodiment 4, wherein the cells in the center of the colony produced in step (a) express N-CAD.

6. The method of any one of embodiments 1 to 5, wherein the neural ectodermal lineage cellular structure produced in step (b) is disc-shaped.

7. The method of embodiment 6, wherein the neural ectodermal lineage cellular structure is a trin-dimensional disc-shape.

8. The method of any one of embodiments 1 to 7, wherein the neural ectodermal lineage cellular structure produced in step (b) is 150 μm to 1000 μm in diameter.

9. The method of embodiment 8, wherein the neural ectodermal lineage cellular structure produced in step (b) has a diameter ranging from 200 μm to 750 μm.

10. The method of embodiment 9, wherein the neural ectodermal lineage cellular structure produced in step (b) has a diameter ranging from 400 μm to 600 lim.

11. The method of embodiment 9, wherein the neural ectodermal lineage cellular structure produced in step (b) has a diameter of 500 μm.

12. The method of any one of embodiments 1 to 11, wherein the neural ectodermal lineage structure is 10 μm-100 μm in height.

13. The method of embodiment 12, wherein the neural ectodermal lineage structure is 40 μm-60 μm in height.

14. The method of embodiment 13, wherein the neural ectodermal lineage structure is 50 μm in height.

15. The method of any one of embodiments 1 to 14, wherein the neural ectodermal lineage cellular structure produced in step (b) comprises (i) neuroepithelial cells surrounding a lumen, (ii) sensory placodes, (iii) neural crest cells, and (iv) epidermal cells.

16. The method of embodiment 15, wherein the neuroepithelial cells, sensory placodes, neural crest cells, and epidermal cells are radially organized.

17. The method of embodiment 16, wherein the neuroepithelial cells, sensory placodes, neural crest cells, and epidermal cells are spatially segregated.

18. The method of any one of embodiments 15 to 17, wherein
   - (a) the neuroepithelial cells are the innermost cells in the structure and surround a lumen;
   - (b) the neural crest cells are adjacent to and around the neuroepithelial cells;
   - (c) the sensory placodes are within and surrounded by the neural crest cells; and
   - (d) the epidermal cells are the outermost cells of the structure and axially overlay the other cell types in the neural ectodermal lineage cellular structure.

19. The method of any one of embodiments 15 to 18, wherein the cells are arranged substantially as shown in FIG. 13.

20. The method of any one of embodiments 15 to 19, wherein the epidermal cells are arranged in a single layer.

21. The method of any one of embodiments 15 to 20, wherein the neuroepithelial cells express PAX6.

22. The method of any one of embodiments 15 to 21, wherein the sensory placode cells express SIX1.

23. The method of any one of embodiments 15 to 22, wherein the neural crest cells express SOX10.

24. The method of any one of embodiments 15 to 23, wherein the epidermal cells express TFAP2A.

25. The method of any one of embodiments 15 to 24, wherein the mammalian stein cells are engineered to express lineage markers.

26. The method of embodiment 25, wherein the lineage markers are fluorescent markers.

27. The method of embodiment 25 or embodiment 26, wherein the lineage markers comprise one or more sequences encoding one or more fluorescent proteins operably linked to the PAX6, N-CAD, SOX10 promoters, or a combination thereof.

28. The method of any one of embodiments 1 to 27, wherein the cultured cells are geometrically confined by the circular micropattern substrate.

29. The method of any one of embodiments 1 to 28, wherein the circular micropattern has a diameter ranging from 150 μm to 1000 μm.

30. The method of embodiment 29, wherein the circular micropattern has a diameter ranging from 200 μm to 750 μm.

31. The method of embodiment 29, wherein the circular micropattern has a diameter ranging from 400 μm to 600 μm.

32. The method of embodiment 29, wherein the circular micropattern has a diameter of 500 μm.

33. The method of any one of embodiments 1 to 32, wherein step (a) comprises culturing the mammalian stem cells in a first medium comprising two SMAD inhibitors.

34. The method of embodiment 33, wherein the two SMAD inhibitors are a BMP inhibitor and a transforming growth factor beta (TGF-β) inhibitor.

35. The method of embodiment 34, wherein the BMP inhibitor is LDN193189.

36. The method of embodiment 35, wherein the first medium comprises 0.1 μM to 0.5 μM LDN193189.

37. The method of embodiment 35, wherein the first medium comprises 0.1 μM to 0.4 μM LDN193189.

38. The method of embodiment 35, wherein the first medium comprises 0.1 μM to 0.3 μM LDN193189.

39. The method of embodiment 35, wherein the first medium comprises 0.1 μM to 0.2 μM LDN193189.

40. The method of embodiment 35, wherein the first medium comprises 0.2 μM LDN193189.

41. The method of any one of embodiments 34 to 40, wherein the TGF-β inhibitor is SB431542.

42. The method of embodiment 41, wherein the first medium comprises 0.1 μM to 20 μM SB431542.

43. The method of embodiment 41, wherein the first medium comprises 1 μM to 15 μM SB431542.

44. The method of embodiment 41, wherein the first medium comprises 1 μM to 12 μM SB431542.

45. The method of embodiment 41, wherein the first medium comprises 2 μM to 12 μM SB431542.

46. The method of embodiment 41, wherein the first medium comprises 3 μM to 12 μM SB431542.

47. The method of embodiment 41, wherein the first medium comprises 4 μM to 12 μM SB431542.

48. The method of embodiment 41, wherein the first medium comprises 6 μM to 12 μM SB431542.

49. The method of embodiment 41, wherein the first medium comprises 6 μM to 10 μM SB431542.

50. The method of embodiment 41, wherein the first medium comprises 7 μM to 10 μM SB431542.

51. The method of embodiment 41, wherein the first medium comprises 8 μM to 10 μM SB431542.

52. The method of embodiment 41, wherein the first medium comprises 9 μM to 10 μM SB431542.

53. The method of embodiment 41, wherein the first medium comprises 10 μM SB431542.

54. The method of embodiment 34, wherein the BMP inhibitor is noggin.

55. The method of embodiment 54, wherein noggin is a vertebrate noggin protein.

56. The method of embodiment 55, wherein the vertebrate is human, mouse, or *Xenopus*.

57. The method of any one of embodiments 33 to 56, wherein the method further comprises the step of removing the first medium between steps (a) and (b).

58. The method of any one of embodiments 1 to 57, wherein step (b) comprises culturing the cells produced in step (a) in a second medium comprising the BMP.

59. The method of embodiment 58, wherein the BMP is BMP4.

60. The method of embodiment 59, wherein the BM P4 is a vertebrate BMP4 protein.

61. The method of embodiment 60, wherein the vertebrate is human, mouse, or *Xenopus*

62. The method of any one of embodiments 59 to 61, wherein the second medium comprises 1 to 100 ng/ml BMP4.

63. The method of embodiment 62, wherein the second medium comprises 3 ng/ml to 90 ng/ml BMP4.

64. The method of embodiment 62, wherein the second medium comprises 3 ng/ml to 80 ng/ml BMP4.

65. The method of embodiment 62, wherein the second medium comprises 3 ng/ml to 70 ng/ml BMP4.

66. The method of embodiment 62, wherein the second medium comprises 3 ng/ml to 50 ng/ml BMP4.

67. The method of embodiment 62, wherein the second medium comprises 3 ng/ml to 25 ng/ml BMP4.

68. The method of embodiment 62, wherein the second medium comprises 3 ng/ml to 15 ng/ml BMP4.

69. The method of embodiment 62, wherein the second medium comprises, 3 ng/ml to 13 ng/ml BMP4.

70. The method of embodiment 62, wherein the second medium comprises 10 ng/ml to 50 ng/ml BMP4.

71. The method of embodiment 62, wherein the second medium comprises 13 ng/ml to 50 ng/ml BMP4.

72. The method of embodiment 62, wherein the second medium comprises 3 ng/ml BMP4.

73. The method of embodiment 62, wherein the second medium comprises 13 ng/ml BMP4.

74. The method of embodiment 62, wherein the second medium comprises 50 ng/ml BMP4.

75. The method of any one of embodiments 1 to 74, wherein step (b) comprises culturing the cells produced in step (a) in the presence of a TGF-β inhibitor in addition to the BMP.

76. The method of embodiment 75, wherein step (b) comprises culturing the cells produced in step (a) in a second medium comprising the BMP and the TGF-§ inhibitor.

77. The method of embodiment 76, wherein the TGF-β inhibitor is SB431542.

78. The method of embodiment 77, wherein the second medium comprises 0.1 μM to 20 μM SB431542.

79. The method of embodiment 77, wherein the second medium comprises 1 μM to 15 μM SB431542.

80. The method of embodiment 77, wherein the second medium comprises 1 μM to 12 μM SB431542.

81. The method of embodiment 77, wherein the second medium comprises 2 μM to 12 μM SB431542.

82. The method of embodiment 77, wherein the second medium comprises 3 μM to 12 μM SB431542.

83. The method of embodiment 77, wherein the second medium comprises 4 μM to 12 μM SB431542.

84. The method of embodiment 77, wherein the second medium comprises 6 μM to 12 μM SB431542.

85. The method of embodiment 77, wherein the second medium comprises 6 μM to 10 μM SB431542.

86. The method of embodiment 77, wherein the second medium comprises 7 μM to 10 μM SB431542.

87. The method of embodiment 77, wherein the second medium comprises 8 μM to 10 βM SB431542.

88. The method of embodiment 77, wherein the second medium comprises 9 μM to 10 μM SB431542.

89. The method of embodiment 77, wherein the second medium comprises 10 μM SB431542.

90. The method of any one of embodiments 1 to 89, which further comprises, prior to step (a), seeding the mammalian stem cells onto the circular micropattern substrate.

91. The method of any one of embodiments 1 to 90, wherein the circular micropattern substrate comprises 1,000 to 10,000 circular micropatterns.

92. The method of embodiment 91, wherein each circular micropattern has a diameter ranging from 150 μm to 1000 μm.

93. The method of embodiment 92, wherein each circular micropattern has a diameter ranging from 200 μm to 750 μm.

94. The method of embodiment 93, wherein each circular micropattern has a diameter ranging from 400 μm to 600 μm.

95. The method of embodiment 94, wherein each circular micropattern has a diameter of 500 μM.

96. The method of any one of embodiments 1 to 95, wherein the circular micropattern substrate is a slide, cover slip, or multi-well plate.

97. The method of embodiment, wherein the circular micropattern substrate comprises a layer of porous material.

98. The method of embodiment 97, wherein the porous material is a Matrigel, Cultrex, or Geltrex basement membrane matrix.

99. The method of any one of embodiments 1 to 98, wherein the circular micropattern substrate and/or the porous material, if present, is coated with a matrix-forming material.

100. The method of embodiment 99, wherein matrix-forming material is poly-D-lysine, poly-L-lysine, fibronectin, collagen, laminin, laminin-511 (LN-511), laminin-521 (LN-521), poly-L-ornithine, and any combination thereof.

101. The method of any one of embodiments 1 to 100, wherein the mammalian stem cells are seeded at a density of 500 to 5000 cells per circular micropattern.

102. The method of any one of embodiments 1 to 101, wherein 100,000 to 1,000,000 mammalian stem cells are seeded onto the micropattern substrate.

103. The method of embodiment 102, wherein 400,000 to 600,000 mammalian stem cells are seeded onto the micropattern substrate.

104. The method of embodiment 103, wherein 500,000 mammalian stem cells are seeded onto the micropattern substrate.

105. The method of any one of embodiments 1 to 104, where in the mammalian stem cells are normal cells.

106. The method of any one of embodiments 1 to 104, where in the mammalian stem cells have one or more mutations associated with a disease or condition.

107. The method of embodiment 106, wherein the mammalian stem cells have one or more mutations associated with a neurodegenerative disorder.

108. The method of embodiment 107, wherein the neurodegenerative disorder is Huntington's disease.

109. The method of embodiment 108, wherein the mammalian cells encode a Huntingtin protein with an expanded polyglutamine repeat.

110. The method of embodiment 109, wherein the polyglutamine repeat has 42-150 glutamine residues.

111. The method of embodiment 110, wherein the polyglutamine repeat has 42 glutamine residues.

112. The method of embodiment 110, wherein the polyglutamine repeat has 45 glutamine residues.

113. The method of embodiment 110, wherein the polyglutamine repeat has 48 glutamine residues.

114. The method of embodiment 110, wherein the polyglutamine repeat has 50 glutamine residues.

115. The method of embodiment 110, wherein the polyglutamine repeat has 56 glutamine residues.

116. The method of embodiment 110, wherein the polyglutamine repeat has 58 glutamine residues.

117. The method of embodiment 110, wherein the polyglutamine repeat has 67 glutamine residues.

118. The method of embodiment 110, wherein the polyglutamine repeat has 72 glutamine residues 119. The method of embodiment 110, wherein the polyglutamine repeat has 74 glutamine residues.

120. The method of embodiment 110, wherein the polyglutamine repeat has 150 glutamine residues.

121. The method of embodiment 107, wherein the neurodegenerative disorder is Alzheimer's disease.

122. The method of embodiment 107, wherein the neurodegenerative disorder is Parkinson's disease.

123. The method of embodiment 107, wherein the neurodegenerative disorder is Rett syndrome.

124. The method of embodiment 107 wherein the neurodegenerative disorder is ALS.

125. The method of embodiment 106, wherein the mammalian stem cells have one or more mutations associated with a psychiatric disease.

126. The method of embodiment 125, wherein the psychiatric disease is schizophrenia.

127. The method of embodiment 125, wherein the psychiatric disease is bipolar disorder.

128. The method of embodiment 125, wherein the psychiatric disease is epilepsy.

129. The method of embodiment 106, wherein the mammalian stem cells have one or more mutations associated with autism spectrum disorder, e.g., one more mutations associated with Fragile X syndrome.

130. The method of embodiment 106, wherein the mammalian stem cells have one or more mutations associated with cancer.

131. The method of embodiment 106, wherein the mammalian stern cells have one or more mutations associated with an infectious disease.

132. The method of embodiment 106, wherein the mammalian stem cells have one or more mutations associated with cystic fibrosis.

133. The method of any one of embodiments 106 to 132 which comprises, prior to step (a), introducing the one or more genetic mutations into the mammalian stem cells.

134. The method of any one of embodiments 1 to 133, where in the mammalian stem cells are pluripotent stem cells.

135. The method of embodiment 134, where in the pluripotent stem cells are induced pluripotent stem cells.

136. The method of any one of embodiments 1 to 133, where in the mammalian stem cells are totipotent stem cells.

137. The method of embodiment 136, where in the totipotent stem cells are embryonic stem cells.

138. The method of any one of embodiments 1 to 137, wherein the mammalian stem cells are from an immortalized cell line.

139. The method of embodiment 138, wherein the immortalized cell line is RUES1, RUES2, or RUES3.

140. The method of any one of embodiments 1 to 137, wherein the mammalian stem cells are primary cells.

141. The method of any one of embodiments 1 to 140, wherein the mammalian stem cells are human stem cells.

142. The method of any one of embodiments 1 to 141, wherein step (a) comprises culturing the mammalian stem cells for 2 days to 6 days.

143. The method of embodiment 142, wherein step (a) comprises culturing the mammalian stem cells for a period of 2 days to 5 days.

144. The method of embodiment 142, wherein step (a) comprises culturing the mammalian stem cells for a period of 3 days to 4 days.

145. The method of any one of embodiments 1 to 144, wherein step (b) comprises culturing the colony produced in step (a) for a period of 3 days to 10 days.

146. The method of embodiment 145, wherein step (b) comprises culturing the colony for 3 days to 4 days.

147. The method of embodiment 145, wherein step (b) comprises culturing the colony for 5 days to 6 days.

148. The method of embodiment 145, wherein step (b) comprises culturing the colony for 7 days to 8 days.

149. The method of embodiment 145, wherein step (b) comprises culturing the colony for 9 days to 10 days.

150. The method of embodiment 145, wherein step (b) comprises culturing the colony for 11 days to 15 days.

151. A neural ectodermal lineage cellular structure formed from mammalian cells on a circular micropattern substrate, comprising spatially segregated neuroepithelial cells, sensory placodes, neural crest cells, and epidermal cells, and whose cells display radial organization around a lumen within the neuroepithelial cells.

152. The neural ectodermal lineage cellular structure of embodiment 151 in which the lumen is in the center of the neuroepithelial cells.

153. The neural ectodermal lineage cellular structure of embodiment 151 or embodiment 152 in which:

(a) the neuroepithelial cells are the innermost cells in the structure and surround a lumen;

(b) the neural crest cells are adjacent to and around the neuroepithelial cells;

(c) the sensory placodes are within and surrounded by the neural crest cells; and (d) the epidermal cells are the outermost cells of the structure and axially overlay the other cell types in the neural ectodermal lineage cellular structure.

154. The neural ectodermal lineage cellular structure of any one of embodiments 151 to 153, comprising two sensory placodes.

155. The neural ectodermal lineage cellular structure of any one of embodiments 151 to 154 in which the cells are arranged substantially as shown in FIG. A.

156. The neural ectodermal lineage cellular structure of any one of embodiments 151 to 155 in which the epidermal cells are arranged in a single layer.

157. The neural ectodermal lineage cellular structure of any one of embodiments 151 to 156 in which the neuroepithelial cells express PAX6.

158. The neural ectodermal lineage cellular structure of any one of embodiments 151 to 157 in which the sensory placode cells express SIX1.

159. The neural ectodermal lineage cellular structure of any one of embodiments 151 to 158 in which the neural crest cells express SOX10.

160. The neural ectodermal lineage cellular structure of any one of embodiments 151 to 159 in which the epidermal cells express TFAP2A.

161. The neural ectodermal lineage cellular structure of any one of embodiments 151 to 160 whose cells are engineered to express lineage markers.

162. The neural ectodermal lineage cellular structure of embodiment 161, wherein the lineage markers are fluorescent markers.

163. The neural ectodermal lineage cellular structure of embodiment 161 or embodiment 162, wherein the lineage markers comprise one or more sequences encoding one or more fluorescent proteins operably linked to the PAX6 promoter, N-CAD promoter, SOX10 promoter, or a combination thereof.

164. The neural ectodermal lineage cellular structure of any one of embodiments 151 to 163 which is disc-shaped.

165. The neural ectodermal lineage cellular structure of embodiment 164 which is a tri-dimensional disc-shape.

166. The neural ectodermal lineage cellular structure of any one of embodiments 151 to 165 which has a diameter of 80 μm to 1000 μm.

167. The neural ectodermal lineage cellular structure of embodiment 166 which has a diameter ranging from 80 μm to 750 μm.

168. The neural ectodermal lineage cellular structure of embodiment 166 which has a diameter ranging from 200 μm to 600 μm.

169. The neural ectodermal lineage cellular structure of embodiment 166 which has a diameter of 500 μm.

170. The neural ectodermal lineage cellular structure of any one of embodiments 151 to 169 which is 10 μm-100 μm in height.

171. The neural ectodermal lineage cellular structure of embodiment 170 which is 40 μm-60 μm in height.

172. The neural ectodermal lineage cellular structure of embodiment 171 which is 50 μm in height.

173. The neural ectodermal lineage cellular structure of any one of embodiments 151 to 172, wherein the mammalian cells are human cells.

174. The neural ectodermal lineage cellular structure of any one of embodiments 151 to 173, which is obtained or obtainable by the method of any one of embodiments 1 to 150.

175. A method of determining whether a test agent is biologically active against a disease phenotype comprising:

(a) culturing a first mammalian stem cell population under conditions that in the absence of a test agent result in the formation of a first neural ectodermal lineage cellular structure that exhibits a disease phenotype, (b) exposing the culture of step (a) to the test agent, and (c) determining whether the test agent partially or wholly reverses a disease phenotype associated with a second neural ectodermal lineage cellular structure obtained from a second mammalian stem cell population cultured under the same conditions but which is not exposed to the test agent, thereby determining whether the test agent is biologically active against the disease phenotype.

176. The method of embodiment 175, wherein the first mammalian stem cell population is a normal cell population.

177. The method of embodiment 175 or embodiment 176, wherein the disease phenotype is caused by an exogenous agent to which the first mammalian stem cell population is exposed during the culture of step (a).

178. The method of embodiment 177, wherein the exogenous agent is a teratogen.

179. The method of embodiment 177, wherein the exogenous agent is a pathogen.

180. The method of embodiment 175, wherein the cells of the first mammalian cell population comprise a genetic mutation associated with the disease phenotype and wherein the cells of the second mammalian cell population comprises the same genetic mutation.

181. The method of embodiment 180, which further comprising culturing the second mammalian stem cell population under the same conditions as the first mammalian stem cell population to obtain a second neuronal ectodermal lineage cell structure whose cells comprise the same genetic mutation as the first mammalian stem cell population.

182. The method of embodiment 181, wherein the second mammalian stem cell population is cultured concurrently with the first mammalian stem cell population.

183. The method of any one of embodiments 180 to 182, which further comprises culturing a third mammalian stem cell population whose cells lack the genetic mutation under the same conditions as the first mammalian stem cell population to obtain a third neuronal ectodermal lineage cell structure.

184. The method of embodiment 183, which further comprises evaluating whether the test agent alters a non-disease phenotype in the third neuronal ectodermal lineage cell structure.

185. The method of embodiment 183 or embodiment 184, wherein the third mammalian stem cell population is cultured concurrently with the first mammalian stem cell population.

186. The method of any one of embodiments 175 to 185, wherein the culturing conditions result in the product of a neuronal ectodermal lineage cell structure according to any one of embodiments 151 to 174.

187. The method of any one of embodiments 175 to 186, wherein the culturing conditions are according to any one of embodiments 1 to 150.

188. The method of any one of embodiments 175 to 187, wherein step (b) is performed concurrently with step (a).

189. The method of embodiment 188, wherein step (b) is performed concurrently with only part of step (a).

190. The method of embodiment 188, wherein step (b) is performed concurrently with the entirety of step (a).

191. The method of any one of embodiments 180 to 190, wherein the wherein the disease is a genetic disorder associated with Huntington's disease.

192. A method of determining whether a test agent causes a developmental defect, comprising:

(a) culturing a mammalian stem cell population under conditions that in the absence of the test agent result in the formation of a neural ectodermal lineage cellular structure according to any one of embodiments 151 to 174, (b) exposing the culture of step (a) to the test agent, and (c) determining whether the test agent partially or wholly disrupts formation of the neural ectodermal lineage structure, thereby determining whether the test agent causes a developmental defect.

193. The method of embodiment 192, wherein the mammalian stem cell population is a normal stem cell population.

194. The method of embodiment 192 or embodiment 193, wherein the culturing conditions are according to any one of embodiments 1 to 150.

195. The method of any one of embodiments 192 to 194, wherein step (b) is performed concurrently with step (a).

196. The method of embodiment 195, wherein step (b) is performed concurrently with only part of step (a).

197. The method of embodiment 195, wherein step (b) is performed concurrently with the entirety of step (a).

198. The method of any one of embodiments 192 to 197, in which the method is carried out at different concentrations of the test agent.

199. The method of embodiment 198, wherein the different concentrations of the test agent are tested concurrently.

200. The method of embodiment 198, wherein the different concentrations of the test agent are tested serially.

201. The method of any one of embodiments 198 to 200, which further comprises determining the teratogenic concentration of a test agent that disrupts formation of the neural ectodermal lineage structure.

202. A screening platform for identifying an agent that is biologically active against a disease phenotype comprising:

(a) a first neural ectodermal lineage cellular structure according to any one of embodiments 151 to 174 whose mammalian cells comprise a genetic mutation associated with a disease, and (b) a second neural ectodermal lineage cellular structure according to any one of embodiments 151 to 174 whose mammalian cells lack the genetic mutation associated with the disease but are otherwise isogenic to the first neural ectodermal lineage cellular structure.

203. The platform of embodiment 202, wherein the genetic mutation is associated with a neurodegenerative disorder.

204. The platform of embodiment 203, wherein the neurodegenerative disorder is Huntington's disease.

205. The platform of embodiment 204, wherein the mammalian cells encode a Huntingtin protein with an expanded polyglutamine repeat.

206. The platform of embodiment 205, wherein the polyglutamine repeat has 42-150 glutamine residues.

Unless defined otherwise herein, all technical and scientific terms used herein have the same meaning as commonly understood by one of ordinary skill in the art. Various scientific dictionaries that include the terms included herein are well known and available to those in the art. Any methods and materials similar or equivalent to those described herein find use in the practice of the embodiments disclosed herein.

The terms defined immediately below are more fully understood by reference to the specification as a whole. The definitions are for the purpose of describing particular embodiments only and aiding in understanding the complex concepts described in this specification. They are not intended to limit the full scope of the disclosure. Specifically, it is to be understood that this disclosure is not limited to the particular sequences, compositions, algorithms, systems, methodology, protocols, and reagents described, as these may vary, depending upon the context they are used by those of skill in the art.

As used in this specification and appended claims, the singular forms "a" "an", and "the" include plural referents unless the content and context clearly dictates otherwise. Thus, for example, reference to "a device" includes a combination of two or more such devices, and the like.

Unless indicated otherwise, an "or" conjunction is intended to be used in its correct sense as a Boolean logical operator, encompassing both the selection of features in the alternative (A or B, where the selection of A is mutually exclusive from B) and the selection of features in conjunction (A or B, where both A and B are selected). In some places in the text, the term "and/or" is used for the same purpose, which shall not be construed to imply that "or" is used with reference to mutually exclusive alternatives.

Throughout this specification, quantities are defined by ranges, and by lower and upper boundaries of ranges. Each lower boundary can be combined with each upper boundary to define a range. The lower and upper boundaries should each be understood as a separate and independent element.

Additionally, any examples or illustrations given herein are not to be regarded in any way as restrictions on, limits to, or express definitions of any term or terms with which they are utilized. Instead, these examples or illustrations are to be regarded as being described with respect to one particular embodiment and as being illustrative only. Those of ordinary skill in the art will appreciate that any term or terms with which these examples or illustrations are utilized will encompass other embodiments which may or may not be given therewith or elsewhere in the specification and all such embodiments are intended to be included within the scope of that term or terms. Language designating such nonlimiting examples and illustrations includes, but is not limited to: "for example," "for instance," "e.g.," and "in one embodiment."

In this specification, groups of various parameters containing multiple members are described. Within a group of parameters, each member may be combined with any one or more of the other members to make additional sub-groups. For example, if the members of a group are a, b, c, d, and e, additional sub-groups specifically contemplated include any one, two, three, or four of the members, e.g., a and c; a, d, and e; b, c, d, and e; etc.

The invention may be better understood by reference to the following non-limiting Examples, which are provided as exemplary of the invention. The following examples are presented in order to more fully illustrate the various embodiments and the preferred embodiments of the invention and should in no way be construed, however, as limiting the broad scope of the invention.

Examples

Here, we reconstitute human neurulation in geometrically confined colonies, and induce the four ectodermal cell types with a spatial arrangement that mimics their embryonic counterpart. We characterize the cell types at the molecular level and identify human-specific signatures that are not previously discovered in other model systems. This enables a tractable model of human neurulation as well as early human developmental disorders. We demonstrate the translational relevance of our platform by demonstrating that a complex neurodegenerative disease such as Huntington's disease (HD) can be modeled with high accuracy and reproducibility over hundreds of HD-neuruloids isogenic replicates. Specific phenotypic signatures provide a unique opportunity to understand the neuropathology underlying HD as well as a robust platform which allows a rational approach to drug screens.

Results

Formation of Standardized Human Neural Telencephalic Structures

Figure 1:
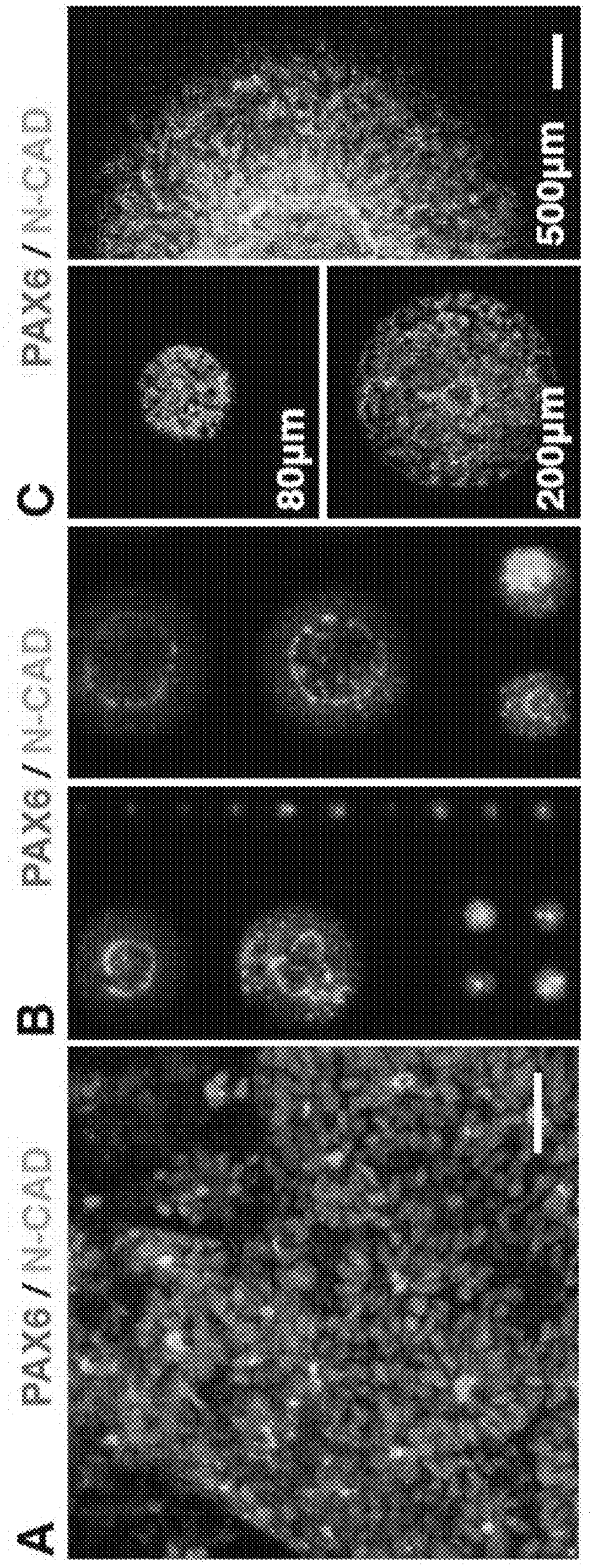
FIG. 1 depicts self-organization in neural rosettes on micropatterns. (A) Day 19 neural rosettes in a monolayer differentiation protocol. (B) Micropatterned culture after 7 days with SB+LDN treatment. Colonies of the following diameters are shown: 80, 200, 500, 800, and 1000 μm. (C) Immunofluorescence analysis of 80, 200, and 500 pum of day 7 micropatterned colonies. Samples were stained with the neural differentiation marker PAX6 (green) and neural adhesion protein N-cadherin (N-CAD, orange), (D) Three-dimensional analysis of 200 jm colony at day 7. (Top) Top view of DAPI and N-CAD staining with 64-z projected images. (Bottom) Side view with re-sliced z-stack around N-CAD-+ center region. (E) Comparison of the lumen closure in single colonies of 200 μm and 500 μm at day 7. (F) Immunofluorescence analysis of 200 μm micropatterned colonies at day 7. Samples were stained with PAX6 (green), OTX2 (red), and LIX2 (orange). (G) Illustration of a human embryo (Carnegie stage 12: week 4, n.5923) with the telencephalon population highlighted. The two stages represent a lower and upper bound in developmental time corresponding to the neuruloid. (H) Time course analysis of the micropatterned culture. Immunofluorescence imaging of 200 μm colonies treated with SB+LDN from day 1 to 7 with PAX6 (green), pluripotency marker OCT4 (red) and N-CAD (orange). (I) (Top) Quantifications of mean PAX6 and OCT4 intensities in single colonies from day 1 to 7 (n>10). (Bottom) Quantifications ofrmean N-CAD+ lumen diameters from day 1 to 7 (n>10), (J) Quantitative PCR analysis of various lineage-specific genes from day 1 to 7 of the micropatterned culture. All scale bars represent 50 μm.
Figure 1:
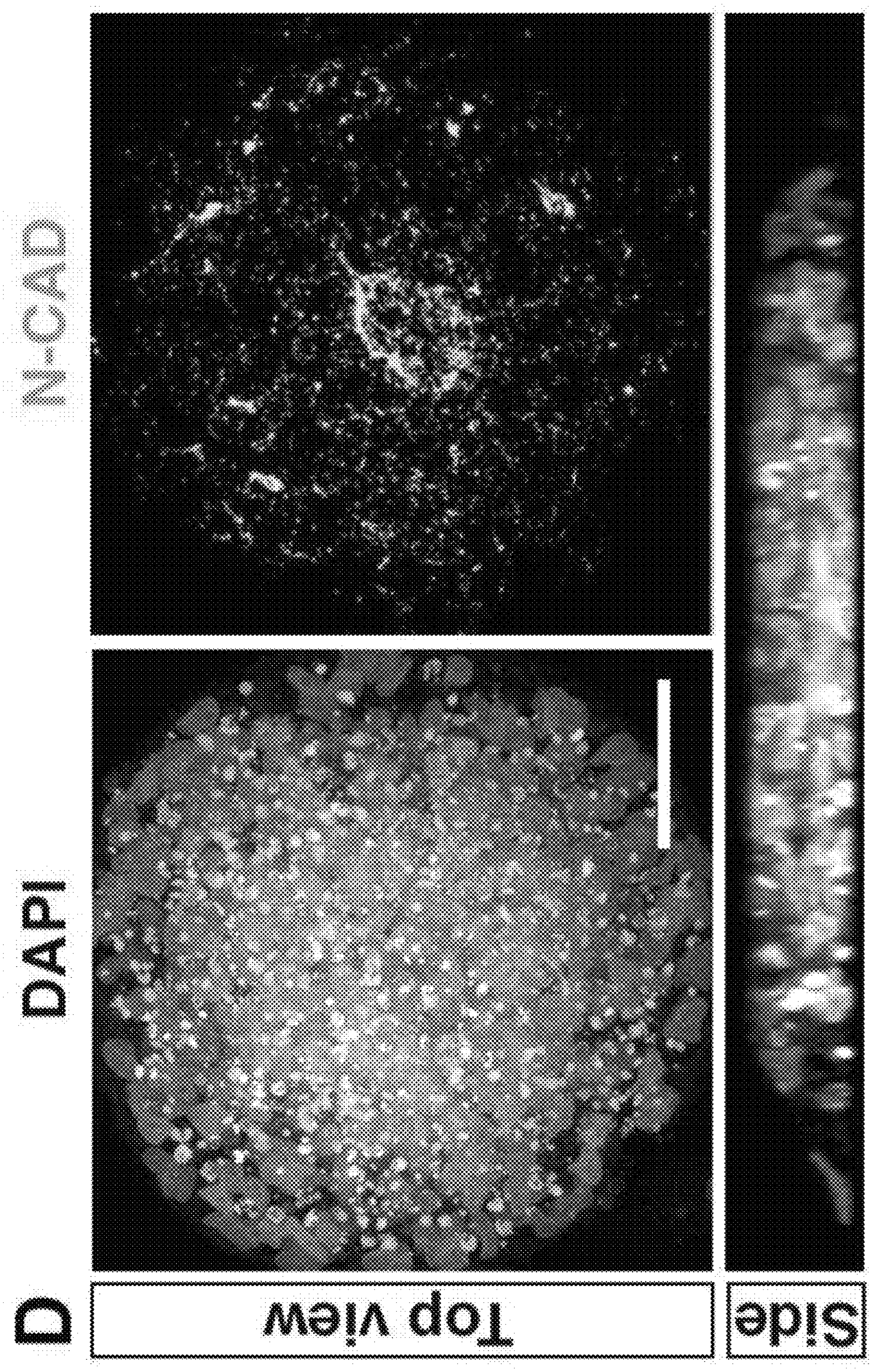
Figure 1:
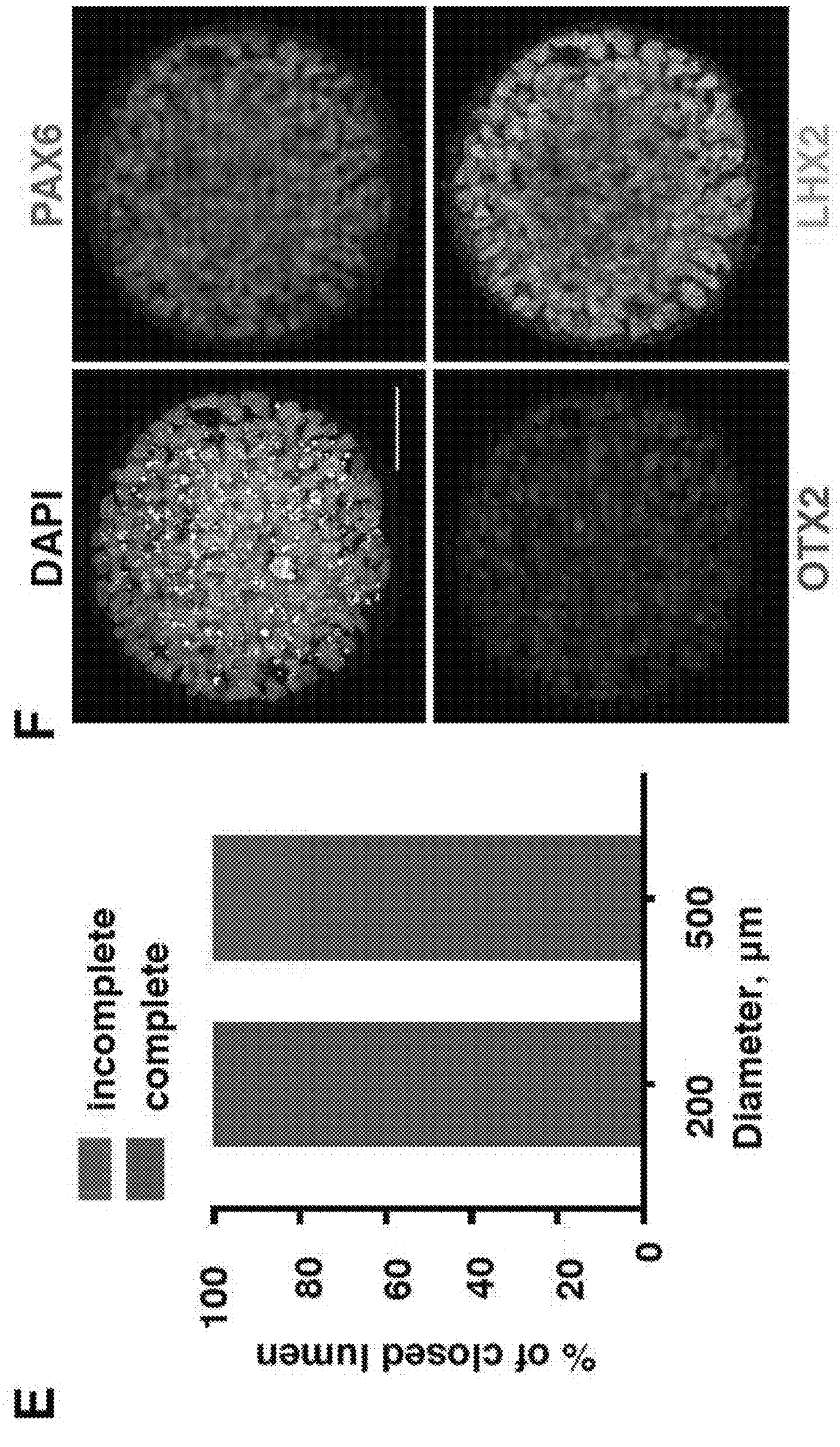
Figure 1:
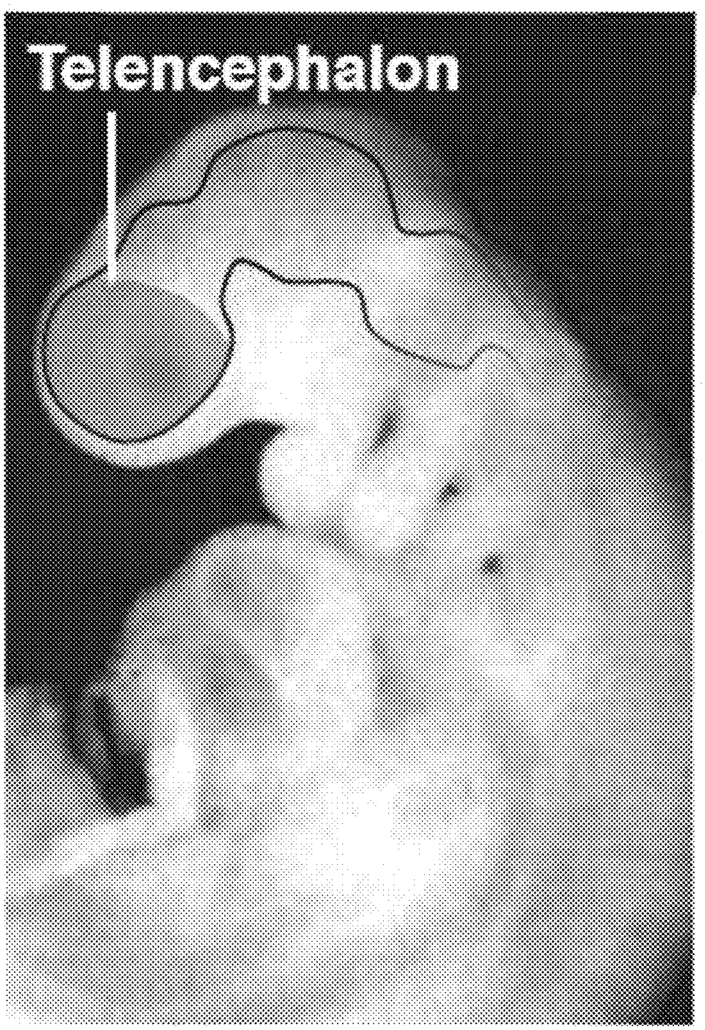
Figure 1:
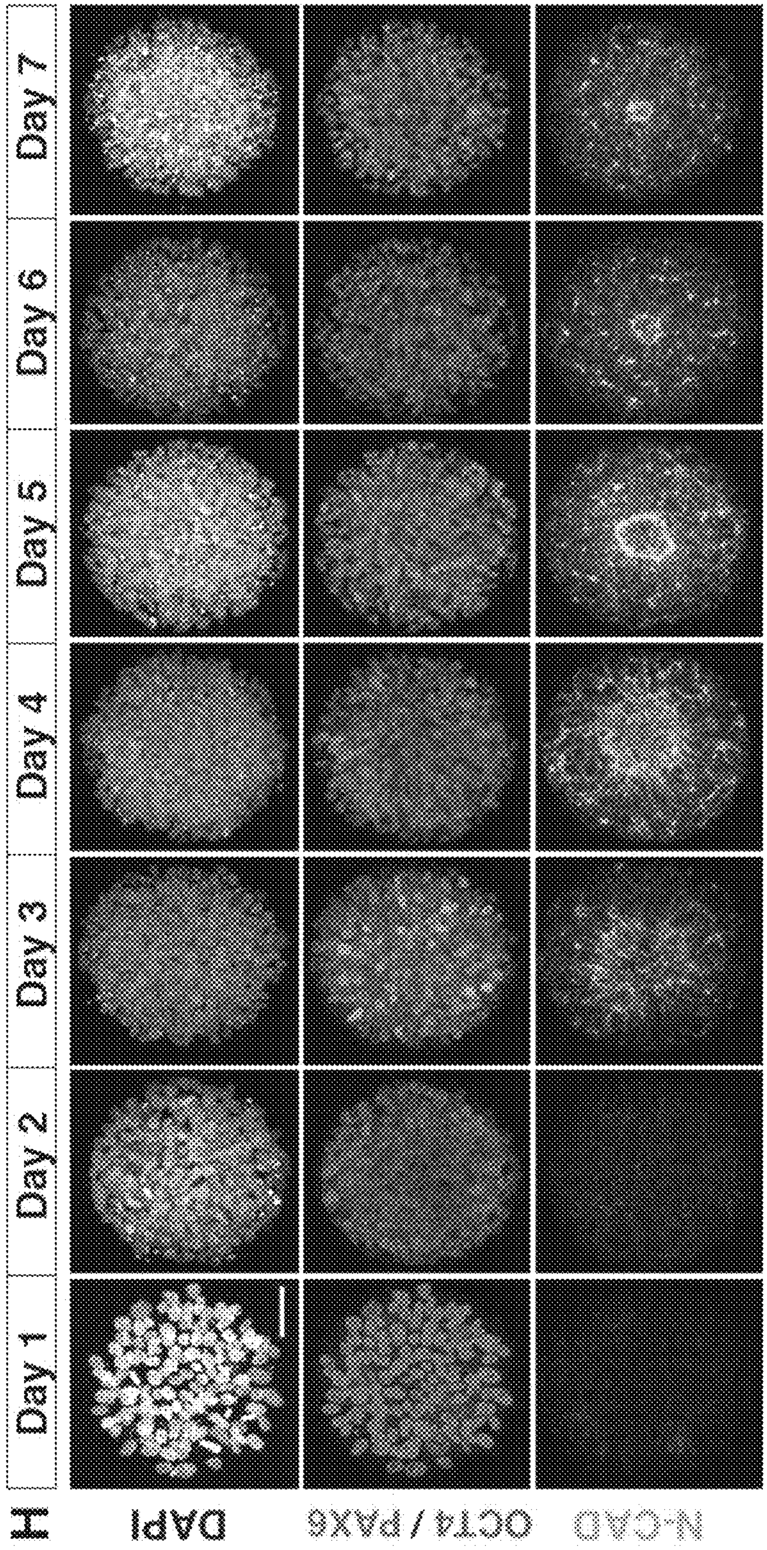
Figure 1:
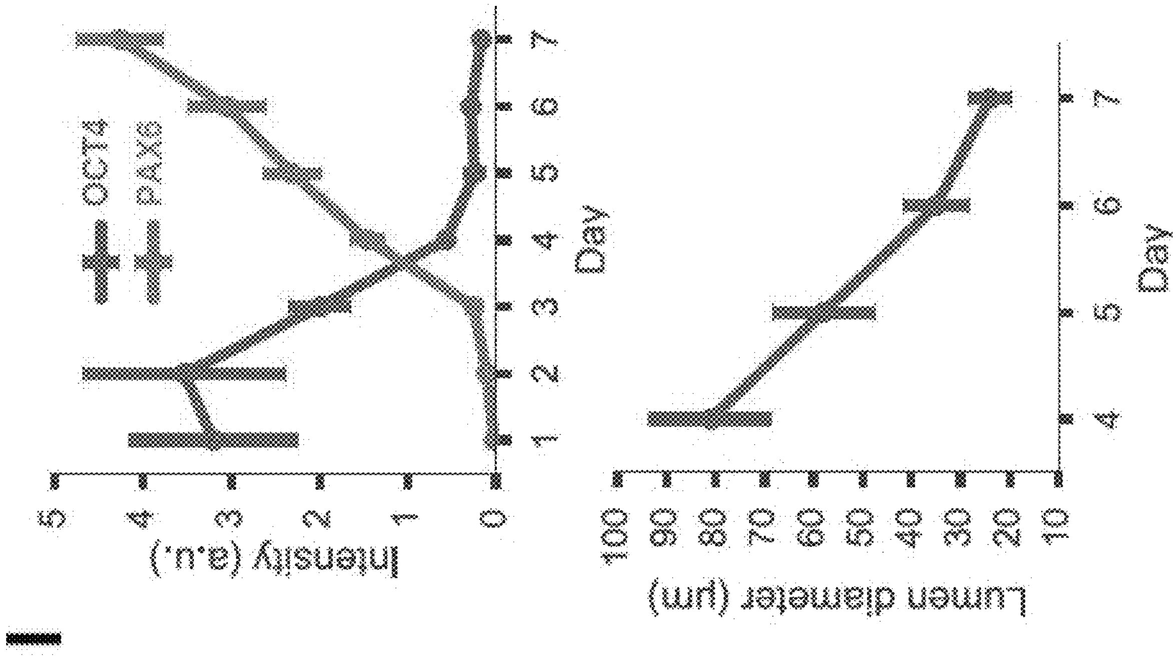
Figure 1:
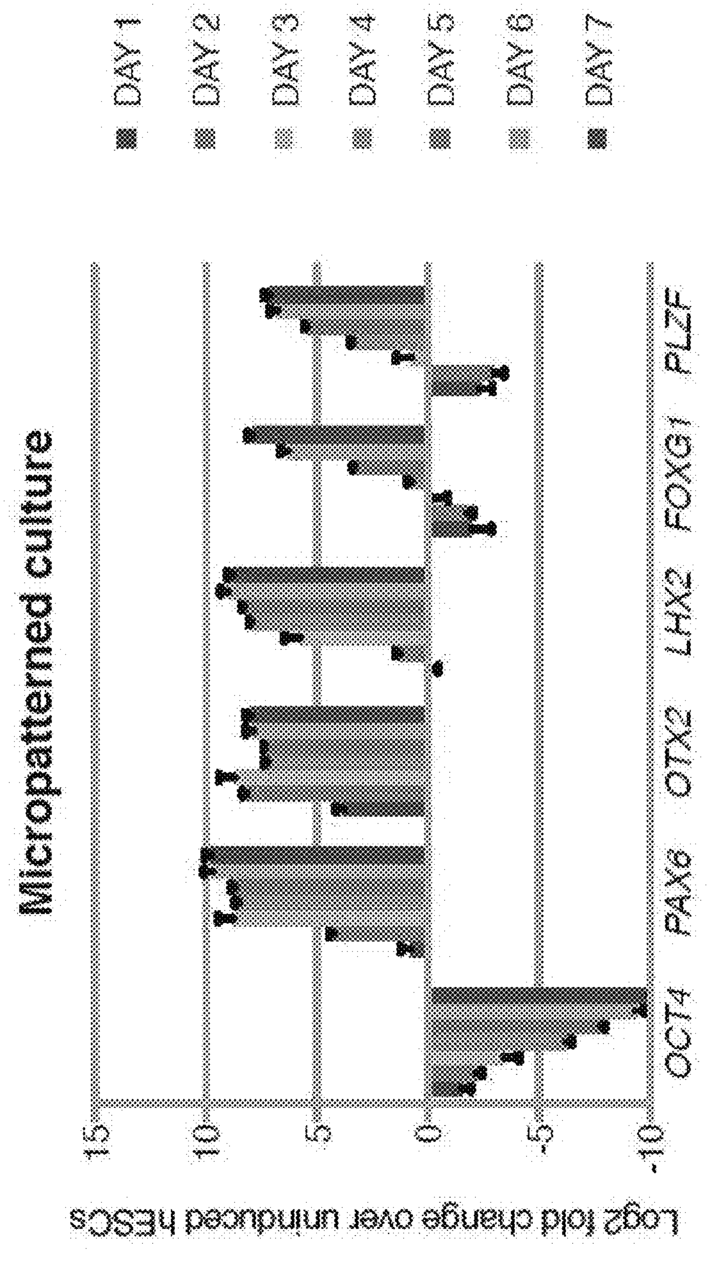

Neural induction in regular culture dishes leads to the formation of neural rosettes with groups of PAX6+ cells, radially organized towards an N-CADHERIN (N-CAD) center (FIG. 1A). However, rosette generation suffers from random cell numbers, geometries and distributions, preventing precise mechanistic studies.

Figure 7:
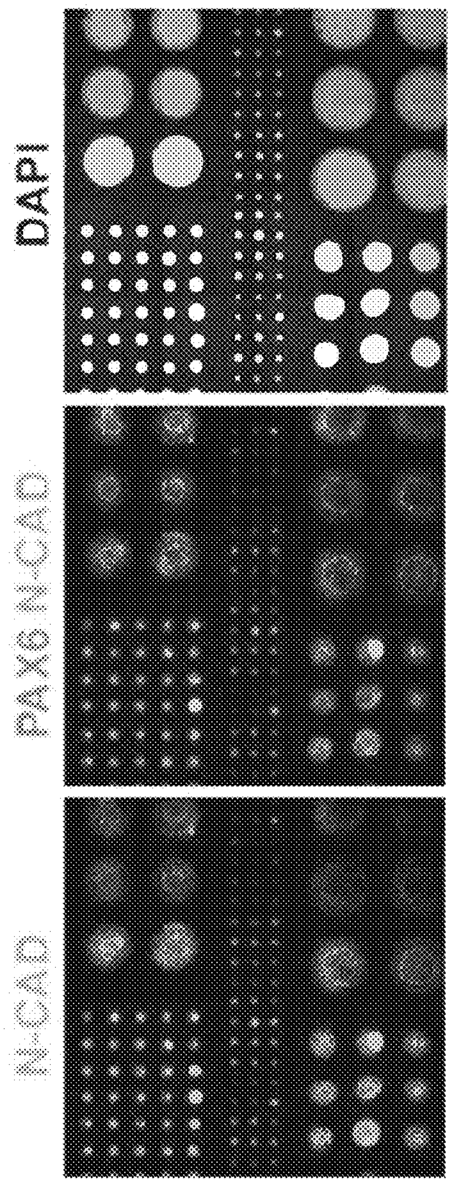
FIG. 7—related to FIG. 1 (A) Day 7 micropatterned culture after 7 days with SB+LDN. Colonies of the following diameters are shown: 80, 200, 500, 800, and 1000 μm. Samples were stained with DAPI (gray), the neural differentiation marker PAX6 (green), and neural adhesion protein N-cadherin (N-CAD, orange). (B) Representative immunofluorescence images of PAX6 and N-CAD at day 7 of 200 and 500 μm micropatterned culture with multiple z from bottom to top. (C) Representative immunofluorescence images of atypical protein kinase C (aPKC), partitioning defective 3 (PAR3) at day 7 of 200 and 500 μm micropatterned culture with multiple z from bottom to top. (D) Representative immunofluorescence images of 80, 200, 500, and 1000 μm of day 7 micropatterned colonies by PAX6 (green) and N-CAD (orange) with 3 different initial cell seeding number: 0.38, 0.50, and 0.64 million cells. (Right) Quantification of lumen size at different initial seeding densities. N-CAD+ lumen sizes of 200 μm colonies are shown as a ratio of inner lumen area to colony area (n>80). Data are mean±standard deviation.
Figure 7:
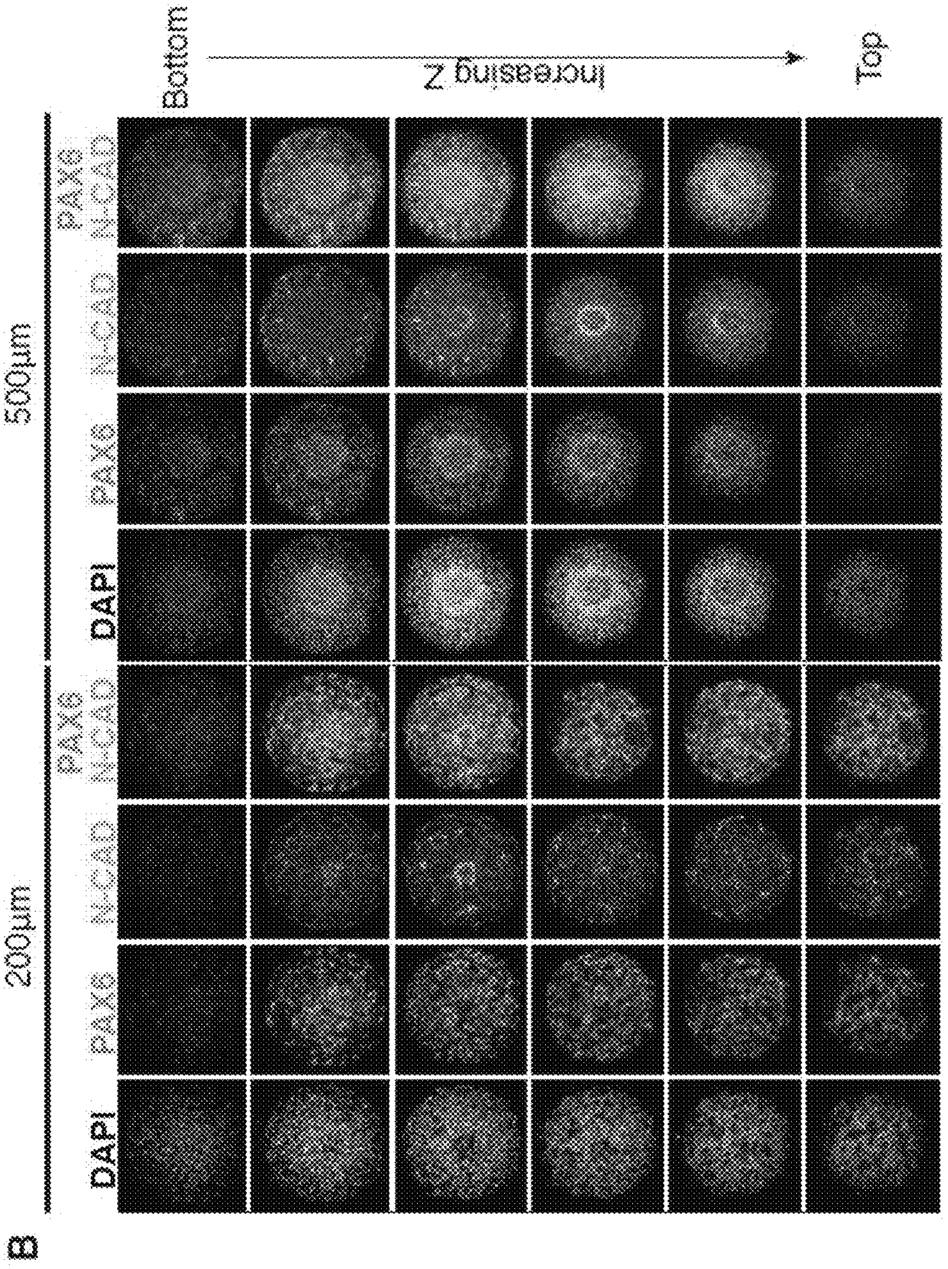
Figure 7:
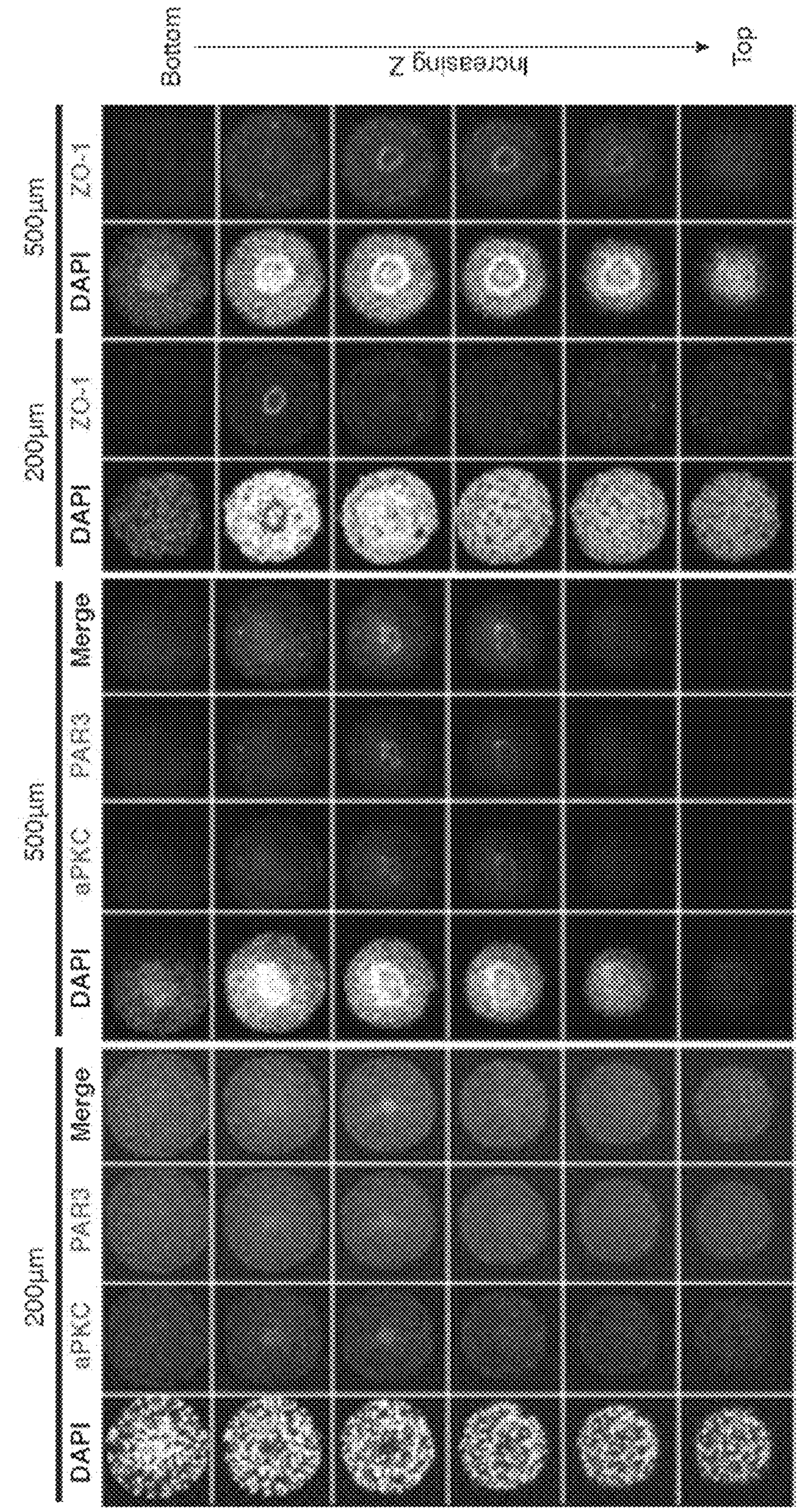
Figure 7:
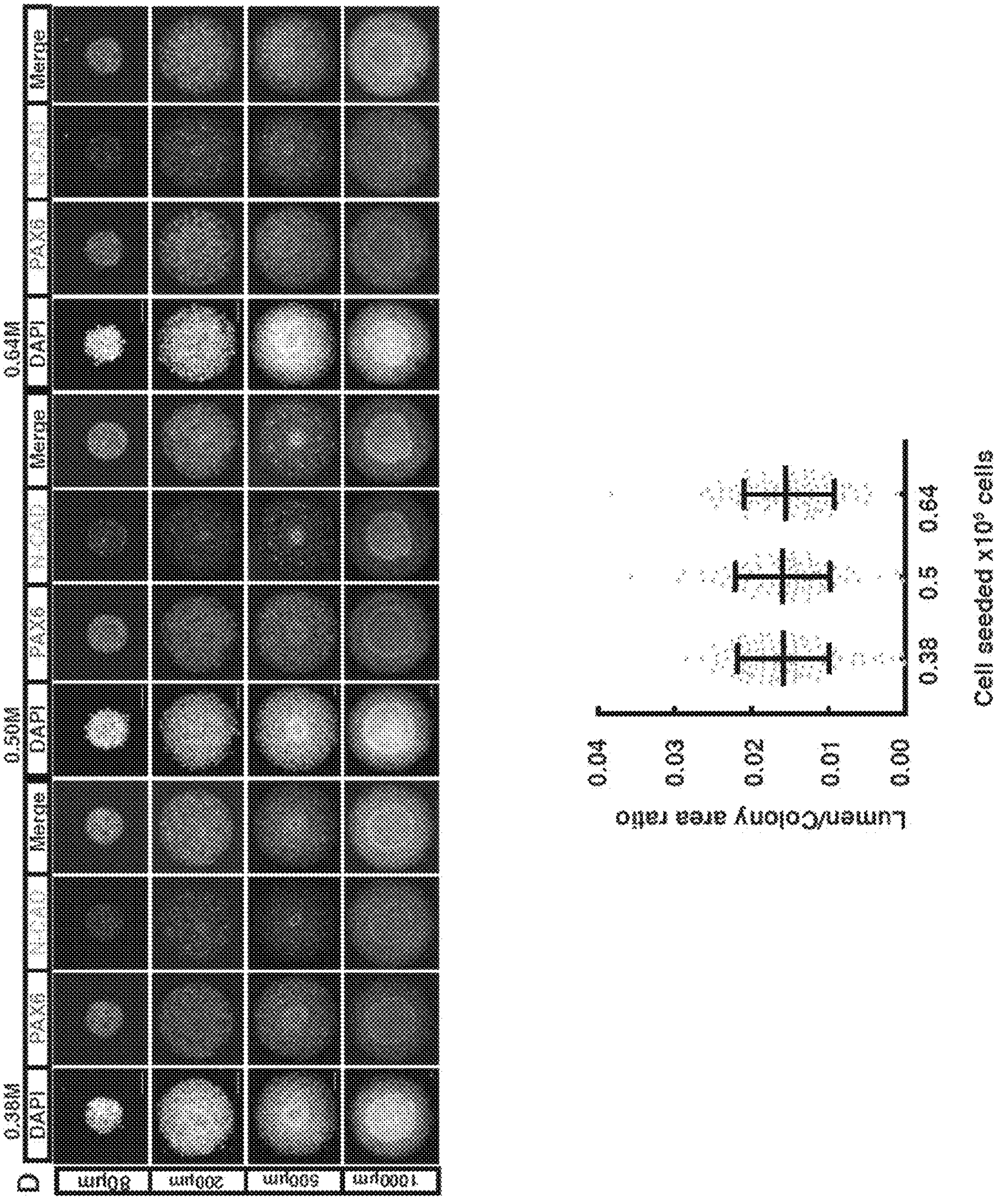

Pluripotent hESCs (RUES2) were seeded on circular micropattern substrates from 80 μm to 500 μm diameters, and treated with SB431542 (SB) and LDN 193189 (LDN) for 7 days to induce neural fate. After 7 days, regardless of the size, all cells had converted to PAX6+ neuronal progenitors with N-CAD expression in the center of each colony (FIG. 1B and FIG. 7A). Self-organization was size-dependent, and colonies smaller than 200 μm did not display any radial organization (FIG. 1C). Cell polarization was observed in 200 μm neural colonies towards a central lumen, delineated by expression of the apical markers N-CAD/PAR3/aPKC/ZO1 (FIG. 1D and FIG. 7B-7C). 200 μm neural colonies, displayed robust and complete closure of a single lumen with constant size, which was independent of initial cell density (FIG. 1E and FIG. 7D). Conversely, 500 μm colonies often displayed an open central cavity and peripheral foci of N-CAD expression (FIG. 1E and FIG. 8A-D). The cells were of anterior telencephalic identity as they expressed OTX2 and LHX2 (FIG. 1F). L HX2 expression in mice is first detected at E8 in the optic vesicle at low levels and later, E10-11, in the telencephalon which corresponds to days 17-19 and 24-30 in human development, respectively (FIG. 1G, informatics.jax.org). Interestingly, it was found that fate acquisition occurred with similar dynamics in micropatterns and in regular culture dishes, while self-organization into rosette structures was accelerated by geometrical confinement (FIG. 11H-J and FIG. 8E). Thus self-organization is, at this stage, independent of fate acquisition. Moreover, the 200 μm colonies provide a standardized and highly robust platform to investigate quantitatively and with sub-cellular resolution the earliest processes of human neural induction and morphogenesis in vitro.

Self-Organization of all Human Ectodermal Lineages: Neuruloids

Figure 2:
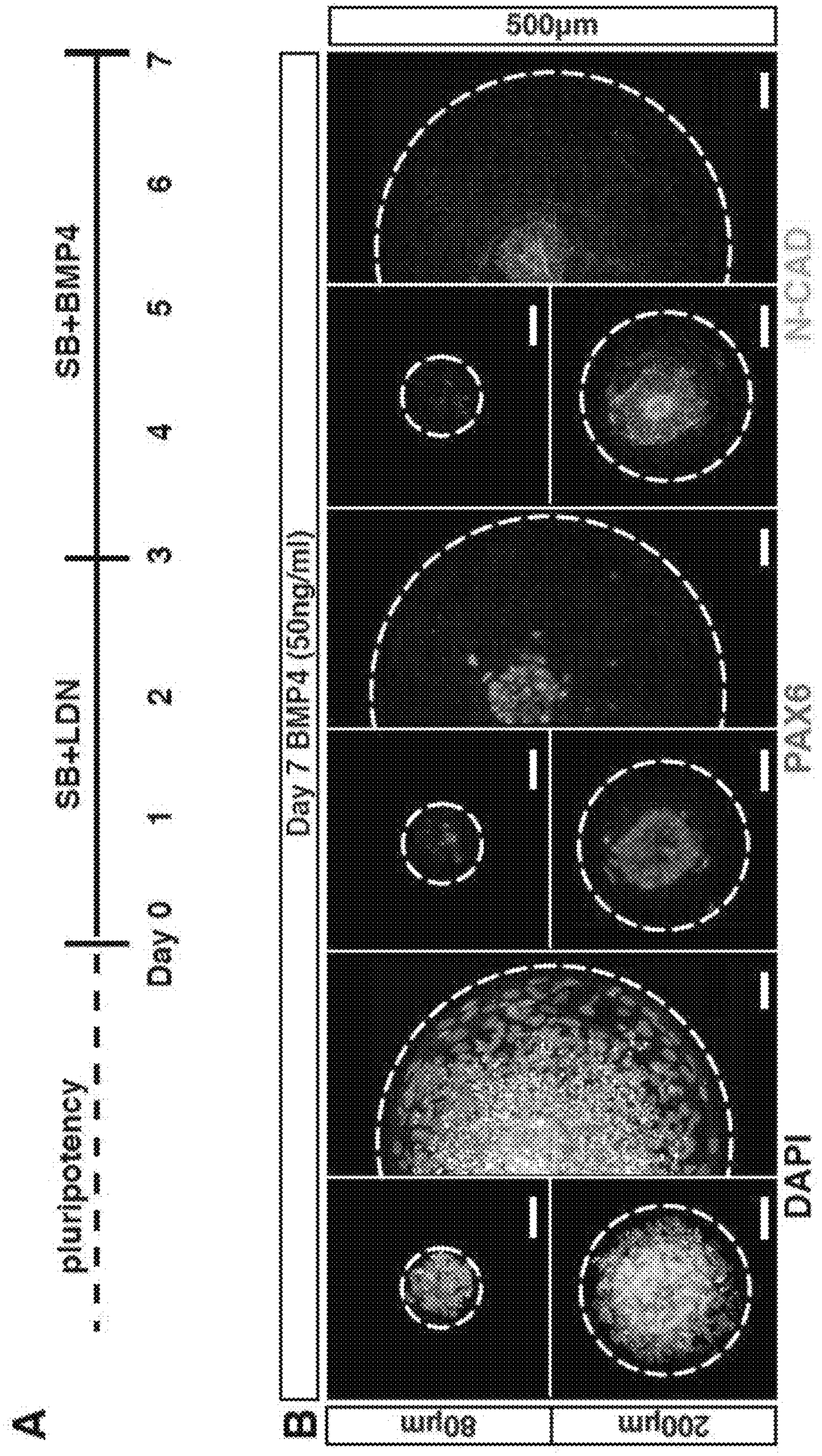
FIG. 2 depicts self-organization into neuruloids on micropatterns. (A) Schematic of the neuruloid differentiation protocol. (B) Immunofluorescence imaging of 80, 200 and 500 μm of day 7 micropatterned colonies. Samples were stained with DAPI (gray), PAX6 (green), and N-CAD (orange). (C) Immunofluorescence imaging of 500 μm of day 7 micropatterned colonies. Samples were stained with DAPI (gray), PAX6 (green), and COL4 (Collagen IV, orange). Side view of resliced z-stack around PAX6+ center region, colony edge region is also shown. (D) replicates with PAX6 (green) and SOX10 (red). (E) (Left) Immunofluorescence imaging of 500 μm micropatterned colonies at day 7 with different BMP4 concentrations: 0, 3, 13, and 50 ng/ml. Samples were stained with PAX6 (green), SOX10 (red) and cranial placode marker SIX (orange), (Right) Quantifications of SIX1 positive cell number. Data are mean standard deviation. (F) (Top Left) Sketch of the ectodermal compartment at neurulation in vivo. (Top Right) Sketch of the neuruloid on micropattern. (Middle panel) Side view of the day 7 neuruloid with 3 ng/ml of BMP. Samples were stained with DAPI, PAX6, SOX10, SIX1, and non-neural ectoderm maker TFAP2A. Note that the TFAP2A+ also stain a few SOX10 and SIX1 positive cells. The non-neural ectoderm cells are only TFAP2A positive. (Bottom) Top view by multiple z from bottom to top. All scale bars represent 50 μm.
Figure 2:
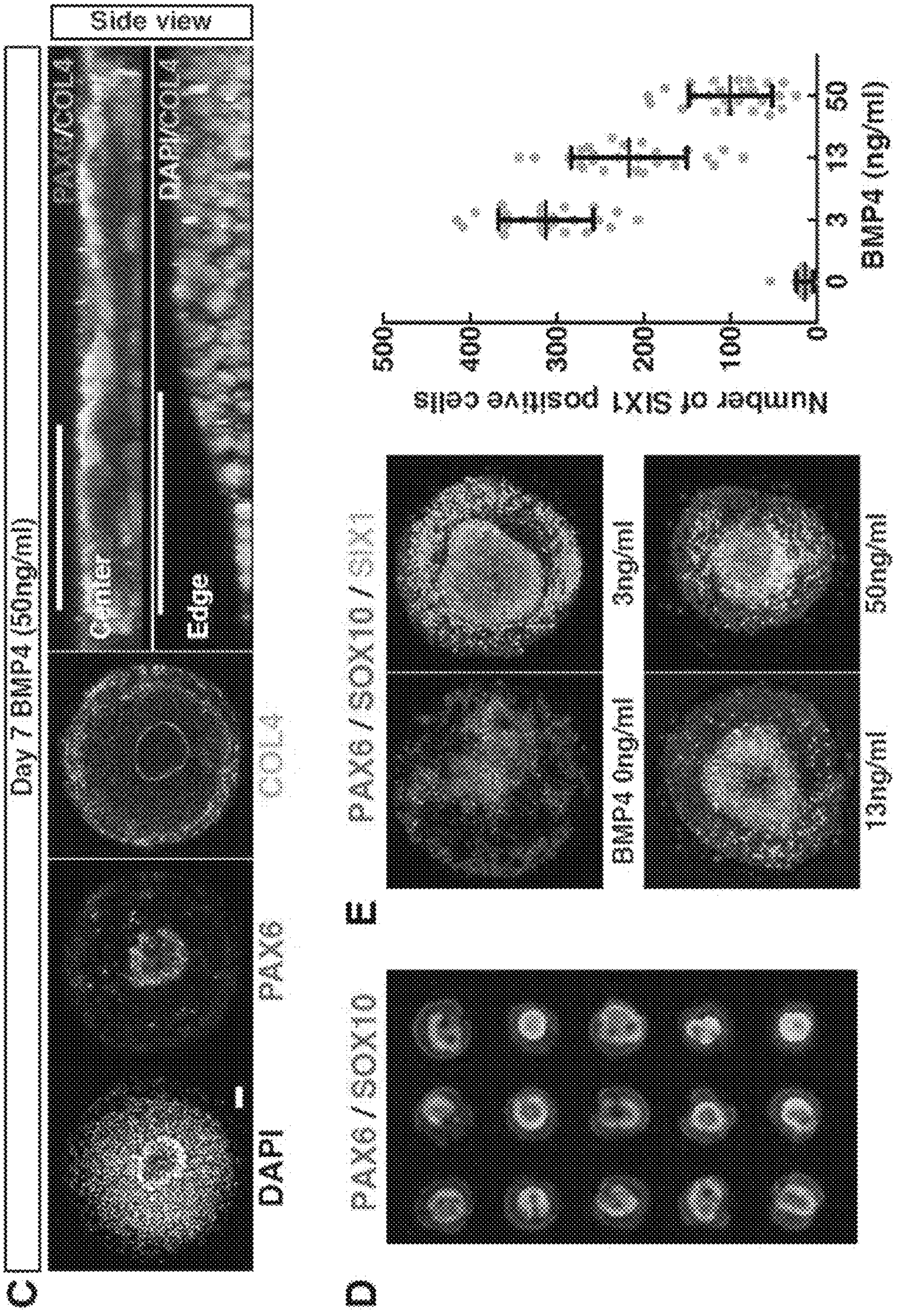
Figure 2:
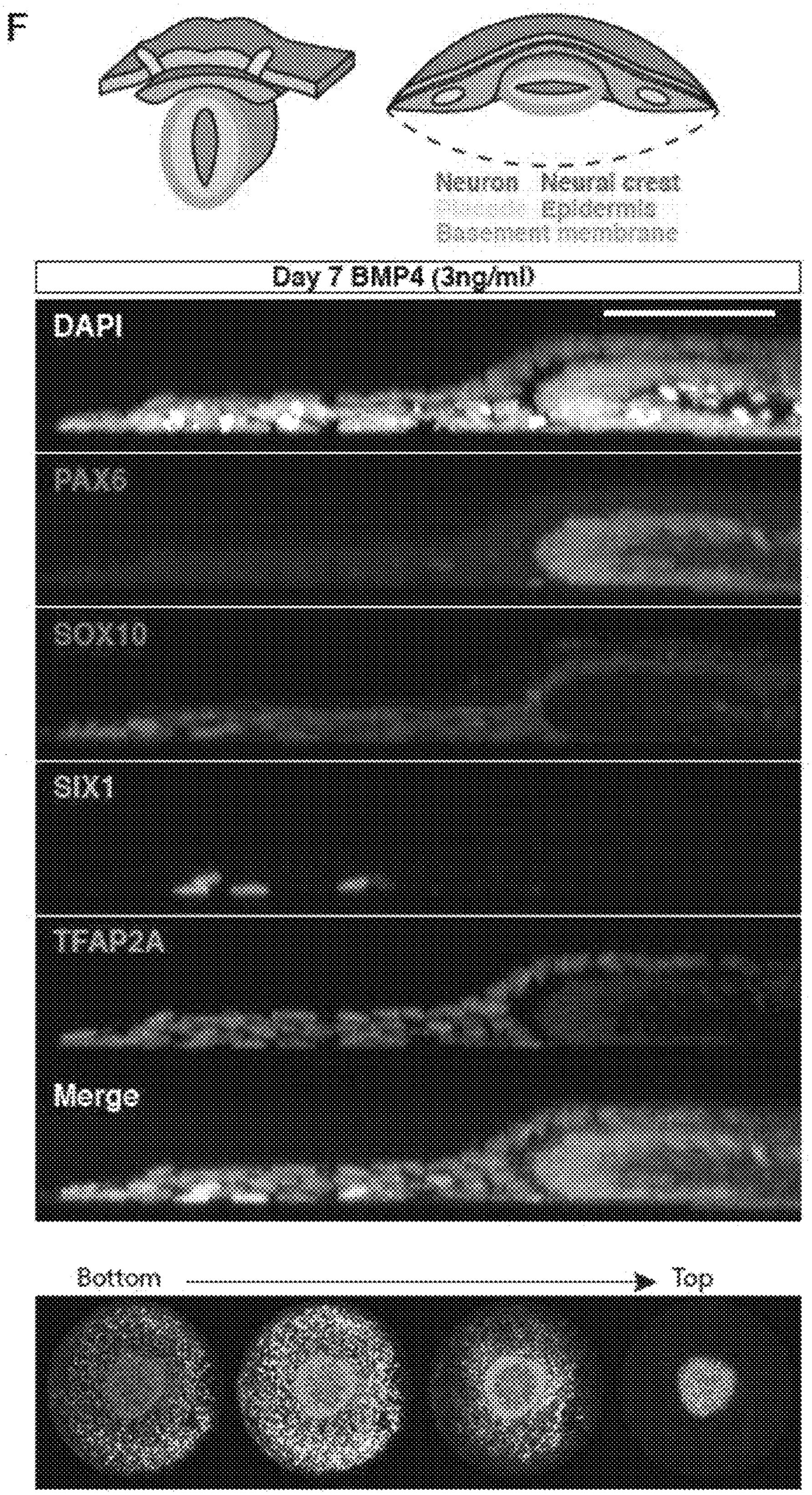
Figure 8:
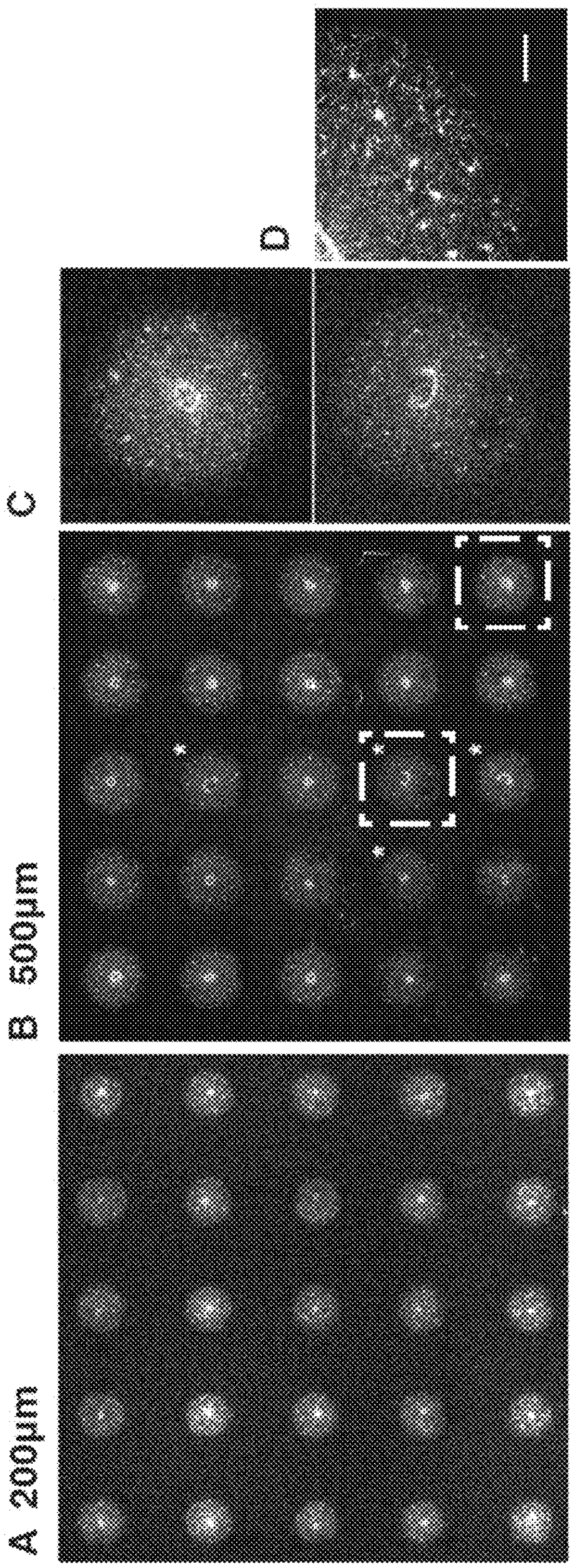
FIG. 8—related to FIGS. 1 and 2 (A) Representative immunofluorescence images of day 7 micropatterned colonies of 200 and (B) 500 μm stained with N-CAD. Stars indicate the micropatterns with incomplete lumen. (C) Representative images of the complete (above) and the incomplete (bottom) lumen in 500 μm micropatterned colonies. (D) Representative images of the satellite N-CAD+ loci in 500 μm colony. (E) Representative immunofluorescence images of the monolayer differentiation protocol from day 1 to 6 with PAX6 (green), OCT4 (red) and N-CAD (orange). (Right) Quantitative PCR of various lineage-specific genes from day 1 to 7 of monolayer culture. (F) Side view by resliced z-stack around N-CAD+ center region of day 7 micropatterned colonies (BMP4 50 ng/ml) of 80, 200, and 500 μm. Samples were stained by DAPI (gray), PAX6 (green), and N-CAD (orange). (G) Immunofluorescence analysis of 500 μm micropatterned colonies differentiated by BMP4 (50 ng/ml) as well as BMP4 (3 ng/ml) protocol. Samples were stained with DAPI (gray), PAX6 (green), neural crest marker SOX10 (red), and cranial placode marker SIX1 (orange). (H) Immunofluorescence analysis of 500 μm micropatterned colonies at day 7 with different BMP4 concentrations: 0, 3, 13, and 50 ng/ml. SIX1 expression is shown within 25 patterns for comparison of the four different conditions. (I) Radially averaged marker expression from 3 different colonies show the TFAP2A+ only cells covering the full surface of the colony. (J) Day 7 neuruloid showing a similar structure to FIG. 2E when using a different hESC line (RUES1) by immunofluorescence analysis of a 500 μm micropatterned colony with PAX6 (green), SOX10 (red), and SIX1 (orange).
Figure 8:
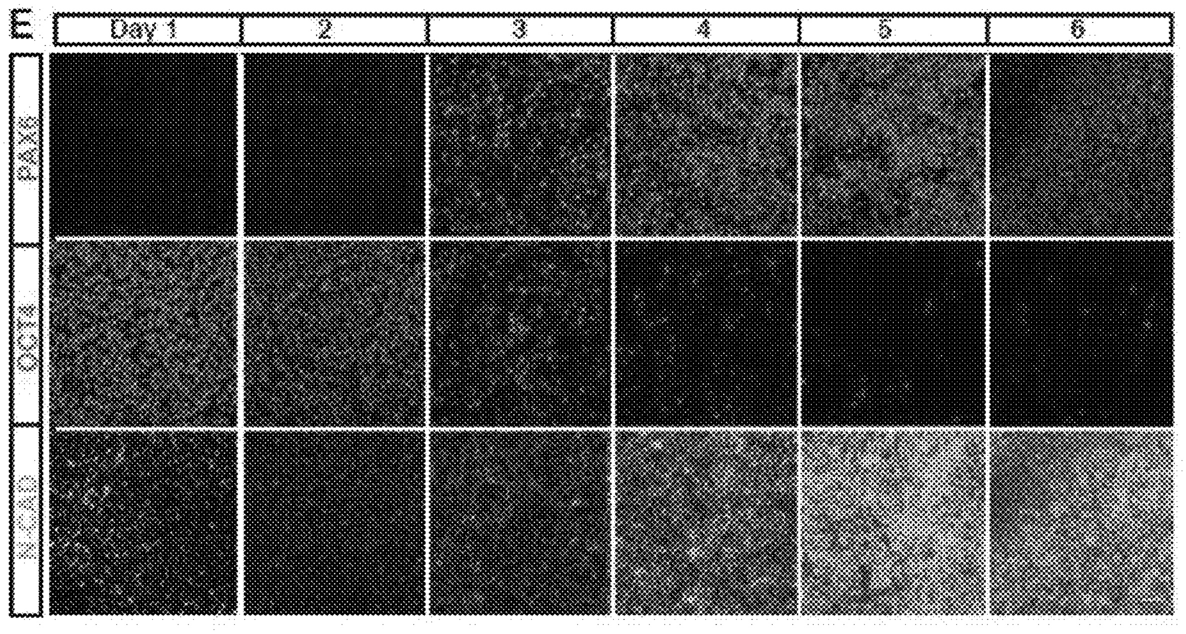
Figure 8:
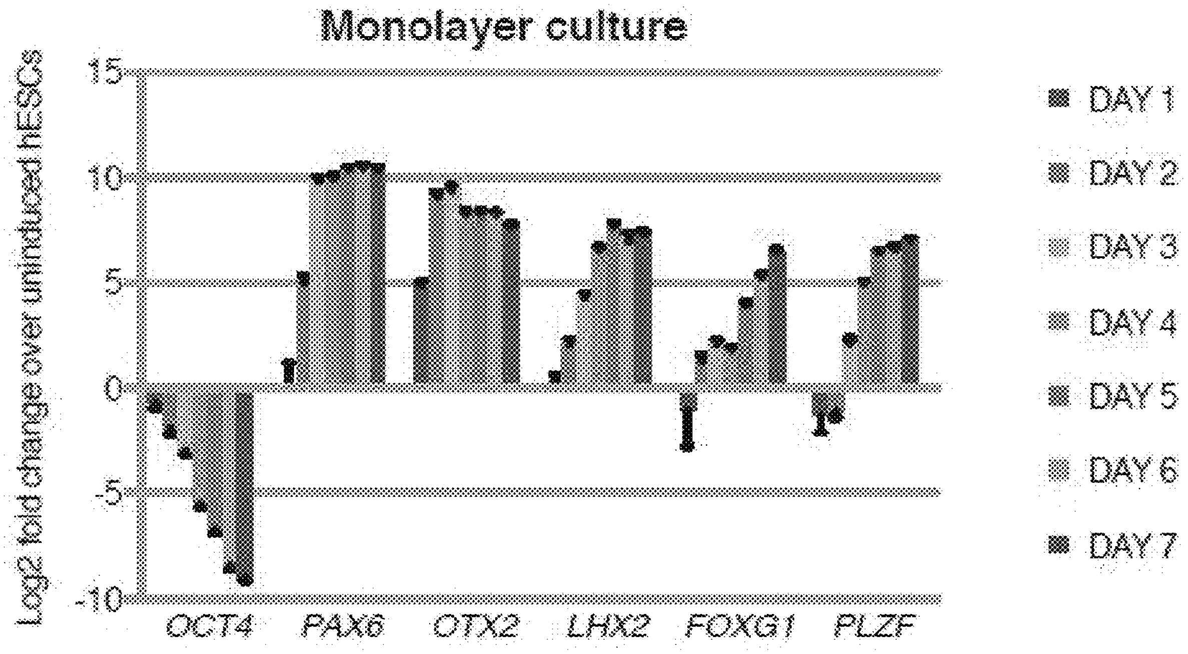
Figure 8:
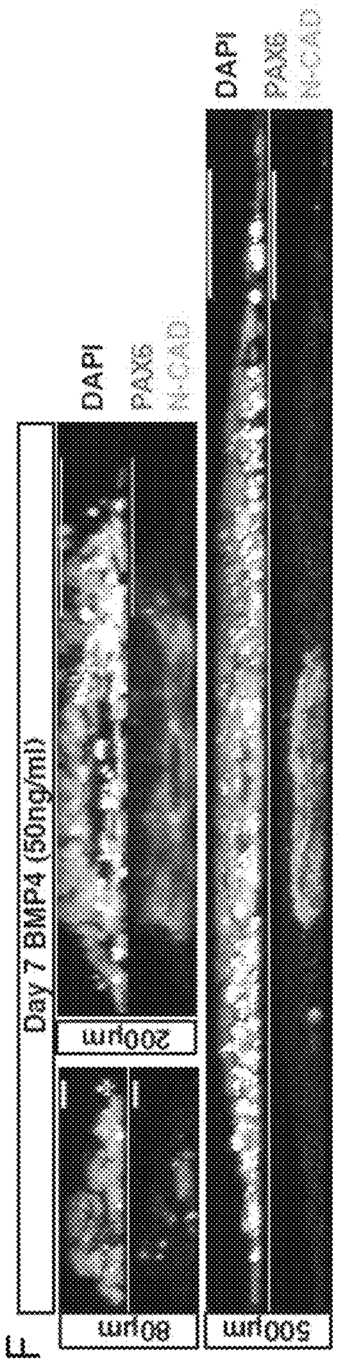
Figure 8:
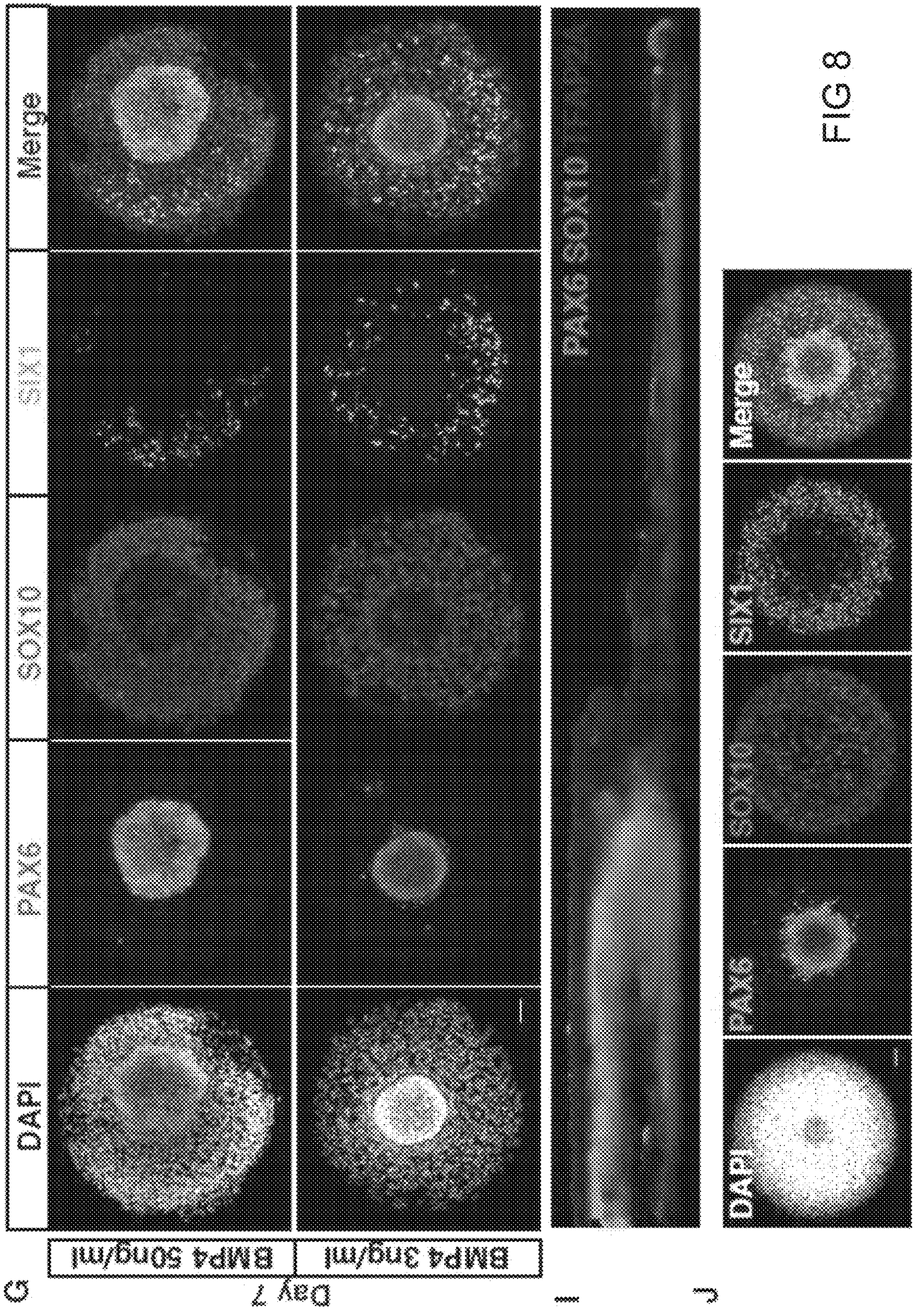
Figure 8:
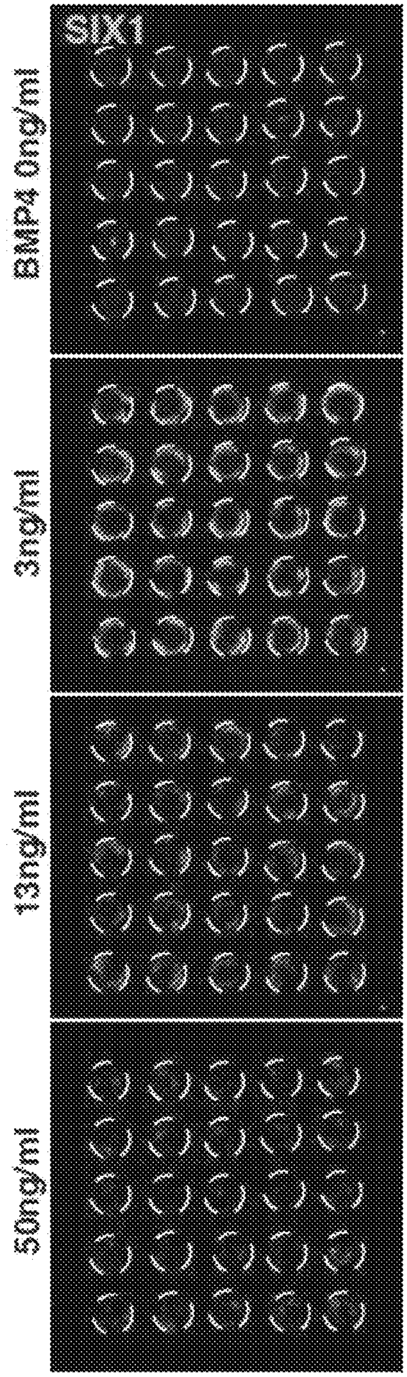

Induction of self-organization and spatial segregation of not only one, but all four ectodermal fates that emerge during neurulation in vivo: neural progenitors, placodes, neural crest and epidermis was tested. Cells were seeded under the same conditions, except that, after 3 days, LDN was removed and replaced with different concentrations of BMP4, to mimic graded BMP activity at the neural plate border as observed in model systems (8) (FIG. 2A). At high BMP4 concentrations, self-organization occurs in colonies of 200 μm and 500 μm, with a sub-population of PAX6+ cells at the center surrounding an N-CAD+ lumen (FIG. 2B). In a striking parallel with the in vivo situation, Collagen IV, which delineates the basal side of the neural tube, was also observed in the outer edge of the central PAX6+ population (FIG. 2C). The observation of PAX6− cells at the periphery suggested the presence of other non-neuronal fates (FIG. 2B-C, FIG. 8F). Directly adjacent to the PAX6+ cells, observation of dozens of replicates revealed radially symmetric patterns of SOX10 expressing cells around the PAX6 center, demonstrating the induction and self-organization of neural crest fates (FIG. 2D and FIG. 8G). Within the SOX10 domain, a salt and pepper distribution of SIX1±cells was observed (FIG. 2E). While the overall spatial distribution of cell types was independent of BMP4 concentration, the number of SIX1+ cells peaked at intermediate levels (FIG. 2E and FIG. 8H). Finally, the full structure was tri-dimensional and covered with a layer of TFAP2A+ cells, indicating the presence of a prospective epidermis (FIG. 2F and FIG. 8I). This was independent of the cell type, since the same result was observed using a different hESC line (RUES1, FIG. 8J). Overall, this self-organized structure is reminiscent of the ectodermal organization observed in vivo at neurulation stages (FIG. 2F), both in terms of cell populations, with the four main ectodermal derivatives present, and in terms of morphology, with the correct relative arrangement of the cell types. The structures were therefore coined these structures: neuruloids.

Single-Cell Molecular Characterization of the Neuruloids

Figure 3:
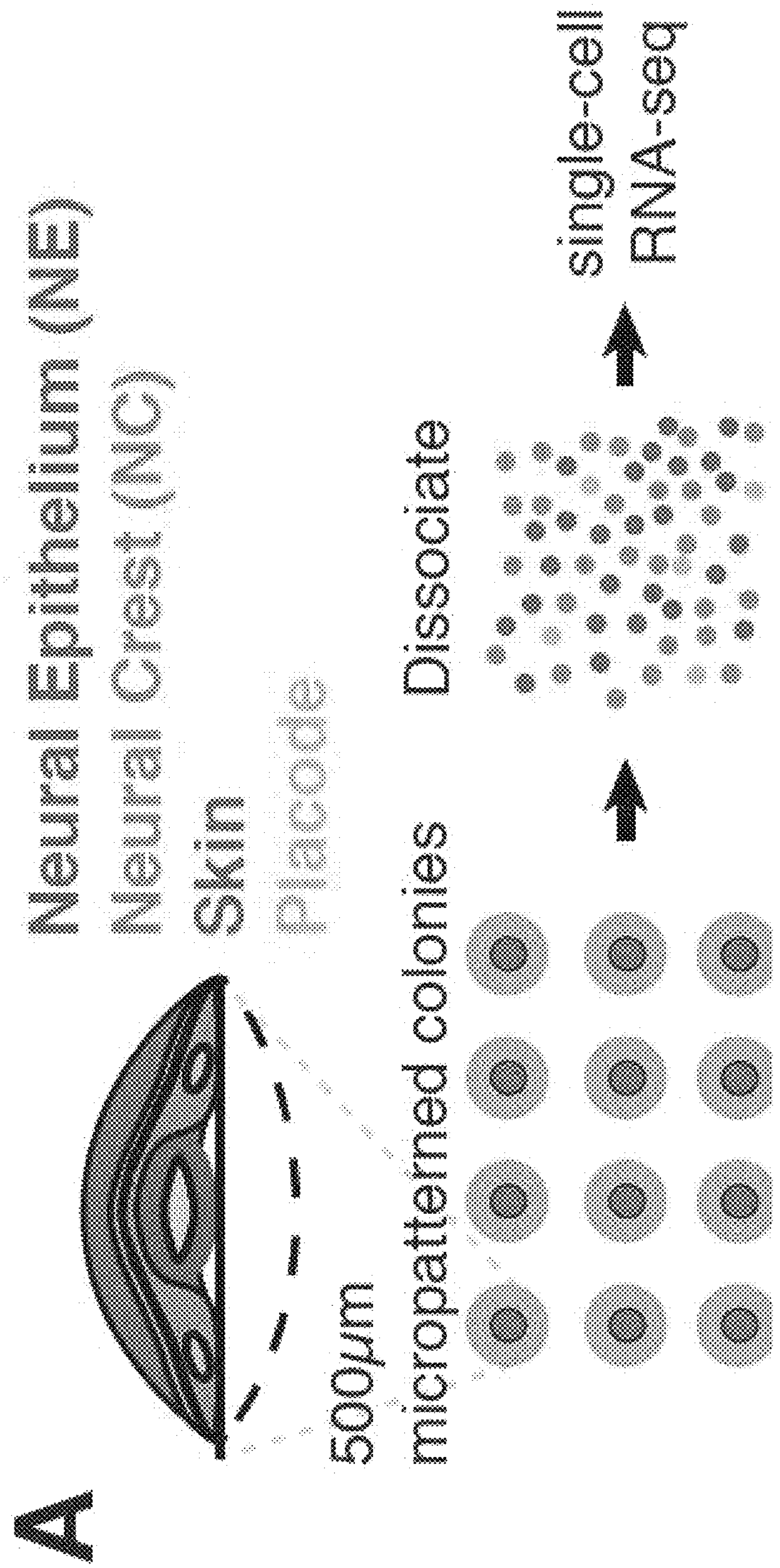
FIG. 3 depicts molecular characterization of neuruloid cell populations by single-cell RNA sequencing. (A) Experimental workflow: single-cell transcriptomes were collected from day 7 neuruloid using 3 ng/mL of BMP4. Micropatterned colonies with 500 μm diameter were lifted off a chip, dissociated to single-cell suspensions and scRNA-seq performed using the 10× Genomics platform. (B) t-SNE plots based on high-variance genes (see Methods) where each dot represents a single-cell. Each plot shows mRNA expression for the immunofluorescence markers used to characterize the spatial self-organization of the neuruloid in FIG. 2. PAX6+ neural populations (green) appear on the left side of the plot while the SOX10+ neural crest cells locate to the right (red). (C) t-SNE plot highlighting the main populations of the neuruloid: Neural Epithelium (NE1 and NE2, in green), Neural Crest (NC, in red), Placode (in orange), dividing cells (in grey), prospective epidermis (Skin, in blue) and early neurons (in cyan). (D) Single-cell gene expression levels of several key marker genes of each ectodermal population. Beeswarm plots showing the distribution of expression values are overlaid with boxplots delineating the median and the 25% and 75% percentiles. (E) t-SNE plot zoom on the SIX1+ cell population showing markers of neurogenic sensory placodal population in the neuruloid. (F) Immunofluorescence validation of early epidermal markers GATA3 and KRT18. (G) Illustration of a human embryo at neural tube closure stages (Kyoto n.33222 and Carnegie n.5923) with the anterior cranial populations captured by the neuruloid highlighted. The two stages represent a lower and upper bound in developmental time corresponding to the neuruloid.
Figure 3:
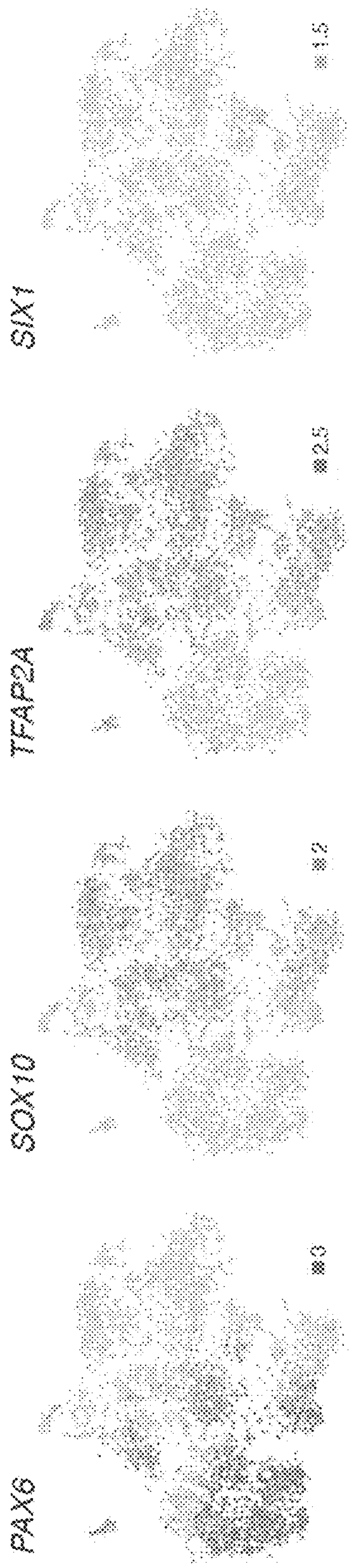
Figure 3:
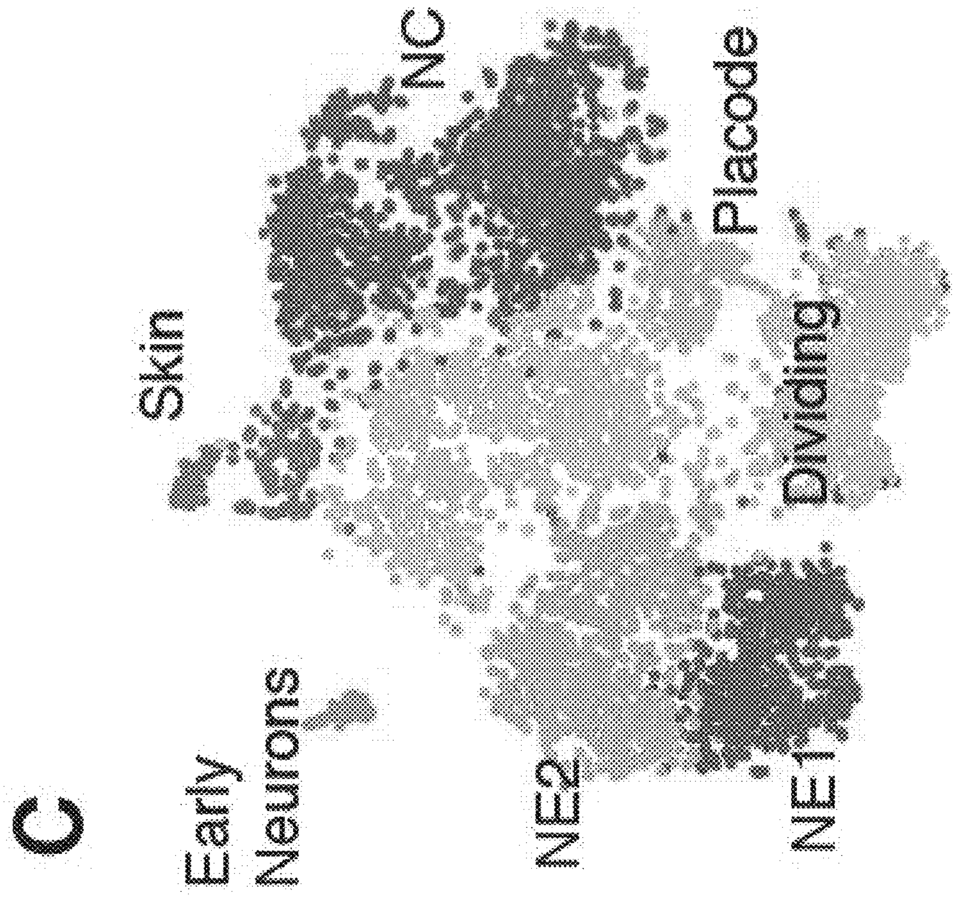
Figure 3:
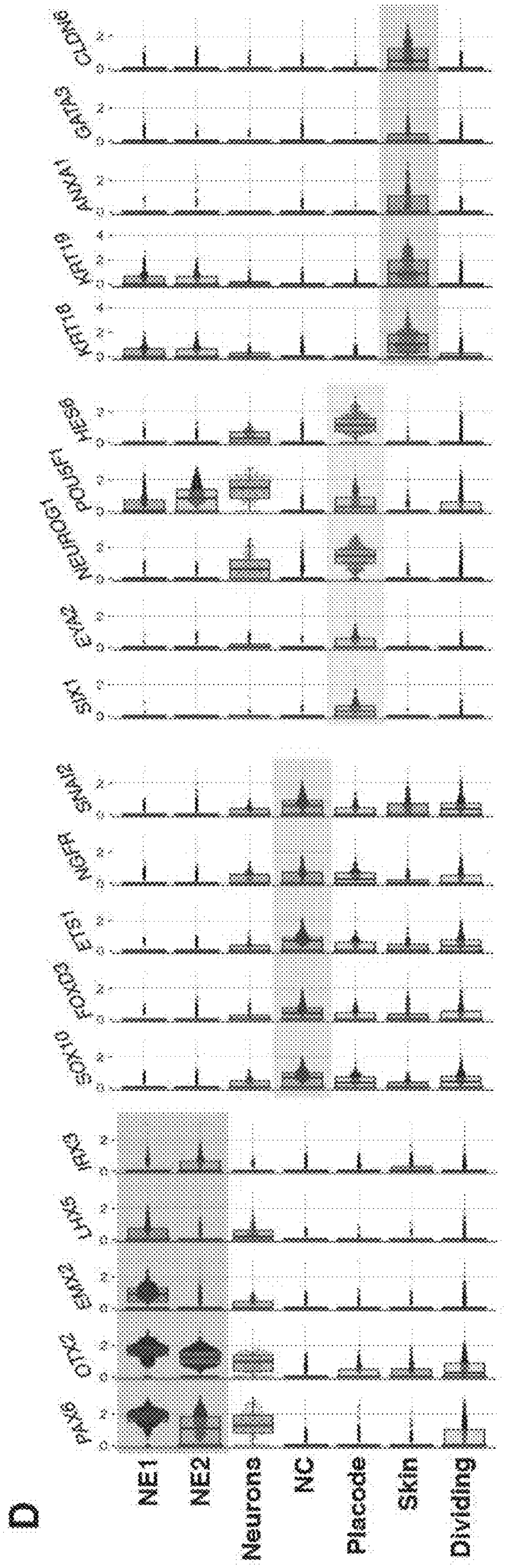
Figure 3:
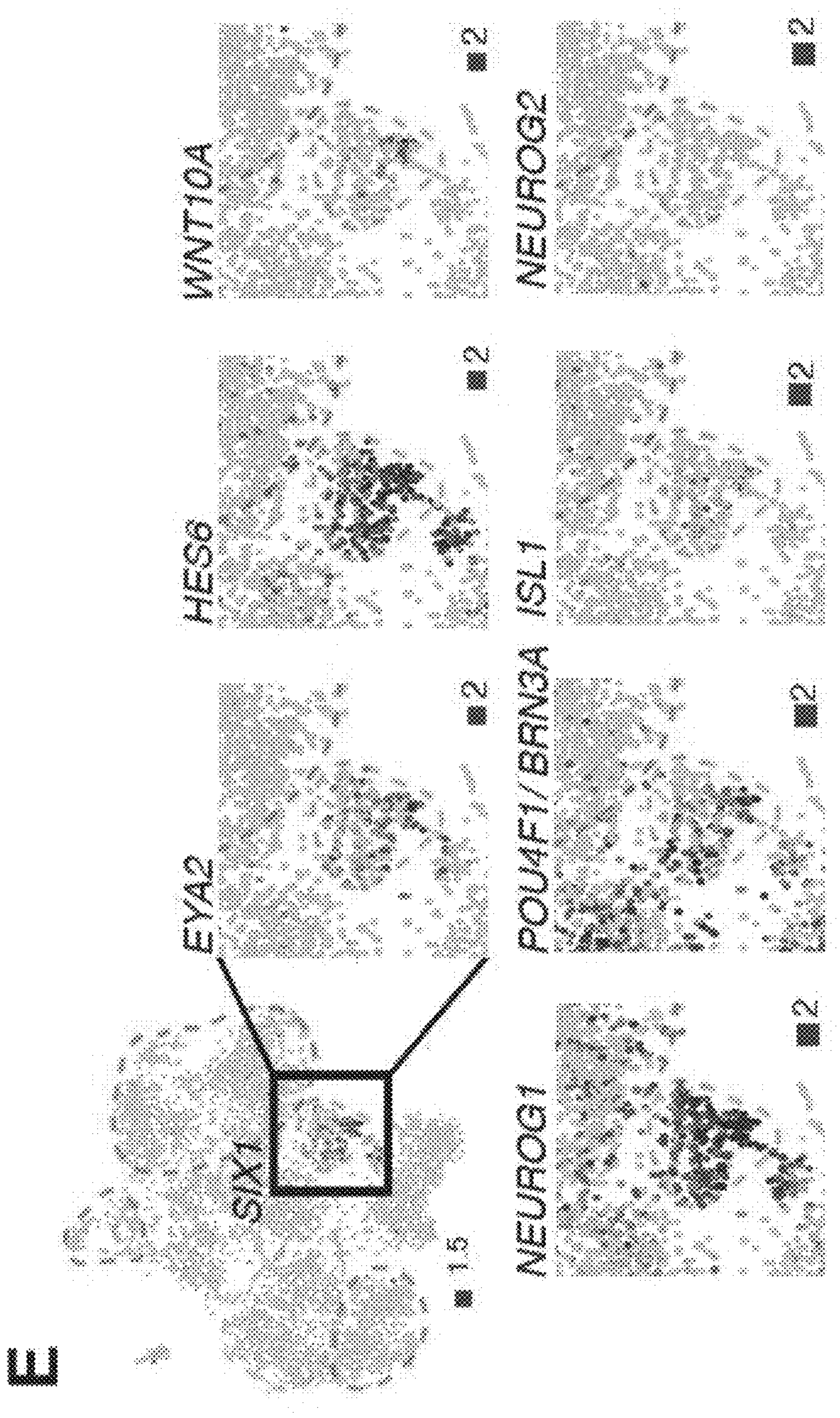
Figure 3:
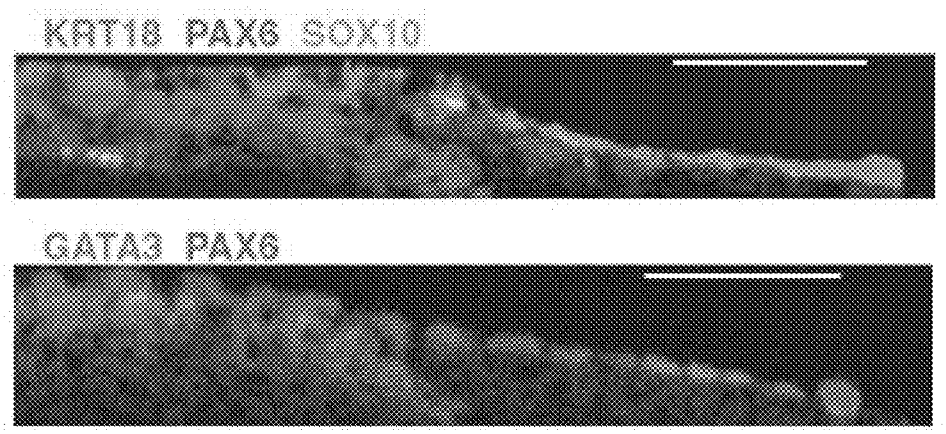
Figure 3:
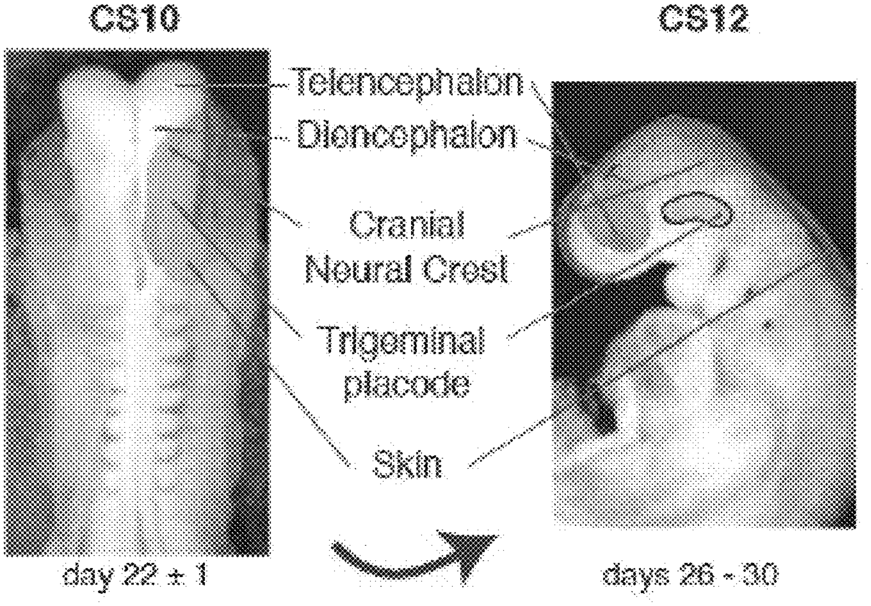
Figure 9:
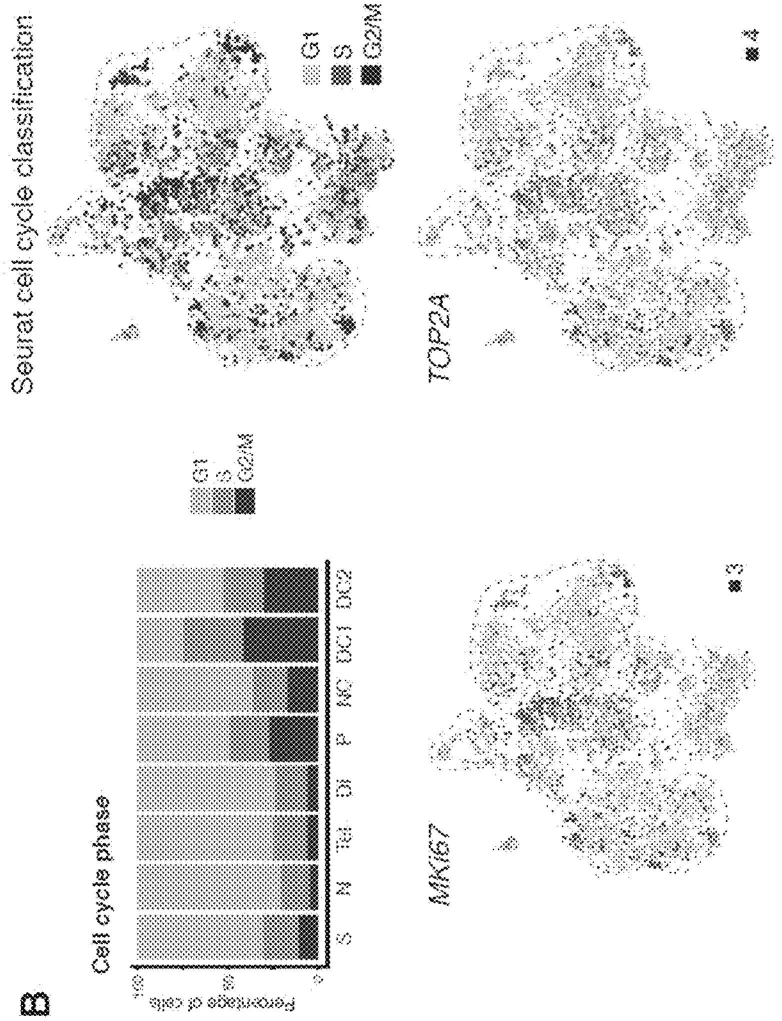
FIG. 9—related to FIG. 3. (A) Quality measures of the single-cell RNA-seq transcriptomes performed with Cell Ranger software and Seurat. Only the cells that passed QC were used in the analyses presented (see Methods). (B) The cell cycle phase was assigned to each cell using Seurat. The percentage of cells in each cell cycle phase per neuruloid population is shown as a barplot, as well as their location in the t-SNE plot. Clusters DC1 and DC2 have the highest proportion of dividing cells (>50%) and were aggregated to a single cluster of dividing cells, followed by the sensory placodes and Neural Crest clusters. Gene expression of MKi67 and TOP2A are shown as example of two genes used in the cell cycle classification. (C) t-SNE plots highlighting the different populations in the neuruloid day 7. Gene expression of PAX3 and OTX2 showing the dorsal anterior fate of the neuruloid. (D) Single-cell t-SNE graphs with a panel of marker genes arranged in a rostro-caudal progression showing expression of EMX2 and LHX5 in the telencephalic cluster NE1 and of IRX3 and EN1 in the diencephalic cluster NE2. (E) Immunofluorescence analysis of the 500 μm neuruloid (BMP4 3 ng/ml) at day 7. Sample was stained with DAP, PAX6, and LHX5. Zoomed image and side view of the PAX6+ center region is also shown highlighting PAX6−+LHX5+(telencephalon), PAX6+L-HX5− and PAX6−LHX5− (diencephalon) cells.
Figure 9:
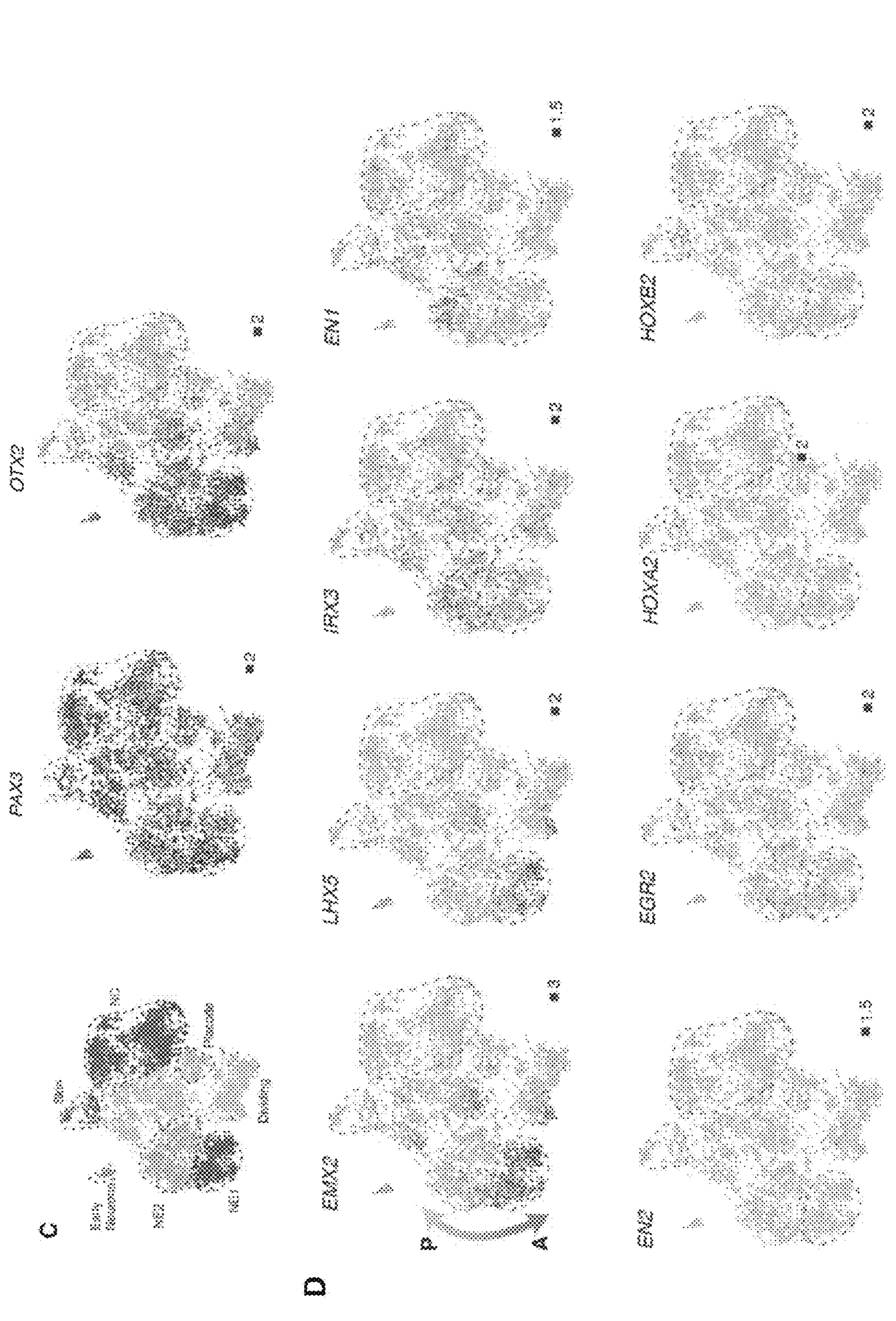
Figure 9:
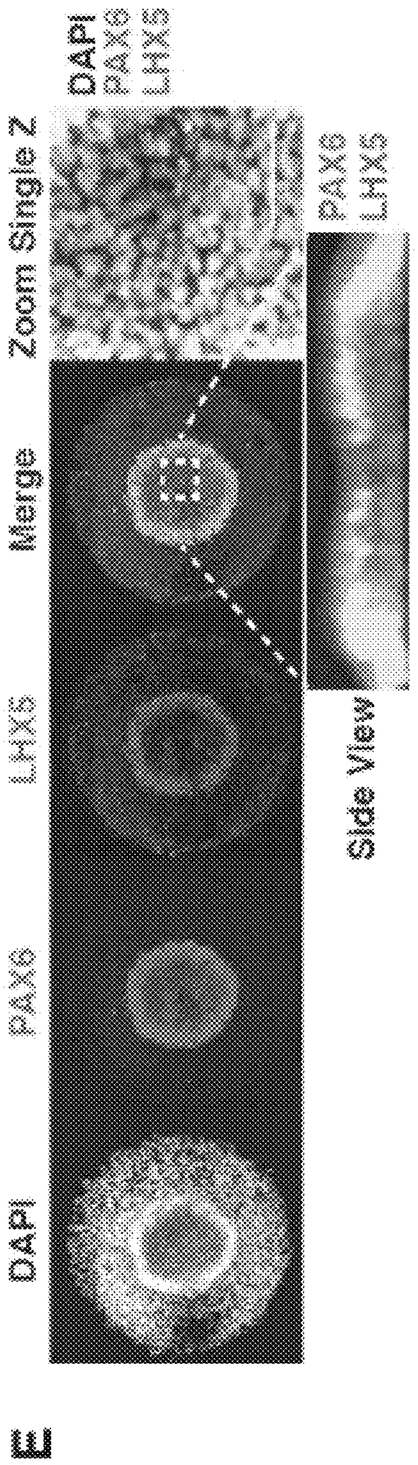

In order to precisely characterize the cell populations of the neuruloids, single-cell RNA sequencing was used, providing the first transcriptomic map of early human ectodermal development (scRNA-seq, FIG. 3A, and FIG. 9A). Low-dimensional visualization of all transcriptomes using t-SNE plots revealed a structured population of intermediate complexity characteristic of early developmental stages (FIG. 3B-C). mRNA expression of markers associated with the four ectodermal lineages are described by immunofluorescence (FIG. 313-C) was explored first. Characterization was focused on the non-proliferative population of cells (FIG. 913). Gene expression signatures of neural, neural crest (NC), sensory placodes, and epidermis was characterized (FIG. 313).

Figure 10:
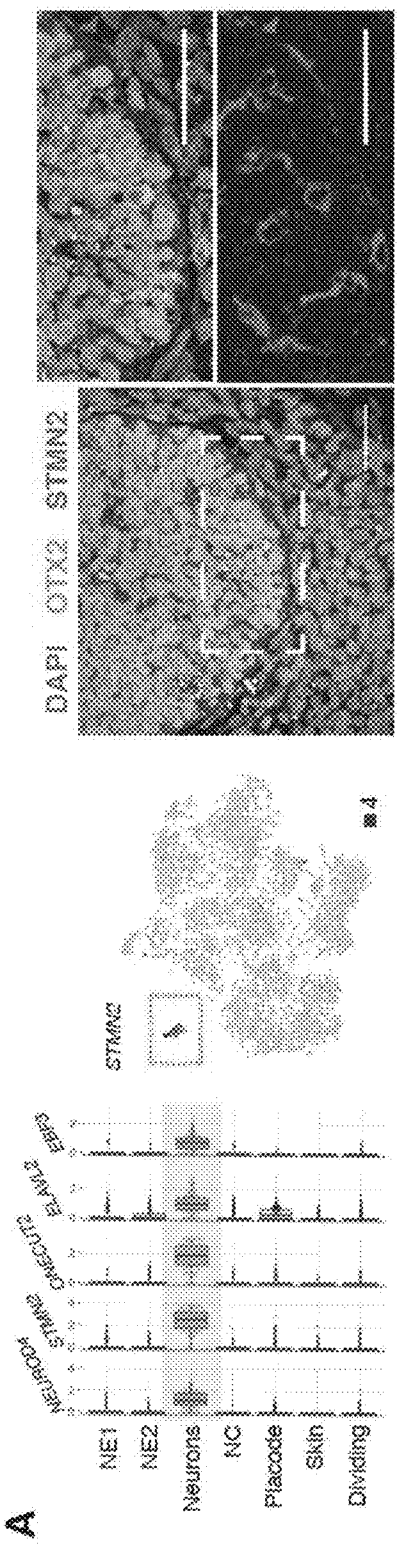
FIG. 10—related to FIG. 3. (A) Characterization of the early-born neurons in the neuruloid. Zoomed immunofluorescence image of 500 μm neuruloid (BMP4 3 ng/ml) at day 7. Sample was stained with OTX2 and STMN2, a regulator of microtubule stability characteristic of early neurons. (B) Single-cell gene expression t-SNE graphs with a battery of markers used to determine the anterior cranial nature of the neural crest population in the neuruloid. (C) Immunofluorescence analysis of the 500 μm neuruloid (BMP4 3 ng/ml) at day 7. Sample was stained with DAPI, PAX6, SOX10, and KRT18. Side view of the entire colony cross section was also shown. (D) t-SNE plots showing the specialization of WNT and BMP ligand expression in the different cell populations of the neuruloid.
Figure 10:
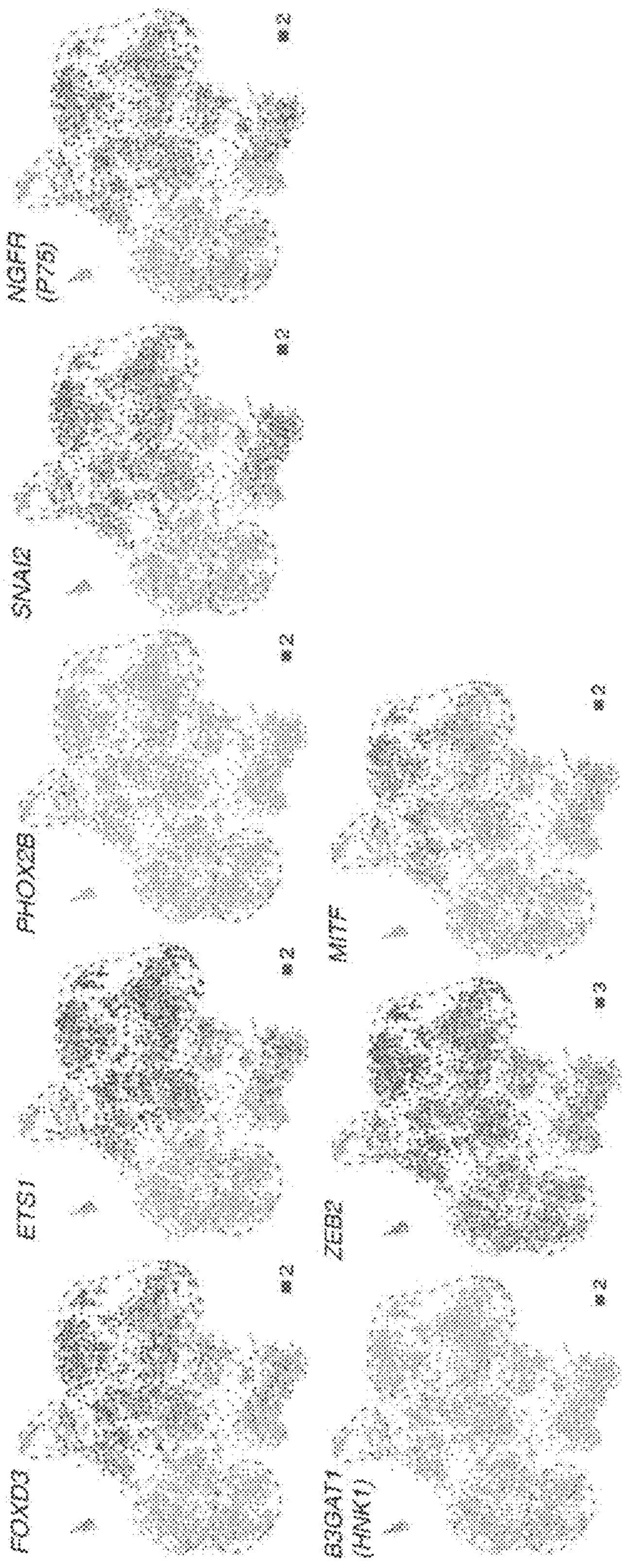
Figure 10:
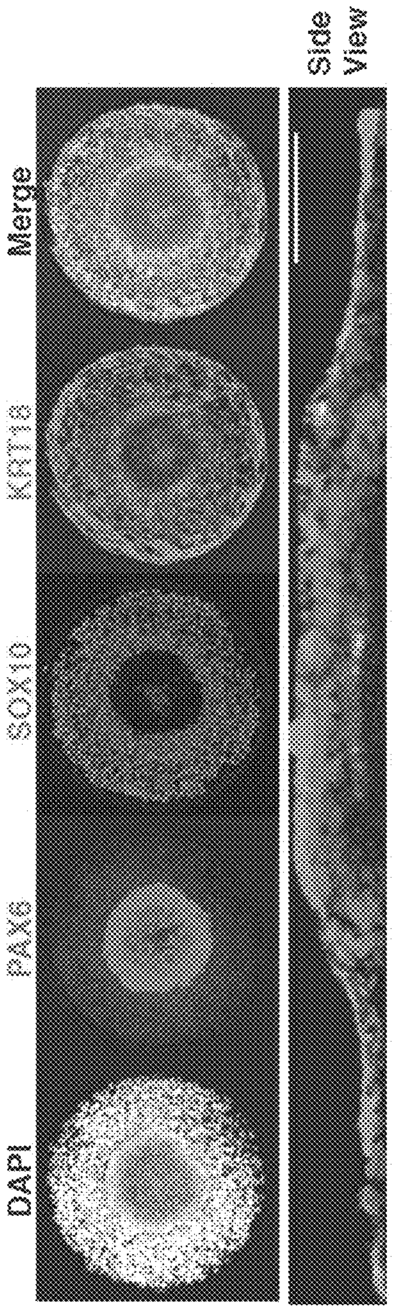
Figure 10:
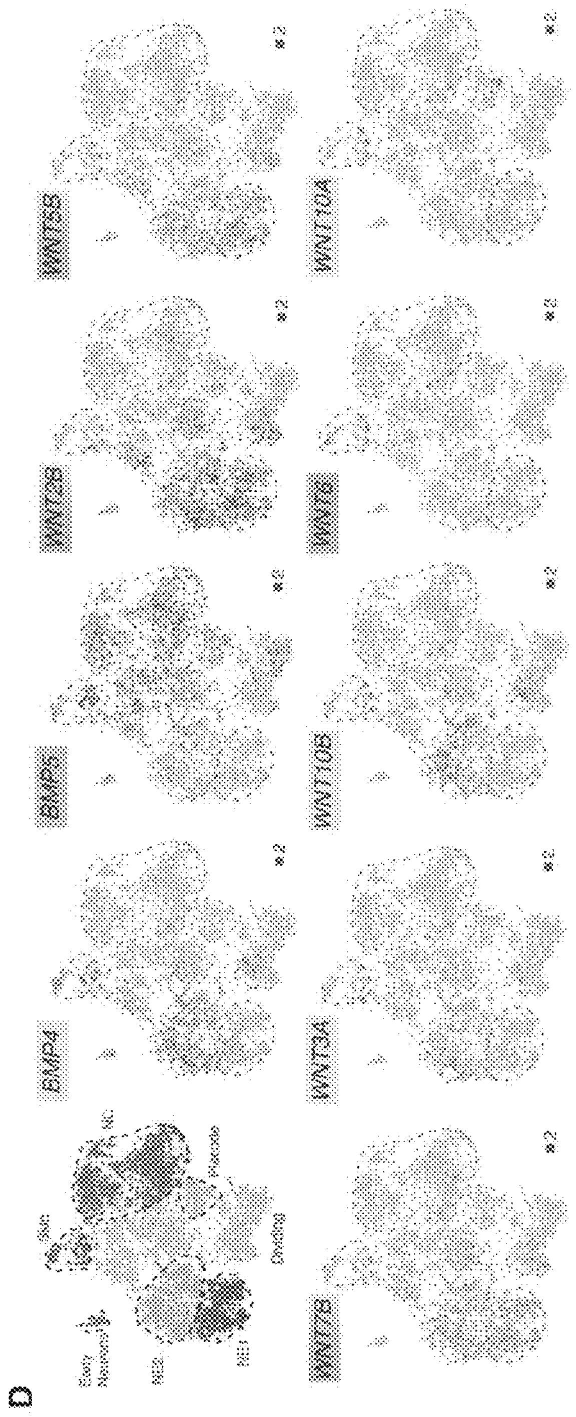

Surprisingly, unbiased clustering allowed the identification of three subpopulations within the PAX6+ cluster. Two adjacent groups were of neuro-epithelial identity (NE1 and NE2) and one displayed a signature of more mature neurons (FIG. 3C). Globally, the expression of dorsal markers such as PAX3, and lack of SHH and NKX2.1 expression strongly suggests a tissue of dorsal character in all three clusters and examination of anterior-posterior regionalization revealed that these tissues are anterior forebrain, expressing OTX2 (FIG. 9C). More specifically, NE1 expressed the telencephalon markers EMX1/2 and LHX5, but not LHX2 as seen in telencephalic rosettes (FIG. 1G and FIG. 9D-E), and NE2 expressed genes characteristic of posterior diencephalic fates such as IRX3. The presence of a PAX6-EN1+ subpopulation suggested that the posterior boundary extends to the edge of midbrain (FIG. 9D). Consistently, more posterior markers were not detected (EN2, EGR2, and HOXA2/B2). The third population harbors a signature of early-born neurons expressing NEUROD4, ELAVL2, and STMIN2 (FIG. 10A). It was found that these neurons expressed a profile typical for habenular neurons, which are derived from the diencephalic roof of prosornere 2 and express POU4F1, NHLH2, NEFM, and EBF3. Since habenular neurons have been previously implicated in neuropsychiatric disorders such as depression, schizophrenia, and drug-induced psychosis, this is a clinically relevant population of cells that is observed here for the first time in culture.

The SOX10+ cells displayed a typical NC signature including markers of epithelial-to-mesenchymal transition and migratory cells such as FOXD3, CHD6, TFAP2A, NGFR, ZEB2, and SNA12 (FIG. 3D and FIG. 10B). Consistent with the AP positional identity of the neural population, NC cells expressed the cranial specific marker ETS 1, while being negative for the trunk marker PHOX2B (FIG. 3D and FIG. 10B). Absence of HOX gene expression suggests their identity as the progeny of the first pharyngeal arch and more rostral NC populations (FIG. 10B).

The placodal population was homogeneous and demarcated by SIX1 and EYA2 (FIG. 3D-E). It lacked the expression of pituitary, lens, otic, and olfactory markers such as: GH1, CRYBB1-3, PAX2/6/8, EYA1, HES1 and DLX3-5. Expression of NEUROG1, WNT10A, and POU4F1 (BRN3A) were detected suggesting a dorsolateral placodal identity confined to the anterior part of the trigeminal placode (FIG. 3D-E). Accordingly, there was no expression of NEUROG2, required for the more posterior epibranchial placodes. The presence of cranial ganglia was also suggested by the expression of HES639.

Finally, the TFAP2A+ only population also displayed a single cluster. The transcriptional signature of this population matches the surface ectoderm progenitor population of early epidermis. It expresses several keratins: KRT8 and KRT18-19 (FIG. 3D-F and FIG. 10C), characteristic of epithelial cells, as well as ANXA1, CLDN6, GATA3, MSX1/2, and WNT6 (FIG. 3D and FIG. 10D).

The next question was to determine the developmental timing associated with the neuruloids compared to in vivo human development. The fact that all four ectodermal markers are present suggests at least neural plate stage as a lower bound. As an upper bound, epithalamic neurons first appear at neural tube closing stages (Carnegie stage 9-11), while in mouse they appear prior to E11.5 (Allen Brain Atlas). FOXG1, which is not detected here, has an expression onset starting at day 25 in a domain that expands to the entire telencephalon by week 7. Additionally, the expression of HES6, which marks placodes in the neuruloids, begins at E9.5 in mice, a period which corresponds to Carnegie stage 10 of human gestation (22-23 days post-fertilization). Altogether, this places the neuruloid at neural tube closure stages, from day 21 to 25, providing a window to the earliest stages of human development (FIG. 30).

A pulse of pSMAD1 at the edge signaling creates juxtaposition of neural and non-neural ectoderm.

Figure 4:
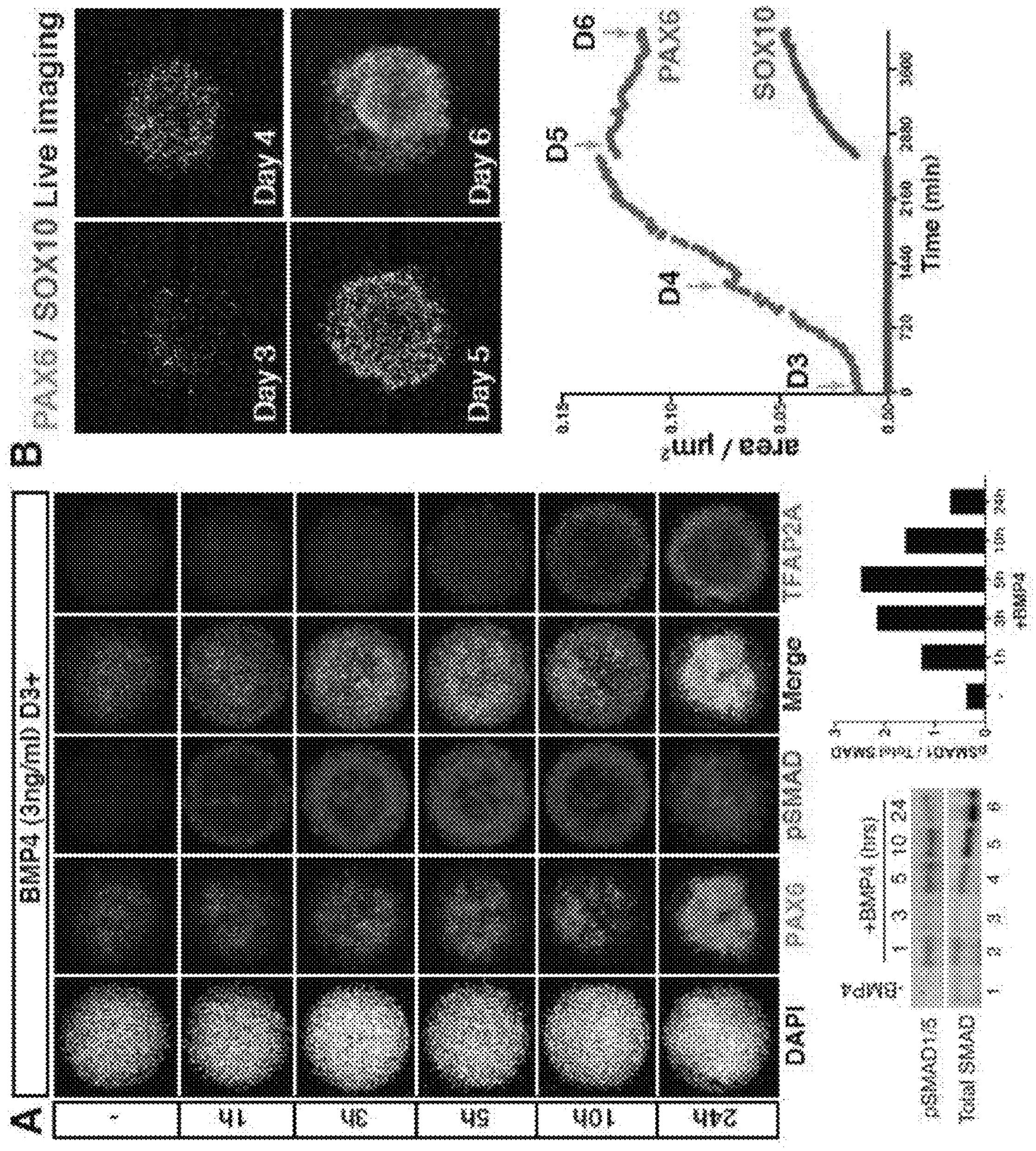
FIG. 4 depicts coupling of cell fate specification with a two-step morphogenesis mechanism during neuruloid formation. (A) (Top) time course immunofluorescence analysis of the neuruloid from day 3 to 4. Day 3 micropattern colonies were treated with BMP4 (3 ng/ml) for 1, 3, 5, 10, and 24 hours then stained with PAX6, pSMAD1, and TFAP2A. (Bottom Left) Western blot analysis of the micropattern colonies treated with BMP as above. Sample were stained with anti-pSMAD1/5 antibody. Anti-total SMAD antibody was used as a control. (Bottom Right) Quantification of the western blot analysis. (B) Time-lapse video microscopy imaging of neuruloid formation from day 3 to 6 using the live reporter line (PAX6::H2B-Citrin and SOX10::H2B-tdTomato). Images were recorded every 30 min from day 3 to the end of day 5 (66 hours total). Representative images are shown (a; first image of day 3, b; first image of day 4, c; first image of day 5, d; last image of day 5). Graph depicts PAX6+ and SOX10+ area dynamics. Arrows indicate the time points of each corresponding image. (C) Immunofluorescence imaging of 500 μm micropatterned colonies with PAX6 (green) and SOX10 (red) at day 4, 5, 6, and 7. (Left) Top view. (Right) side view from center to edge (left to right). (D) Immunofluorescence analysis of day 7 neuruloid treated with FGF (6 ng/ml), SU5402 (5 μM), CHIR (3 μM), IWP2 (2.5 μM) from day 3 to 7 concomitants with BMP4 (3 ng/ml). (E) Associated quantification of PAX6, SIX1, and SOX10 area of the neuruloid treated with indicated drugs. Data are mean±standard deviation. All experiments were performed with 500 μm micropatterned colonies.
Figure 4:
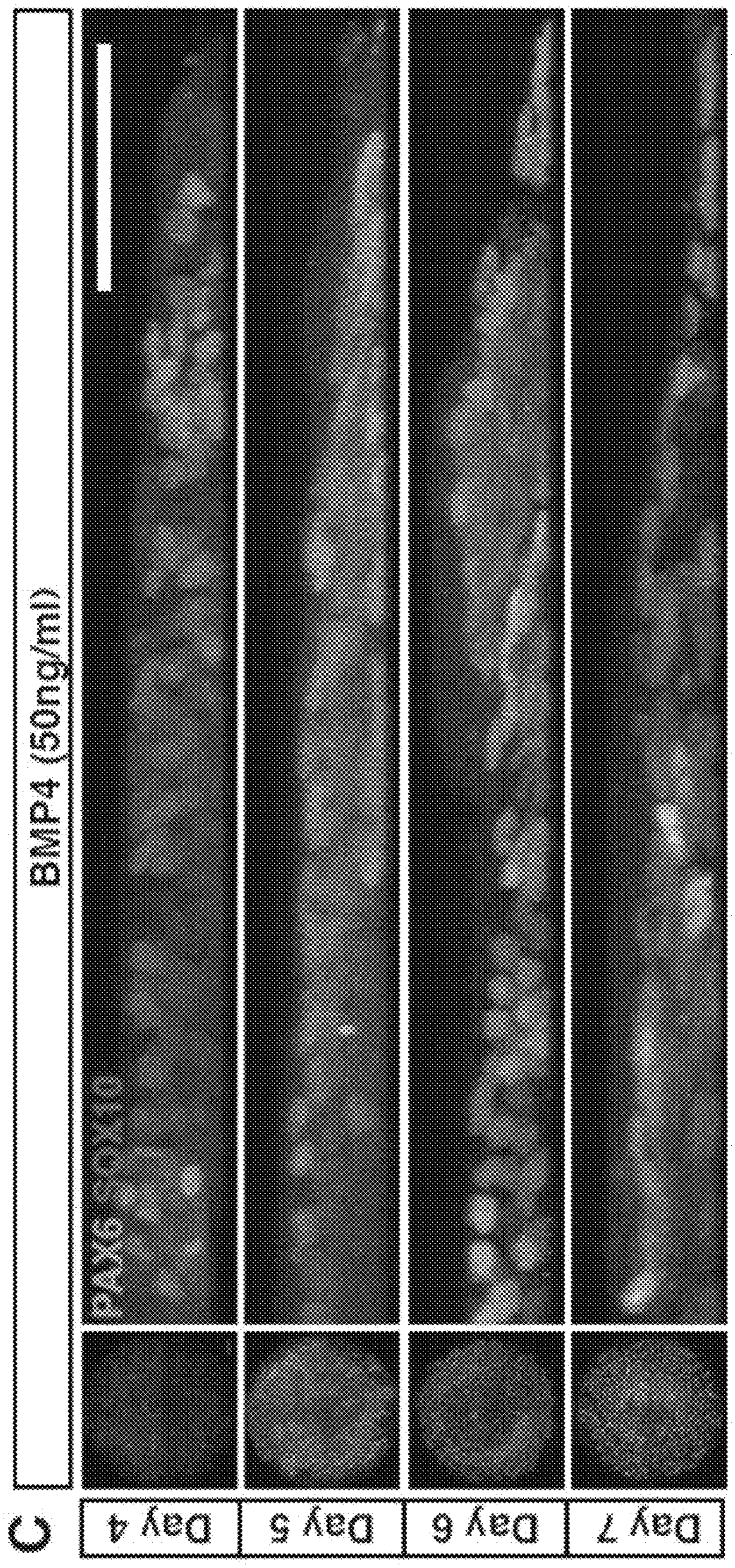
Figure 4:
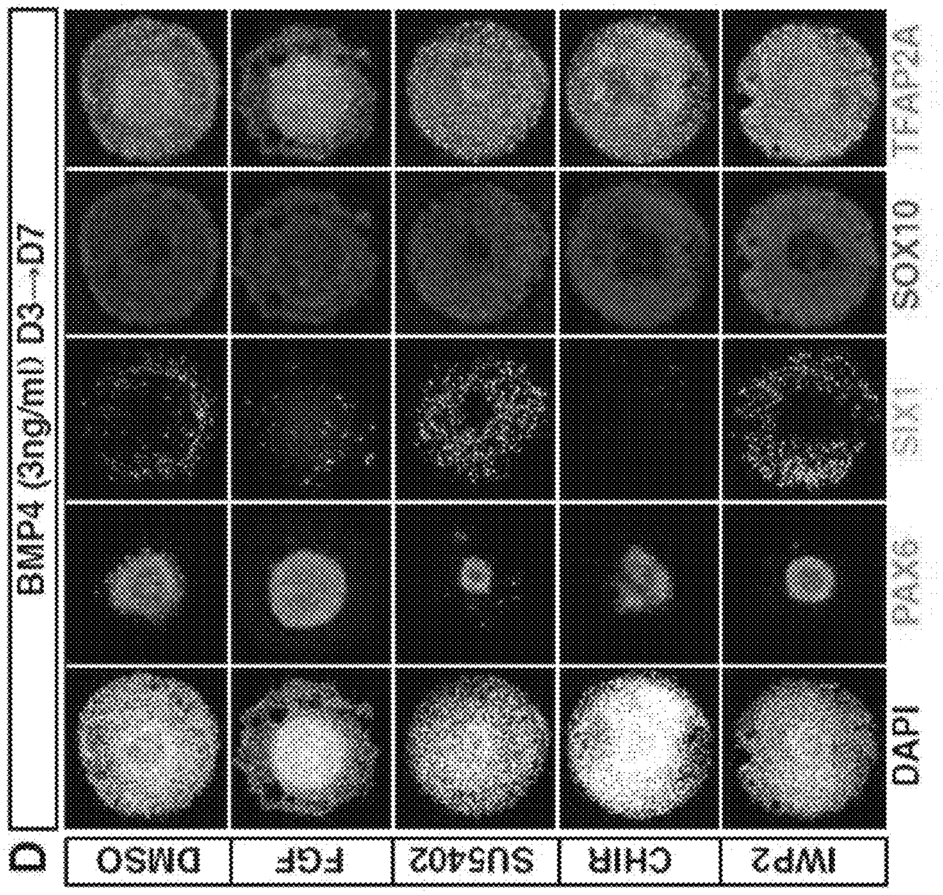
Figure 4:
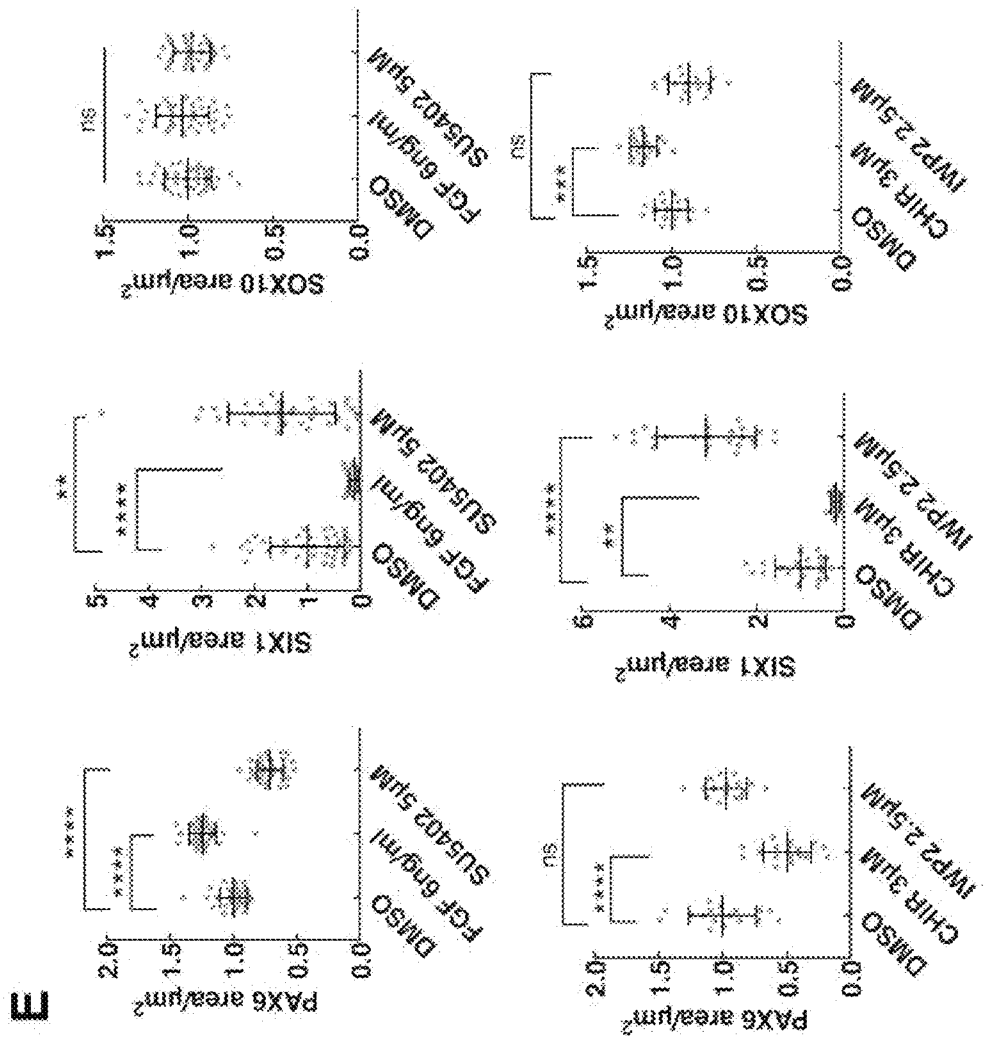

To uncover the molecular mechanisms of neuruloid self-organization, the signaling dynamics over a time-course after BMP4 presentation was followed. A pulse of pSMAD1 restricted to the colony edge was detected (FIG. 4A). This led, 24 hours later, to the induction of TFAP2A+ in the same domain suggesting specification of non-neural ectoderm. Juxtaposition of neural and non-neural fate has been shown to induce the formation of neural crest and sensory placodes at the edge of the neural plate in model systems (Selleck. MA. & Bronner-Fraser M (1995) Development 121, 525-538). To test if this induction scheme occurs in the neuruloids described herein, the dynamic of fate acquisition through the use of a double live reporter of PAX6 and SOX10 was followed using CRISPR-CAS9 mediated incorporation of fluorescent tags. Time-lapse confocal microscopy was used to image the fate reporter in consecutive 24 hours time windows through the process of neuruloid formation after BMP4 presentation (FIG. 4B). Analysis of the temporal evolution of the area occupied by the PAX6+ cells revealed an initial phase of specification with linear growth of the PAX6+ domain from days 3 to 5, followed by domain shrinkage and condensing into the central neural structure (FIG. 413). Only a few SOX10+ cells were detected during this initial phase, but a large expansion occurred in the SOX10 area concomitant with the PAX6 domain condensation starting at day 5. This was confirmed at higher spatial resolution by immunofluorescence (FIG. 4C). Therefore the specification of neural crest occurs downstream of non-neural ectoderm specification and its juxtaposition to the neural population in a mechanism that is evolutionary conserved.

Signaling Crosstalk in the Neuruloid

In order to evaluate the contributions of WNT and FGF pathways these pathways were inhibited or enhanced in the neuruloid using small molecules or ligand presentation (FIG. 4D). Interestingly, the PAX6 domain was sensitive to both FGF and WNT signaling activation, which suggest that these two molecules can alter the neural specification process and might confer regional identity to the neural population (FIG. 4D-F). The SOX10 population however was completely insensitive to FGF signaling, but increased with WNT activation. This is consistent with a strong requirement for WNT signaling in protocols aiming at inducing neural crest populations. Finally, the placodal population was extremely sensitive to both WNT and FGF signaling. Activation of both WNT and FGF led to a complete removal of the placode. Conversely, WNT inhibition increased their proportion (FIG. 4D-F). This demonstrates that the signaling pathway upstream of fate acquisition is also evolutionary conserved from amphibians to human.

Modeling Huntington's Disease in Human Neuruloids

The ability to generate a large number of homogenous self-organizing neuruloids disclosed herein prompted us to use the neuruloids to model Huntington's disease (HD). We and others have previously shown or predicted a strong phenotype of HD during human neurogenesis (46-48). HD is a dominant autosomal disease caused by an expansion of CAG repeats leading to an increase of polyQ expansion, which correlates with HD onset, at the N-terminus of the Huntingtin (ITT) protein. As neuruloids represent the earliest step of neural development, a HD developmental signature occurring earlier during neuronal development was hypothesized. Five HD isogenic series of hESCs including different CAG expansions: 56 and 72, as well as an homozygote null HTT−/− mutant along with a WT parental line and a 20 CAG control were used (48).

Figure 5:
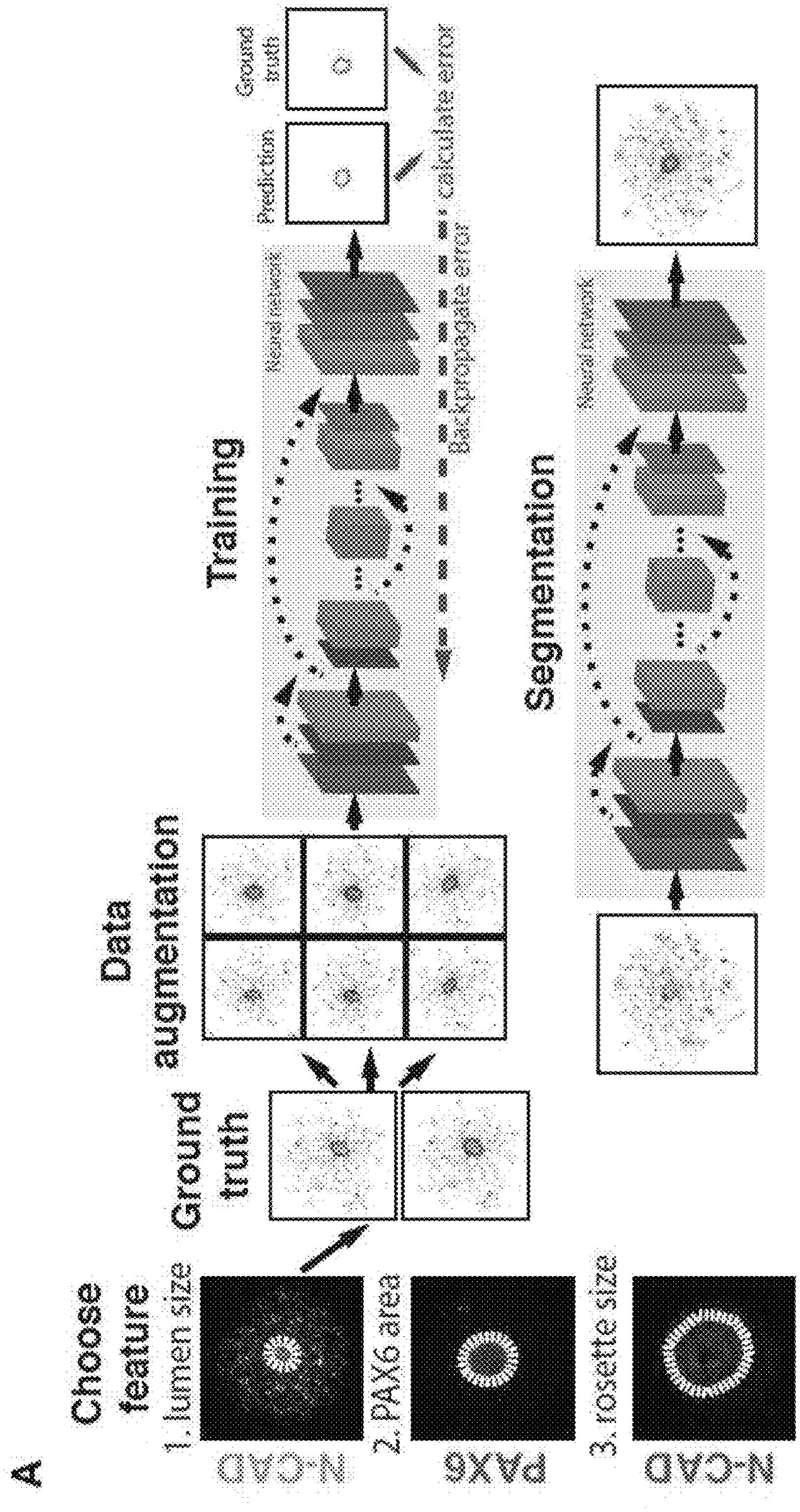
FIG. 5 depicts phenotypic signatures associated with Huntington disease using deep neural networks. (A) Quantification using deep neural networks. Three features of interest are segmented and quantified: lumen size, PAX6 area, and overall rosette size. Only quantification of the lumen size is exemplified here: 100 colonies are manually segmented for creating a pool of training images associated with a ground truth. After data augmentation, a neural network is trained and used to segment lumen areas in remaining colonies. (B) Representative images of lumen sizes for different HD isogenic lines in the rosette formation assay. (Left) N-CAD staining allows imaging lumens for wild-type hESC lines (RUES2), control 20 CAG line (20 CAG), expanded polyQ lines (56 and 72 CAG) and HTT−/− hESC lines. (Right) Associated quantification of lumen sizes normalized by the colony area using the pipeline presented in panel A. (C) Representative immunofluorescence imaging of day 7 neuruloid (BMP4 50 ng/ml) of wild-type hESC lines and HD cell lines. Samples were stained with PAX6 (green), SOX10 (red), and N-CAD (orange). (Right) Associated quantification of PAX6 area normalized by the colony area using the pipeline presented in panel A. (C) Representative immunofluorescence imaging of day 7 neuruloid (BMP4 3 ng/ml) of wild-type hESC lines and HD cell lines. Samples were stained by N-CAD (red), and COL4 (green). (Right) Associated quantification of COL4 intensity along the N-CAD+ periphery using the pipeline presented in panel A normalized by the periphery length.
Figure 5:
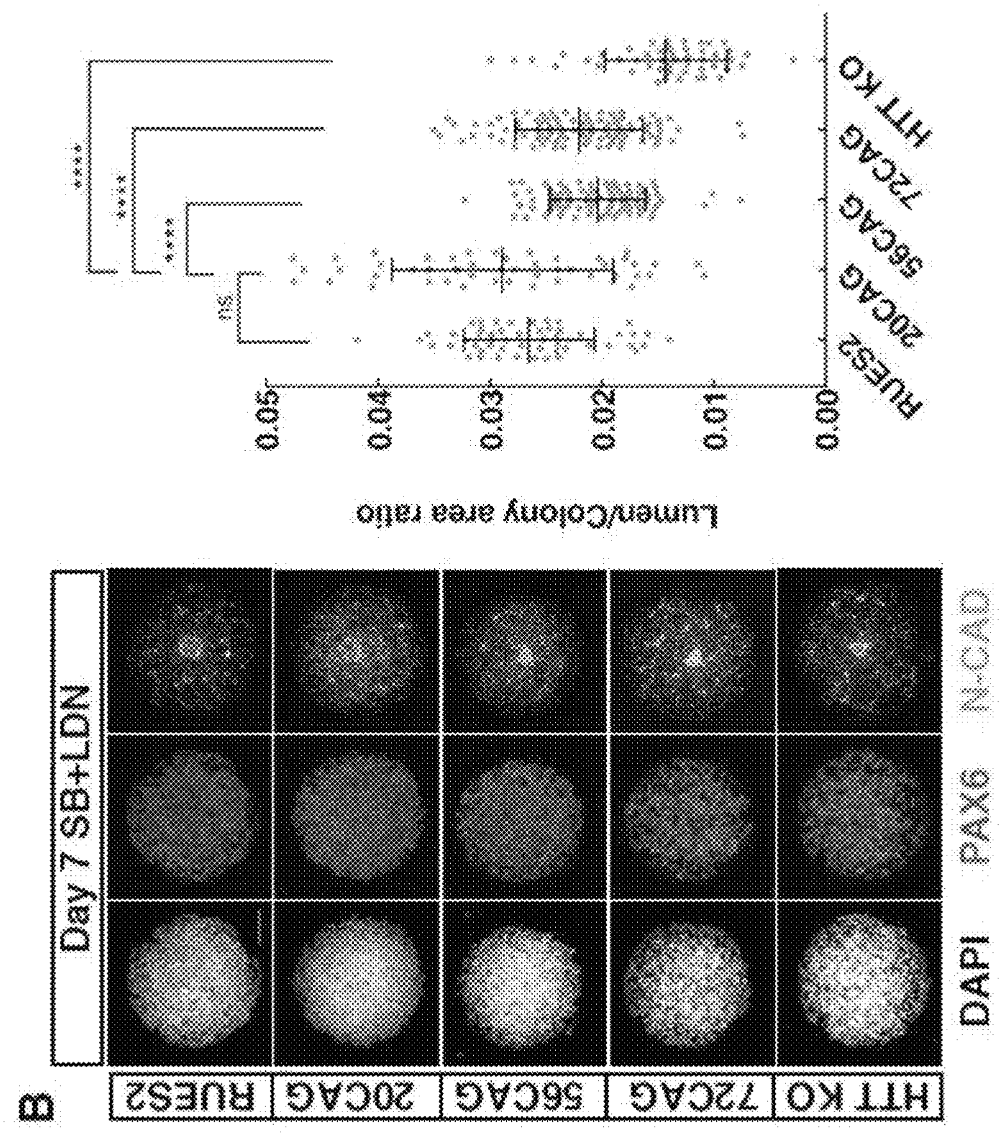
Figure 5:
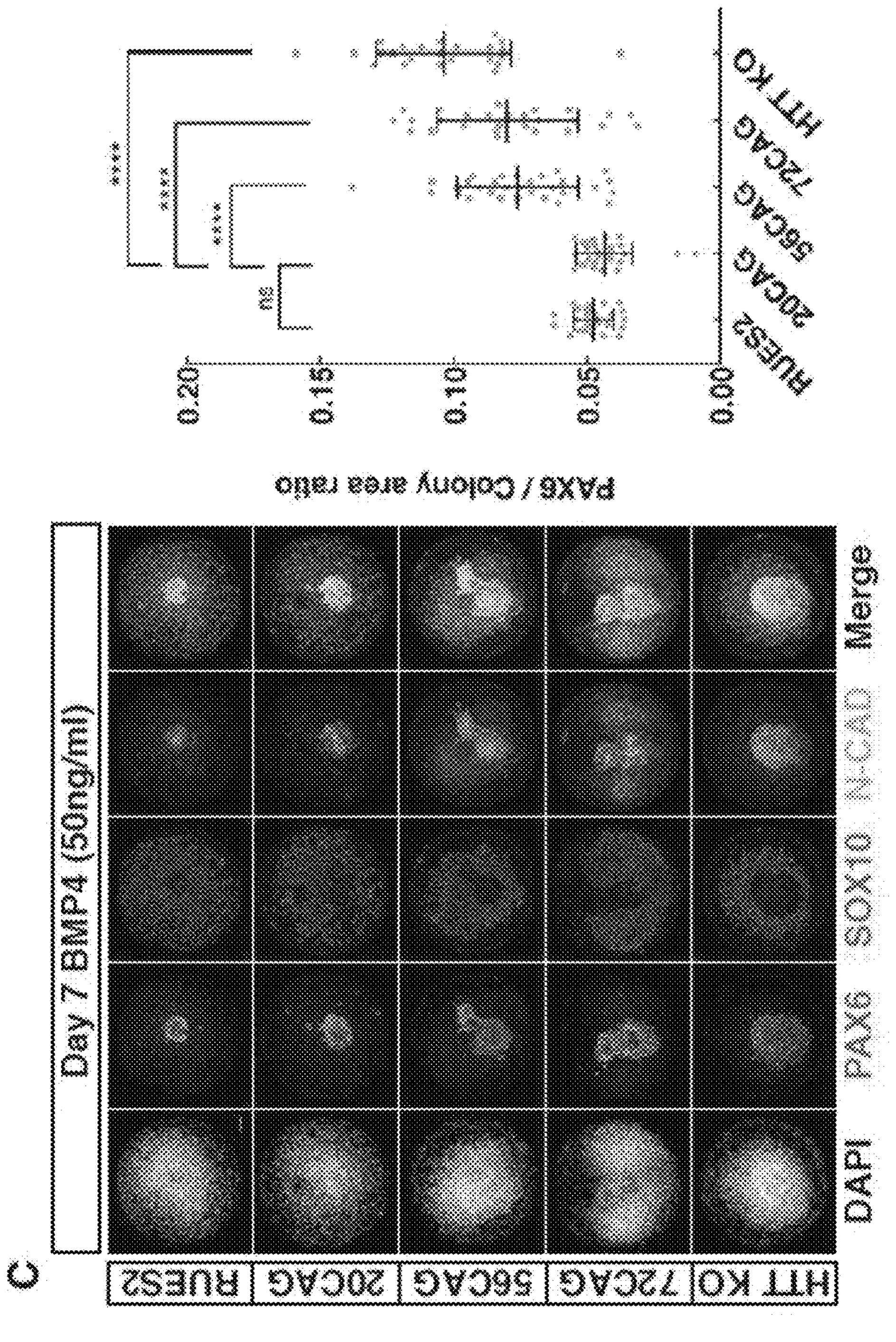
Figure 5:
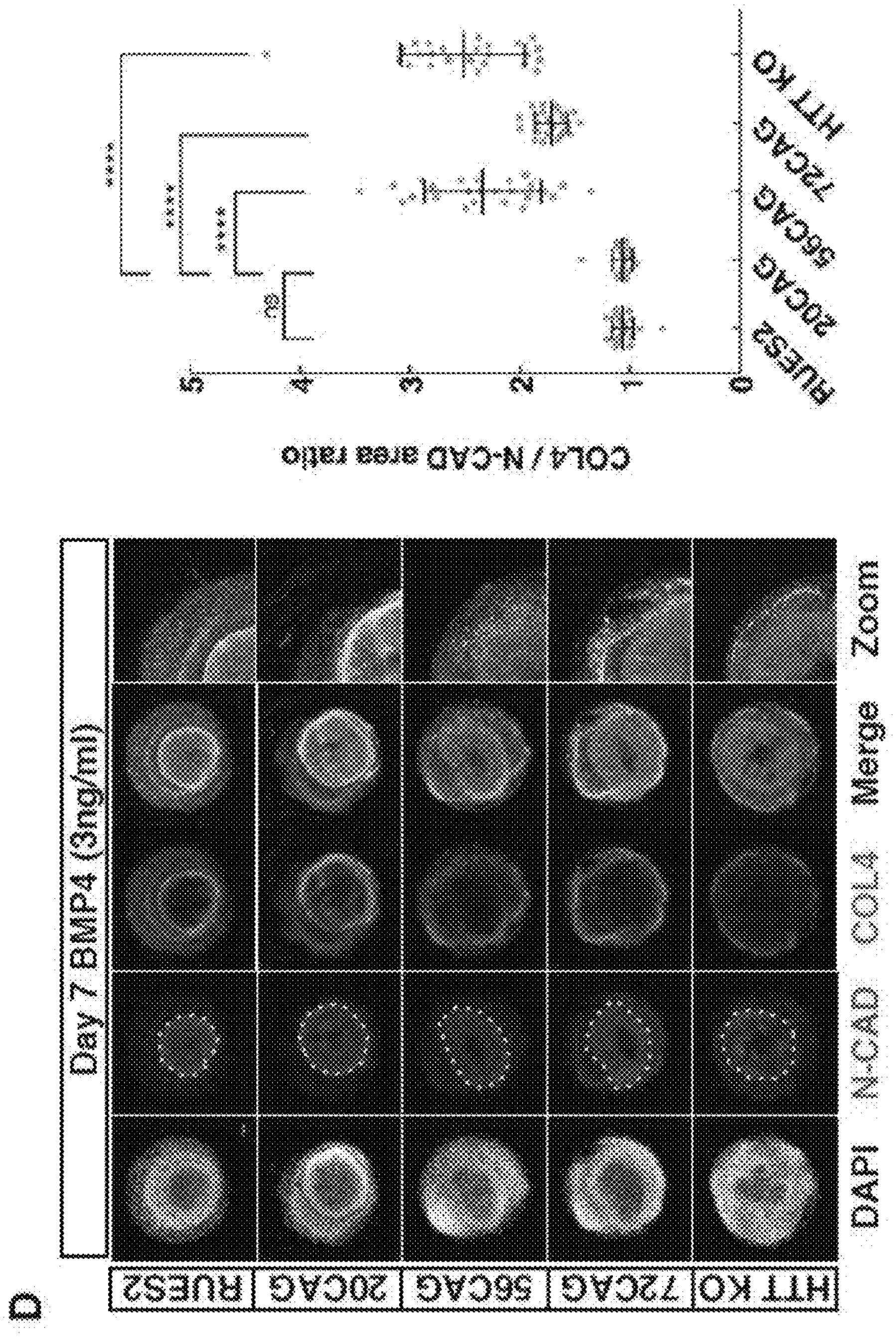
Figure 11:
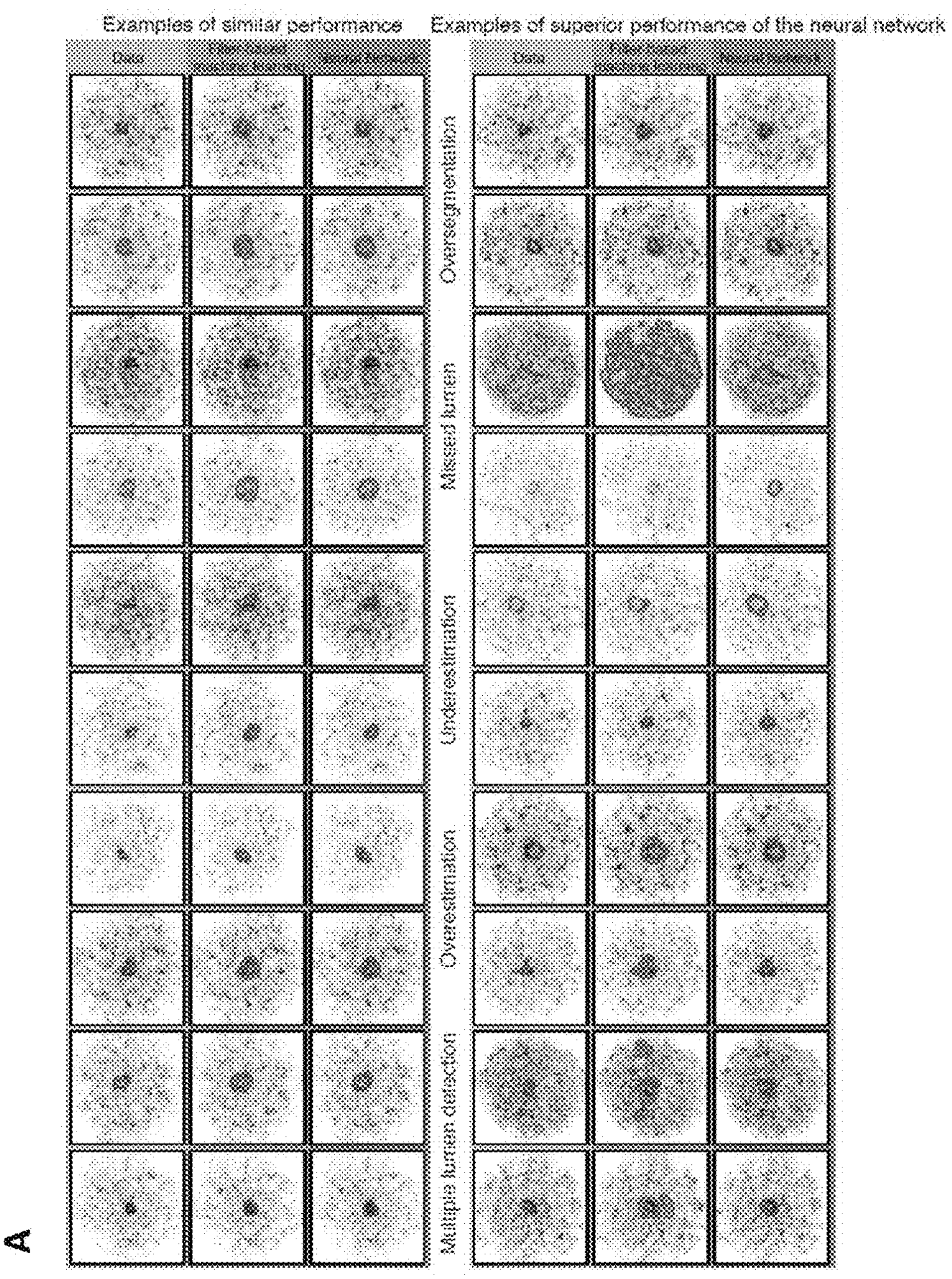
FIG. 11—related to FIG. 4-5. (A) Comparison of lumen segmentation by the filter-based machine-learning framework Ilastik and a deep neural network trained on the same images and applied to previously unseen data. (Left) Examples in which the two approaches have similar performance, (Right) examples where the neural network performs significantly better. The neural network almost perfectly segments the lumen in a wide range of conditions, even when the filter-based classifier fails due to the reasons indicated on the side of the right column. (B) Immunofluorescence analysis of 500 μm micropatterned colonies of RUES2, 20 CAG, and 56 CAG by PAX6, SOX10 at day 7 of SB+BMP4 (3 ng/ml) protocol. (Right) Quantification of PAX6+ area.
Figure 11:
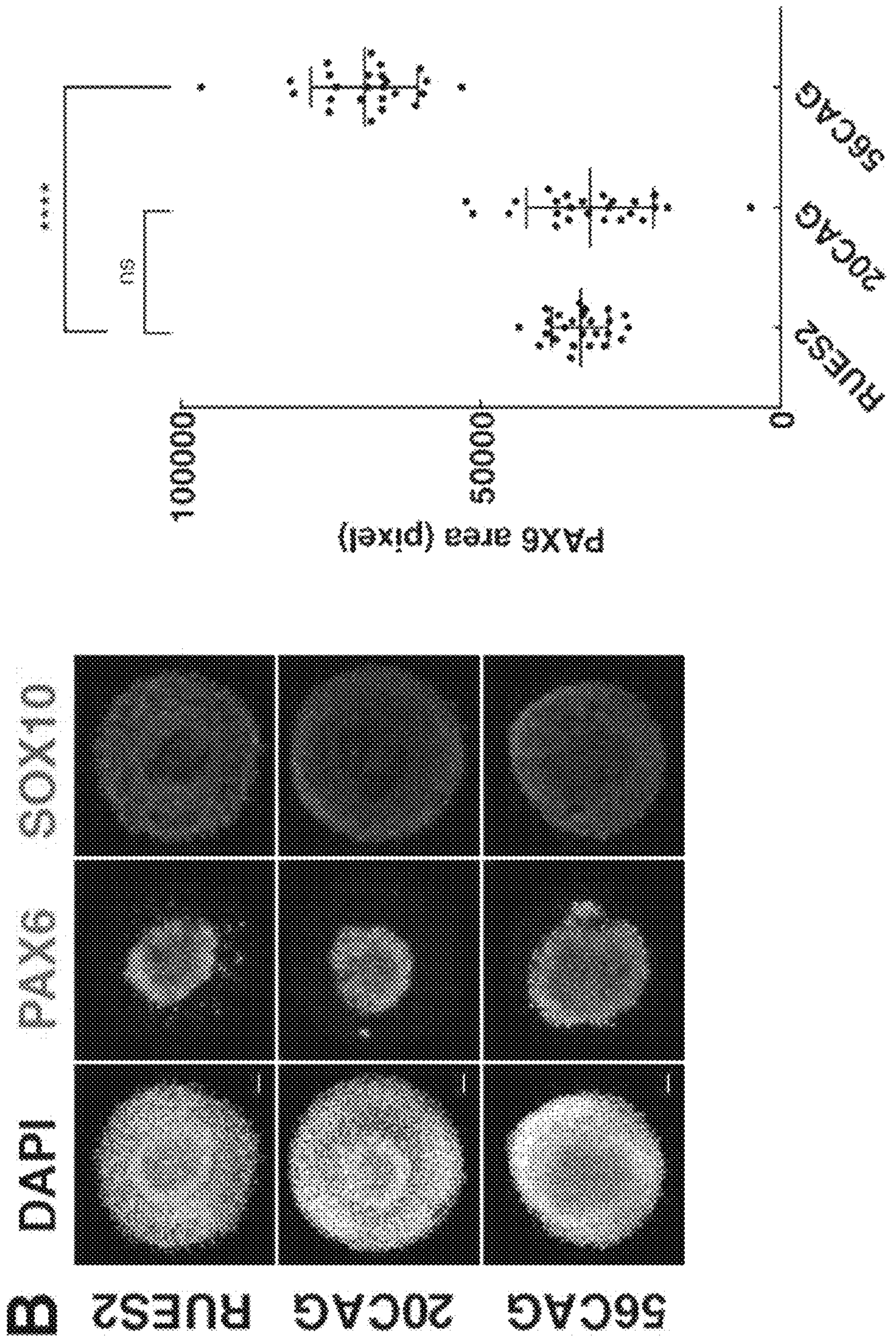

It was hypothesized that it could be possible to observe disease phenotypes using three main morphological features of rosette or neuruloid organization: lumen size in the rosette formation assay, PAX6 area/rosette extension and amount of collagen IV around the PAX6 center in the neuruloid assay. In order to provide fast, robust, and highly quantitative measurement over thousands of neuruloids simultaneously in different genetic backgrounds, deep convolutional neural networks were used. To overcome the need for large training data sets, a data augmentation scheme was designed to artificially increase the training pool of images (FIG. 5A). This approach outperforms traditional, filter-based, machine learning strategy, as highlighted by an independent analysis of the same data set, lumen formation in control non-HD cells (FIG. 11A).

This unique tool led to the discovery of three novel early, developmental phenotypes for HD. First, in the rosette formation assay, a gradual reduction in lumen size that was correlated with the number of CAG repeats was observed (FIG. 5B). Second, in the neuruloid formation assay, CAG expanded lines showed an increase in the central PAX6 domain and a gradual loss of radial symmetry (FIG. 5C). This observation was independent of the BMP4 concentration used (FIG. 11B). Finally, all HD lines showed significantly lower or a complete loss of collagen layer at the basal side of the central neural rosette (FIG. 5D). In all three cases, the Htt−/− phenocopied the most extreme CAG expanded phenotypes. This is in agreement with previous observations, suggesting that CAG expansion of HTT protein, in a developmental context, represents a loss of function, and not a gain of toxic function as it is often hypothesized.

HD Mutation Affects Neuruloid Morphogenesis

Figure 6:
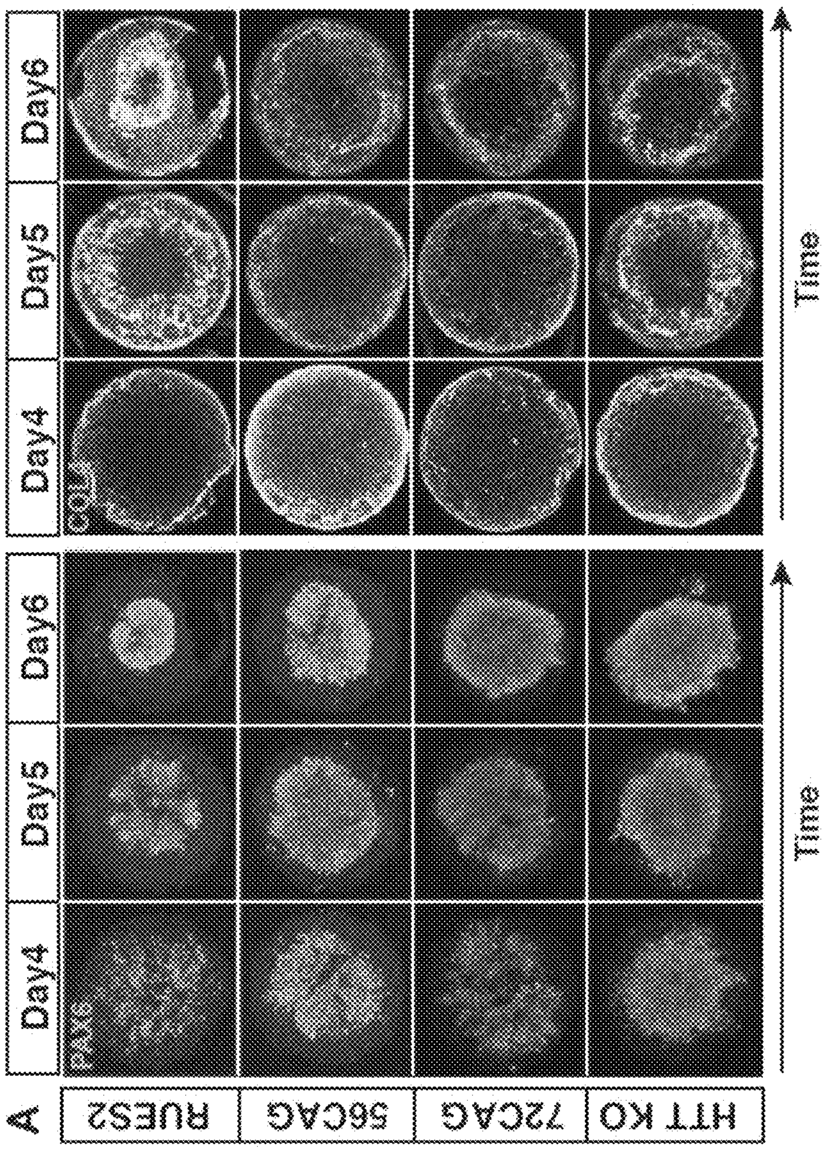
FIG. 6 depicts misregulation of cytoskeleton organization genes implicated in impairment HD neuruloid morphogenesis. (A) Time course immunofluorescence analysis of wild-type (RUES2) and HD mutant lines (56 CAG, 72 CAG and HTT−/−) of neuruloid from day 4 to 6. Samples were stained with PAX6 (green) and COL4 (orange). (B) (Top) Side view of re-sliced z-stack around N-CAD+ center region of RUES2, 56 CAG, and Htt Samples were stained with N-CAD (red), PAX6 (green), and COL4 (orange). (Bottom) Blow-up of the highlighted area. Note that the central lumen is closed in RUES2, but not in 56 CAG nor HTT KO. (C) Quantification of the PAX6 area for (A) showing a sharp area compaction in WT RUES2 between days 5 and 6 which is progressively absent with increasing CAG length and HTT−/−. Data are mean e standard deviation. (D) RUES2 and 56 CAG background distribution within the NE and NC populations of the neuruloid. (E) Shows 1,471 differentially expressed genes (DEG) between wild-type (RUES2) and 56 CAG isogenic line in the neuruloid day 7. 499 DEG were specific to Neural Epithelium (NE) and 663 specific to neural crest (NC). DEG were called by Seurat and filtered by adjusted p-value ≤0.05 and a minimum percentage difference of cells expressing the gene ≥10%. Additionally, it is shown the overlap with a list of DEG in post-mortem prefrontal cortex (BA9) samples between HD patients and control as reported by Labadorf et al. (2015). (F) Several genes of WNT/PCP pathway are down-regulated in the 56 CAG background in both NE and NC. (G) Several genes related to cytoskeletal organization are down-regulated in the 56 CAG background in both NE and NC.
Figure 6:
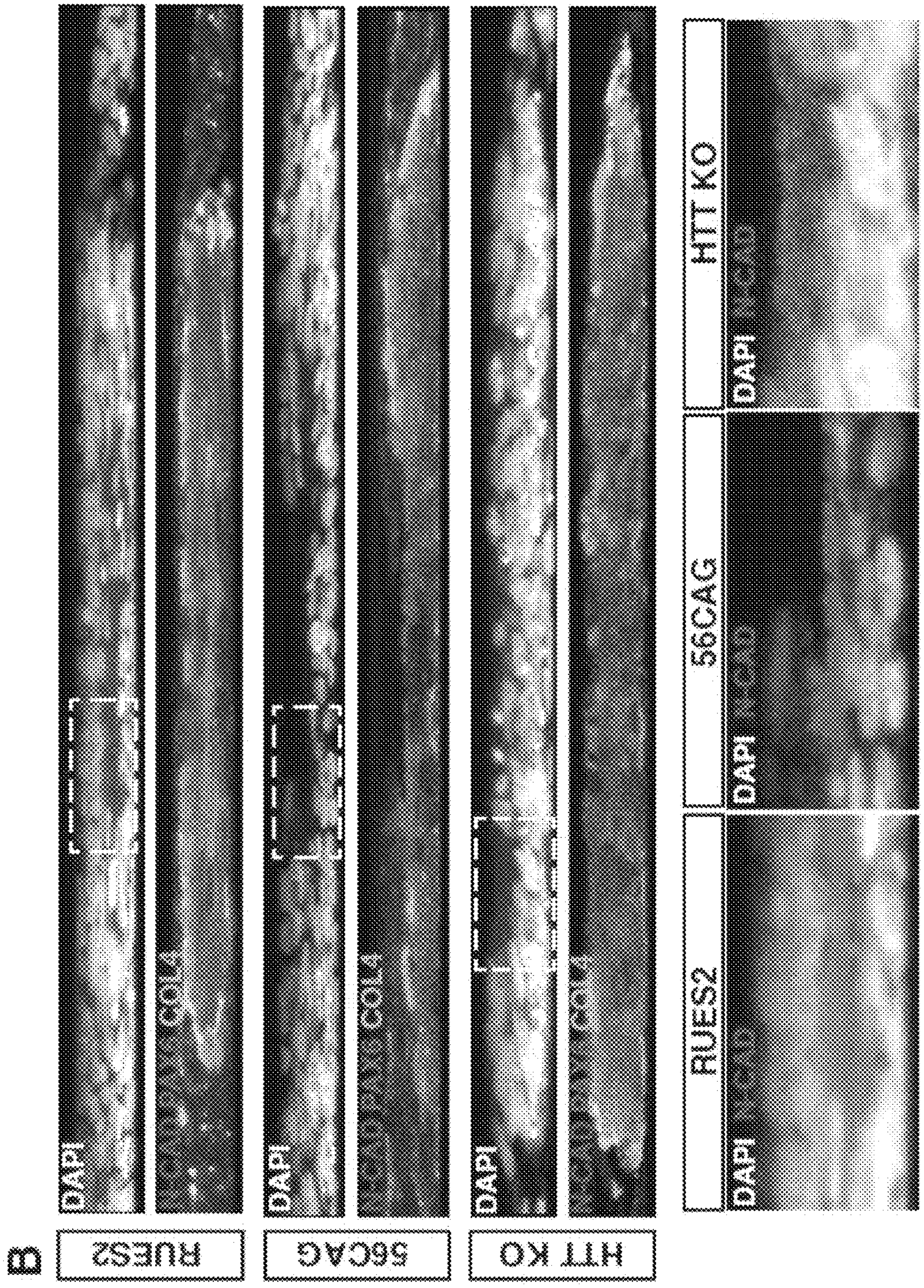
Figure 6:
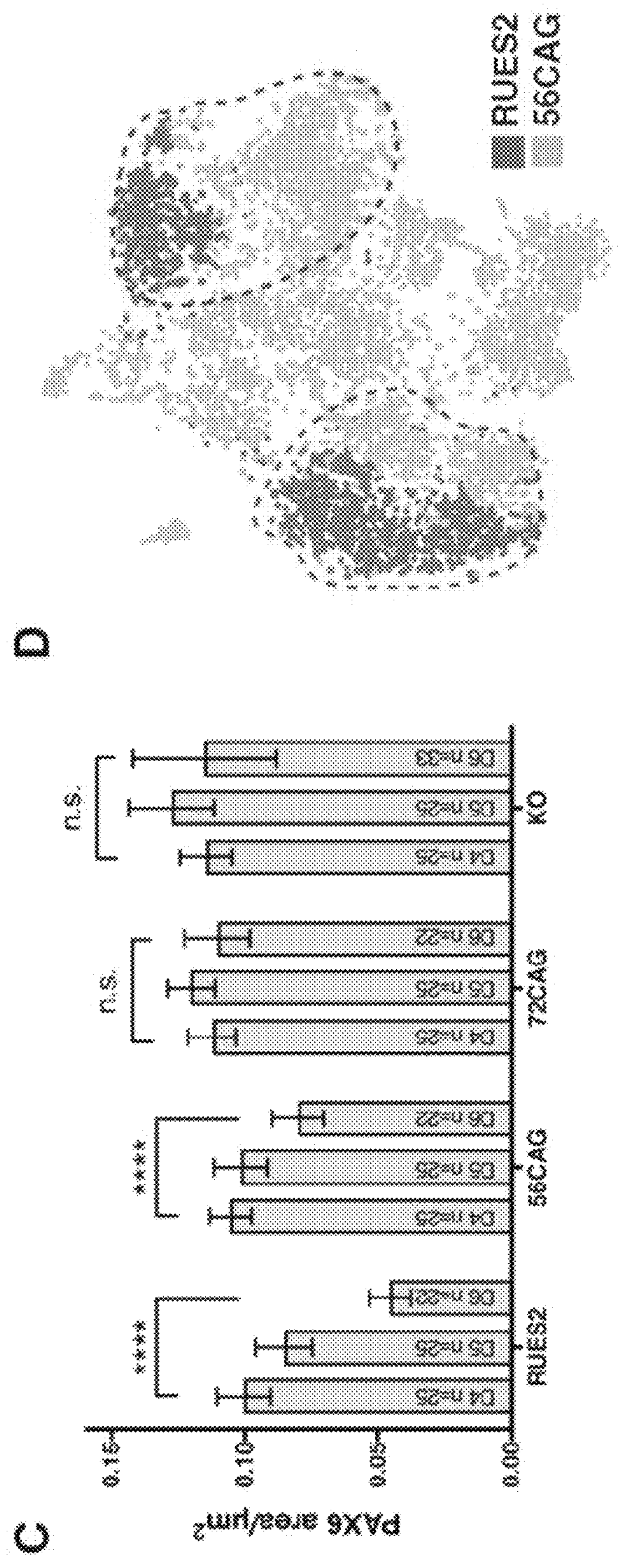
Figure 6:
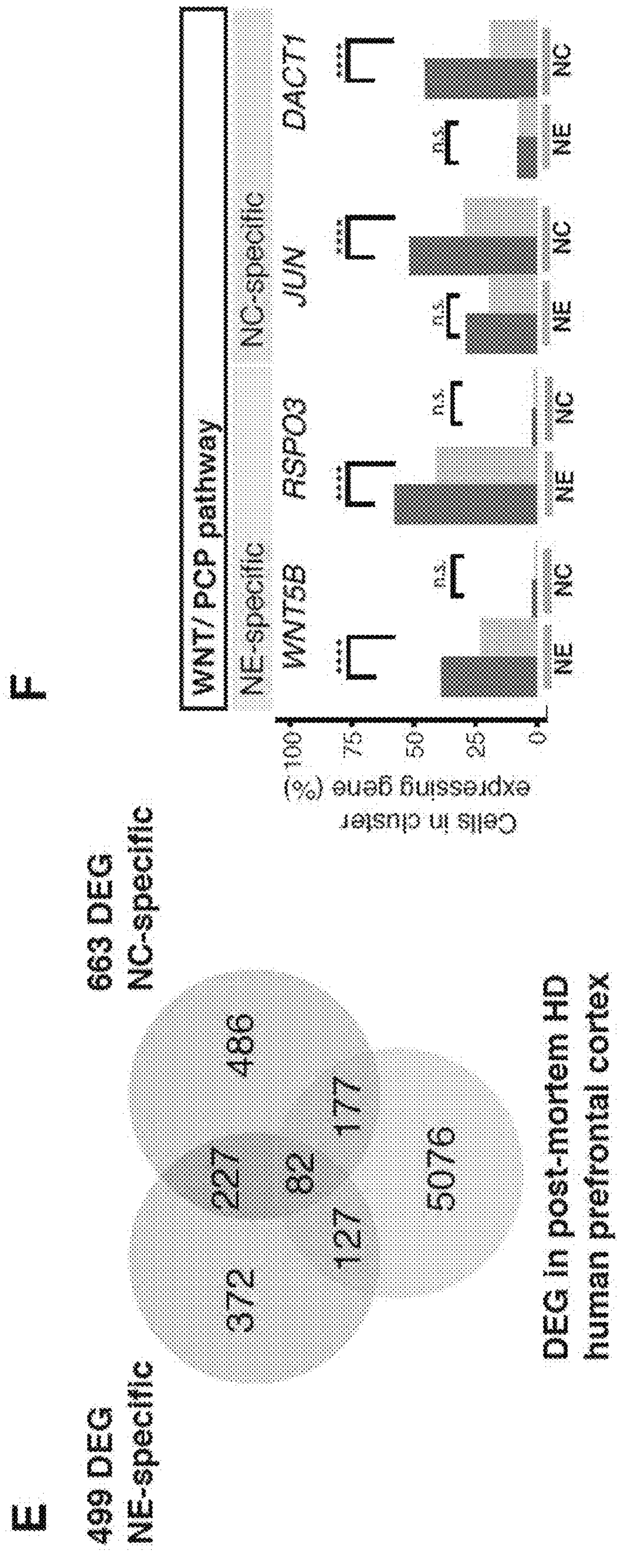
Figure 6:
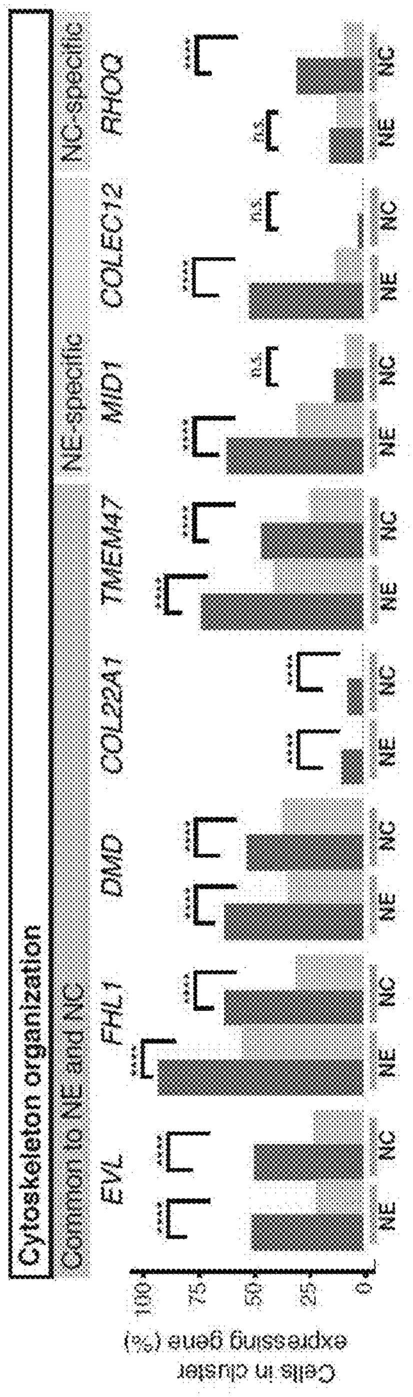

It has been shown that during neuruloid self-organization, PAX6 is first specified homogeneously before condensing into a central area. Defects in the PAX6 domain in the HD and Htt−/− neuruloid can therefore be due to differences in fate specification, morphogenesis or both. In order to distinguish between these three possibilities, the three-dimensional structure of neuruloids were examined first. In the HD background and in the Htt−/−, the PAX6 domain was extended and failed to close the central neuroepithelium (FIG. 6A-B). The extension of the PAX6 domain at day 4 and 5 during its specification phase was quantified, when its area linearly increases, and then at day 6, during the condensing phase of the neural population (FIG. 6C). While the induction of PAX6+ cells was similar across all the different genotypes at days 4 and 5, the HD lines carrying CAG expansion and the HTT−/− lines all showed impaired compaction at day 6 and failed to create the central closed neural-epithelium arrangement of the PAX6+ cells by day 7 (FIG. 6A-C). Overall, these results suggest that the patterning phenotype in the LID neuruloids is due to morphogenetic defects during the neural-epithelium condensing phase and not specification.

Figure 12:
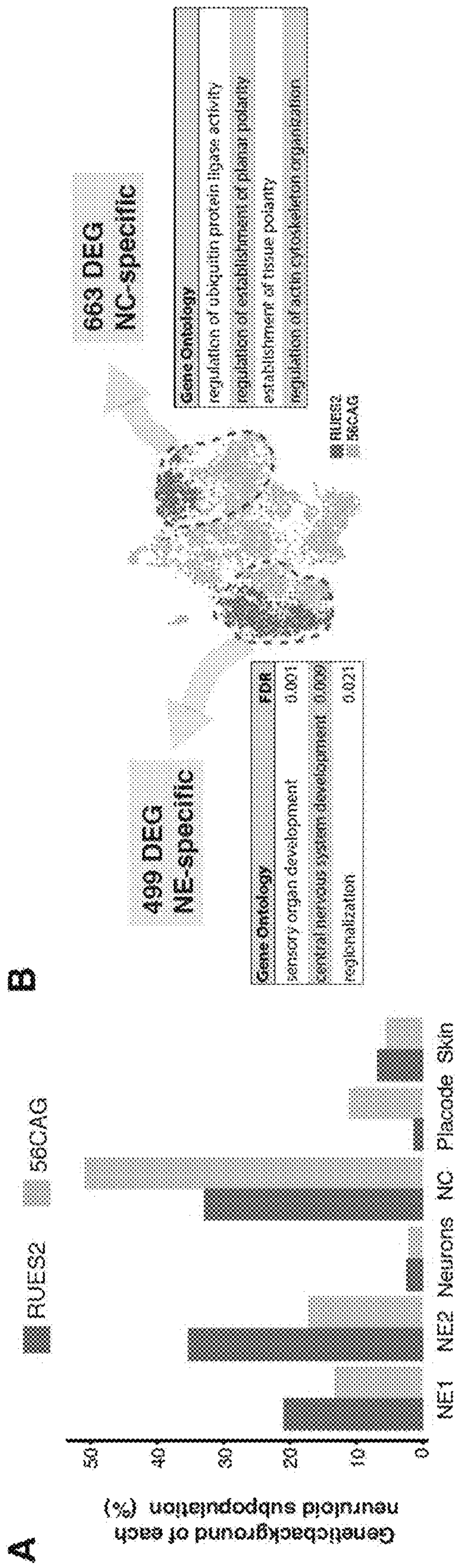
FIG. 12—related to FIG. 6. (A) RUES2 and 56 CAG background distribution within the main cell populations found in the neuruloid. All clusters are well represented in either background although 56 CAG has a higher relative proportion of NC and placode cells. (B) Gene ontology analyses using DAVID (www.david.ncifcrf.gov) for NE- and NC-specific DEG between RUES2 and 56 CAG. (C) Violin plots showing the distribution of normalized gene expression values for the genes in FIGS. 6B and 6C. (D) qPCR validation of the down-regulation of WNT/PCP and cytoskeleton-associated genes in the 56 CAG neuruloid versus WT RUES2. (E) Representative image of a day 7 neuruloid treated with Blebbistatin (5 μM) and stained for DAPI, N-CAD, PAX6, and COL4. (Top) side view, (Bottom) top view.
Figure 12:
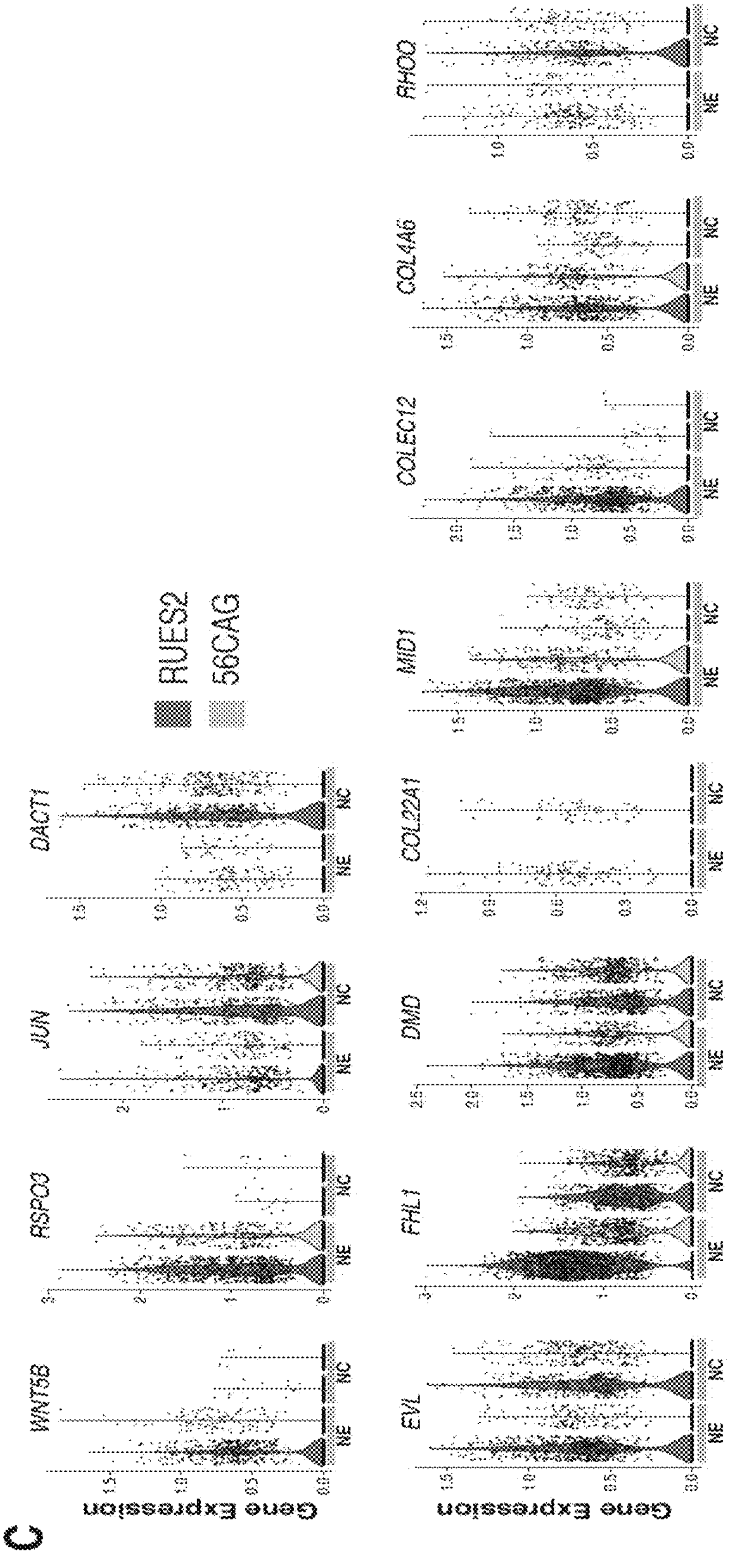
Figure 12:
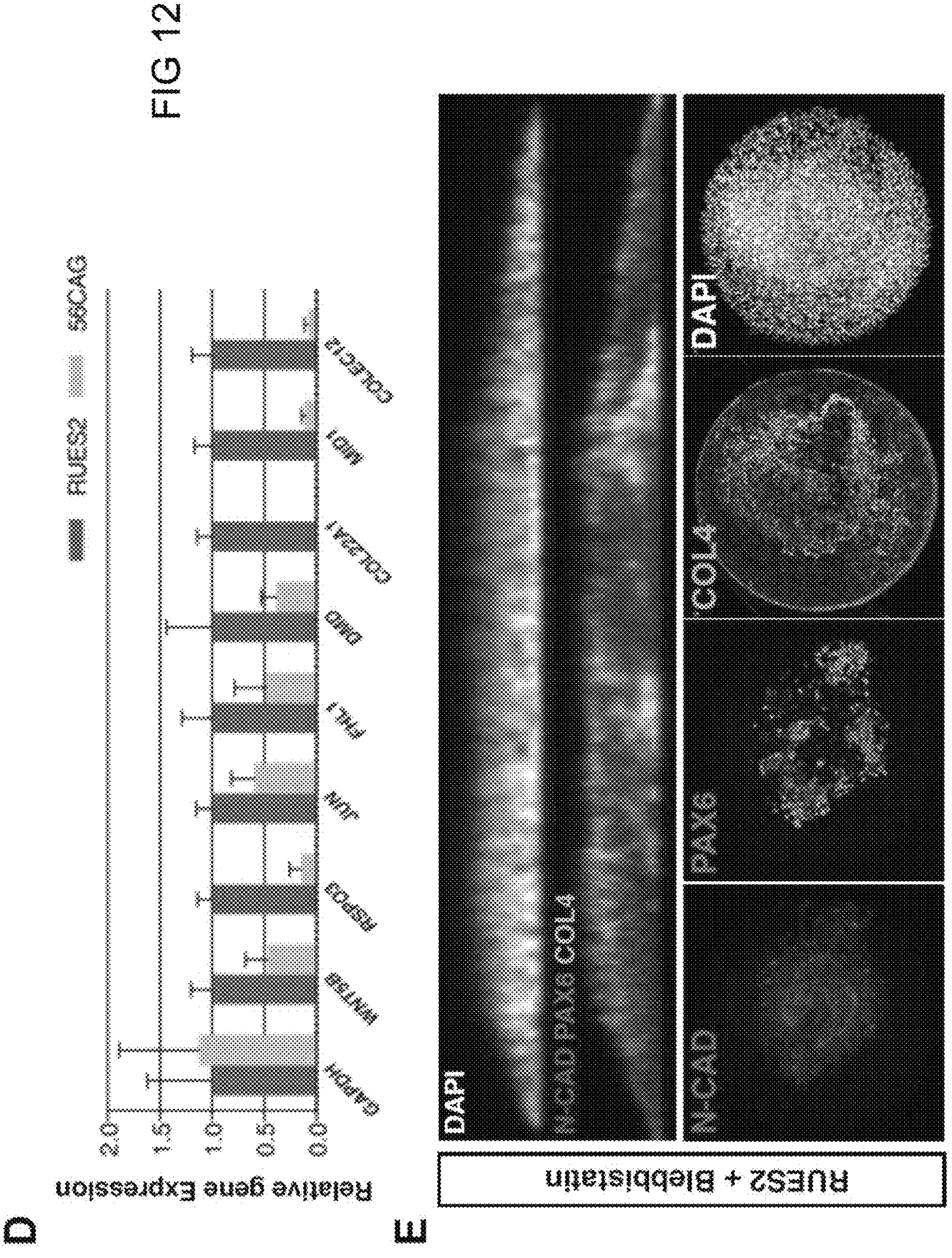

In order to unravel the molecular mechanisms underlying the morphogenetic defect, single-cell RNA-seq data of neuruloids in WT and 56 CAG background was explored. All major cell populations found in the WT neuruloid were also present in the 56 CAG background, supporting the lack of influence on fate specification (FIG. 12A). Comparison of the neural epithelium (NE) and neural crest (NC) population revealed that the HD cells segregate to occupy distinct areas in the t-SNE plot, suggesting distinct molecular signatures (FIG. 6D). Using Seurat to identify differentially expressed genes (DEG) between 56 CAG and RUES2 cell lines, 499 misregulated genes specific to the NE (adjusted p-value ≤0.05 and a minimum percentage difference in cells expressing the gene ≥10%) and 663 specific for the NC population was found (FIG. 6E). This provides the first molecular blueprint of HD in an isogenic background of a self-organizing human embryonic tissue. In this data-set, 26% of all DEG were overlapping with post-mortem HD brain samples (52) (FIG. 6E and FIG. 12B). Remarkably, evidence for WNT/PCP pathway down-regulation, e.g. WNT5B and RSPO3 in the NE and JUN and DACT1 in the NC was observed (FIG. 6F and FIG. 12C-D). A pronounced decline in the expression of cytoskeleton-associated genes and actin-myosin contraction: EVL, MID1, RHOQ, and TMEM47 was also observed (FIG. 6G). This highlights the morphogenetic defect observed in HD neuruloids and points towards actin-mediated tissue organization mechanism. This suggestion is supported by the observation that blebbistatin, an inhibitor of myosin II-dependent cell processes, phenocopies the opened neuro-epithelium observed in HD and Htt−/− neuruloids (FIG. 12E).

Discussion

Platforms for guided self-organization into standardized neural rosette and neuruloids, allowing in vitro quantitative dissection of the complex developmental steps associated with human neurulation are described herein. In both these assays, geometric confinement was a key driver for self-organization. In the context of neuruloid formation, the simple addition of a morphogen, BMP4, to a primed primitive ectoderm drives morphogenetic processes that lead to a layered, tri-dimensional structure comprising the four ectodermal cell types. This shows that relatively simple, well-timed signals are sufficient to harness the self-organizing properties of hESCs into biomimetic assemblies and opens a door towards solving molecular mechanisms that govern human ectodermal development. Moreover, it provides a highly robust and reproducible platform for understanding neural and pathological development, a goal that has yet to be reached by 3D organoids which display characteristic spatial organization of the brain at the cost of high variability.

The signalling requirements to specify all ectodermal compartments are still not understood, particularly for sensory placodes. While the four ectodennal derivatives can be created separately, their reproducible self-organization within the same tissue on micropatterns now offers a unique tool for precise dissection of the concerted interplay between signalling and fate acquisition. Of particular significance, it is shown that low BMP coupled with inhibition of WNT and FGF signalling is optimal for generation of human placodal cells from the primitive ectoderm.

Additionally, it is shown that BMP signalling in geometric confinement can lead to a complex morphogenetic event with neuroepithelium, cranial placodes, and neural crest cells organized in the radial plane, and early epidermal progenitors axially overlaying the neuroepithelium, as occurs during development. The mechanisms behind boundary formation in three dimensions are mostly unknown and can now be studied quantitatively in vitro.

At the signaling dynamic level, it is likely that the pulsed behaviour of pSMAD1 can be explained by a sub-cellular restriction of BMP receptors at the baso-lateral side of the center cells, which efficiently prevents ligand binding to its receptor at the colony center. Regarding the pre-pattern of PAX6+ cells observed after the dual-smad inhibition period, it is likely due to the increased contractile forces at the colony edge that have been shown to enhance BMP signaling in the absence of the ligand and therefore prevent small-molecule mediated neural induction at the colony edges.

Using scRNA-seq, we have now provided the first molecular signature of human neurulation and are able to map each cell population to a precise embryonic counterpart, the anterior cranial region of the human embryo. This knowledge paves the way for a detailed understanding of fate specification in humans and will lead to the discovery of human specific traits that have been ignored by studies in model systems.

Using a machine-learning algorithm, subtle phenotypic signatures associated with human neurodegenerative diseases is revealed, in this instance HD. Using deep neural networks with efficient parameter usage and heavy data augmentation, the disclosure provides that the networks can be trained efficiently even with a very low number of training images to solve the problem of inter-neuruloid variability. This enables a reproducible and quantitative dissection of self-organization that so far has not been successful in three-dimensional cultures.

These phenotypes rely on hESC multi-cellular self-organization and offer a tractable window into HD basic biology at early human embryonic stages, which remain experimentally challenging in vivo. Mutant HTT has been associated to a myriad of functions, making it difficult to identify the causal factors leading to the late-onset of HD. Furthermore, HTT has hominid-specific isoforms likely to result in additional functions undetectable in model organisms. Surprisingly, and despite multiple implications of HTT with cytoskeleton organization and neural tube defects in zebrafish, we still know very little about morphogenesis alterations during early development. These results now predict that human embryos carrying the HD genotype would show defect as early as neurulation stages through a loss of function mechanism, and tie together a molecular characterization with a functional phenotypic output. Such early defects could be responsible for the late onset associated with HD. The approach described herein has broad applicability, and paves the way for modelling a large number of diseases including neural tube defects and developmental disorders.

Methods

Cell Culture

All hESC lines were grown in HUESM medium that was conditioned with mouse embryonic fibroblasts and supplemented with 20 ng/ml bFGF (MEF-CM) (Deglincerti et al., 2016). Cells were tested for *Mycoplasma* at 2-month intervals. Cells were grown on tissue culture dishes coated with Geltrex (Life Technologies) solution.

Design of CRISPR/Cas9 and Homology Donors

For modification of the PAX6 and SOX10 loci, the Cas9 target sites were selected using an online resource (www.benchling.com/). pX335 (Addgene) was modified to include EGFP and PURO cassettes joined by 2A sequences to the N-terminal of Cas9. The resulting modified X335 was digested with Bbsl overnight. Oligomer annealing was carried out to introduce PAX6 and SOX10 sgRNA oligonucleotides into the modified X335 vector backbone. For creation of the homology donor plasmids, four or five fragment Gibson assembly was carried out with the Gibson Assembly Mastermix (New England Biolabs) using a vector to insert ratio of 1:3. Using this strategy, two homology donors were constructed: H2B-Citrine-P2A-PAX6 PGK::Puro(flox) and SOX10::H2B-tdTomato PGK::Neo(flox). In all cases, circular DNA was used for nucleofection of hESCs. Unless otherwise specified, the manufacturer's instructions were followed for all kits.

Generation of Transgenic hPSC Lines

Nucleofection was used to introduce DNA into hPSCs to generate the transgenic lines. The PAX6/SOX10 reporter line was created in the RUES2 background by sequential nucleofection and selection cycles. Early passage RUES2 cultures were pretreated for 1 hr with 10 μM ROCK-inhibitor and dissociated with Accutase (Stem Cell Technologies) for 15 min. Cells were counted and 2,000,000 cells resuspended in nucleofection solution L (Amaxa) together with the homology donors. Nucleofection was performed with program setting B-016 on an Amaxa Nucleofector II (Lonza). In the first round, 2 μg of H213-Citrine-P2A-PAX6 PGK::Puro(flox) homology donor was nucleofected together with 8 μg of a Cas9 nickase vector (X335) also containing sgRNA(PAX6). The cells were then grown and selected with puromycin. After 2 weeks of growth, clones were selected for further characterization by PCR genotyping, sequencing, karyotyping, and imaging upon ectodermal differentiation. One clone, which satisfied all criteria, was expanded and subjected a second round of nucleofection with 2 μg of the SOX10::H2B-tdTomato PGK::Neo(flox) homology donor and 8 μg of the sgRNA (SOX10) and Cas9 nickase vector (X335). The cells were grown and selected in neomycin for 14 days and clones were expanded for PCR genotyping. Out of the clones that had the correct integration, one clone was chosen for further experiments, expanded, characterized, and frozen down. Antibiotic selection was typically started at day 4 after nucleofection. When needed, the following concentrations of antibiotics were used: 2 μg/mL of puromycin and 200 μg/mL G418. Selected colonies could be seen within 2-5 days after antibiotic initiation. Media was changed for 8-10 days in the presence of selection. Individual colonies were then picked under an IVF hood, broken up by pipetting, and plated on to Matrigel coated plates. All clones were karyotyped after expansion to ensure chromosomal stability after genetic modification(s).

Micropatterned Cell Culture

Micropatterned glass cover slips (CYTOOCHIPS™ Arena A, Arena 500 A, Arena EMB A) were first coated with 100 μg/ml of recombinant Laminin-521 (BioLamina, LN521-03) diluted in PBS+/+(gibco) for 3 h at 37° C. To do that, place micropatterns face-up on to a Parafilm that seated in 10 cm dish then put 800 μl laminin solution on to the micropattern. After 3 h at 37° C., transfer the coated micropattern to 35 mm dish with 5 ml of PBS+/+. Laminin was then removed with six serial dilutions in PBS+/+ (dilution 1:4) before two complete washes in PBS+/+. Then the coated micropattern was kept in PBS+/+ at 37° C. Cells were seeded as follows. Cells growing in MEF-CM on culture dish were washed once with PBS−/− (gibco), then treated with Accutase (Stem Cell Technologies) for 5 min. Cells were then triturated with a pipet to ensure single cell suspension and Accutase was diluted out with 4×HUESM medium supplemented with 20 ng/ml bFGF and Rock inhibitor Y27632 (10 μM, Abcam ab120129). Cells were then further diluted with the same medium and $5\times10^5$ (or as indicated) cells in 3.0 ml of medium were placed over the micropattern in a 35 mm tissue culture dish, then incubated at 37° C. After 3 h, the micropattern in a dish was washed once with PBS+/+. For SB+LDN condition: PBS+/+ was replaced with 3N medium (Shi et al., 2012) with 10 μM SB431542 (Stemgent 04-0010-10) and 0.2 μM LDN 193189 (Stemgent 04-0019). At Day 3 and 5, the medium was replaced with the same fresh medium and incubated at 37° C. until day 7. For SB+BMP4 condition (neuruloid), PBS was replaced with HUESM with 10 μM SB431542 and 0.2 μM LDN 193189. At Day 3, the medium was replaced with HUESM with 10 μM SB431542 and BMP4 (50 ng/ml or indicated each experiment). At Day 5, the medium was replaced with the same fresh medium then incubated until day 7.

Immunofluorescence

Micropattern coverslips were fixed with 4% paraformaldehyde (Electron Microscopy Sciences 15713) in warm medium for 30 min, rinsed three times with PBS−/−, and then blocked and permeabilized with 3% normal donkey serum (Jackson Immunoresearch 017-000-121) with 0.5% Triton X-100 (Sigma 93443) in PBS−/− for 30 min. Micropatterns were incubated with primary antibodies for 1.5 h, washed three times in PBS−/− for 5 min each, incubated with secondary antibodies conjugated with Alexa 488, Alexa 555, Alexa 594 or Alexa 647 (1/1000 dilution, Molecular Probes) and 10 ng/ml of 4',6-diamidino-2-phenylin-dole (DAPI, Thermo Fisher Scientific D1306) for 30 min and then washed two times with PBS−/−. For double staining with antibodies from the same species, Alexa 488 Fab fragments (Jackson Immunoresearch, 715-547-003) and Fab fragment IgG (Jackson Immunoresearch, 715-007-003) were used. Coverslips were mounted on slides using ProLong Gold antifade mounting medium (Molecular Probes P36934).

Imaging

All confocal images were acquired on a Zeiss Inverted LSM 780 laser scanning confocal microscope with a 10×, 20× or 40× water-immersion objective. 3D visualization and rendering was performed using Imaris software. Live reporter imaging was performed with spinning disk microscope (CellVoyager CV1000, Yokogawa).

Single-Cell RNA Sequencing (scRNA-Seq)

Two micropatterned glass cover slips with 500 μm of diameter neuruloids (BMP4 3 ng/ml) were grown in parallel using RUES2 hESCs and the isogenic 56 CAG HD line. At day 7, approximately half of each cover slip with neuruloids was scraped off and treated with Accutase (Stemcell technologies) for 10 min at 37° C. The remaining neuruloids on the cover slip were fixed for immunofluorescence analysis as quality control. After dissociation the cells were washed three times in PBS+/+(gibco) with 0.04% BSA and strained through a Flowmi tip strainer (40 μm, cat. no. 136800040).

Cell count and viability were determined on a Countess II Automated Cell Counter using trypan blue. The two samples were separately loaded for capture with the Chromium System using the Single Cell 3' v2 reagents (10× Genomics). Following cell capture and lysis, cDNA was synthesized and amplified according to the manufacturer's instructions (10× Genomics). The resulting libraries were sequenced on the Illumina NextSeq500 platform with 150-cycle high output. The Cell Ranger (v2.0.2) software pipeline was used to create FASTQ files which were aligned to the hg19 genome using default parameters. Filtered gene expression matrices of genes versus detected barcodes (cells) with counts of unique molecular identifiers (UMI) were generated and subsequently used for downstream analyses. These data are available through the NCBI GEO accession number GSE118682.

scRNA-Seq and Differential Gene Expression Analysis

UMI count matrices for RUES2 and 56 CAG were loaded into R (v3.5.1) and analysed using Seurat(v2.3.4) components unless stated otherwise. The raw matrices were filtered to have a minimum of 200 detected genes per cell and a gene was only kept if expressed (non-zero) in at least 3 cells. Cells with over 5% mitochondrial UMIs were discarded. To directly compare between data sets, RUES2 and 56 CAG data were merged into a single Seurat object and log-normalized to a total of 1e4 molecules. Principal component analysis (PCA) was performed after scaling the data to minimize the contributions of cell cycle, as well as the total number of detected UMIs and the percentage of mitochondrial gene content. Only 1,601 high variable genes were used as input for PCA. To unbiasedly find clusters the Louvain algorithm with multilevel refinement with a resolution parameter of 0.6 and using the first 15 PCA dimensions was employed. Clustering, genetic background and gene expression (normalized UMI counts) were visualized in a low-dimensional space using t-SNE plots with a perplexity parameter of 50 and using 15 PCA dimensions.

Marker genes for each cluster were found using the Wilcoxon rank sum test whose results were subsequently filtered for an adjusted p-value <0.05 and a minimum of 20% cells expressing the gene in the cluster of interest. Genes were ordered according to the difference in percentage of expressing cells between the cluster and the rest of the population. Percentage differences down to 10% were considered. The same strategy was used to find differentially expressed genes between RUES2 and 56 CAG within NE and NC clusters. Two sets were considered: one with percentage differences ≥10% and a more stringent set requiring percentage differences in expressing cells ≥25% between RUES2 and 56 CAG cells.

Image Analysis—Neural Network

Identification of the N-Cadherin positive lumen, PAX6 area and collagen IV around the rosette was unreliable using standard segmentation methods, either based on thresholds, or machine learning techniques such as training a filter-based pixel classifier using Ilastik [Ilastik: Interactive Learning and Segmentation Toolkit, C. Sommer, C. Strähle, U. Köthe, F. A. Hamprecht, Eighth IEEE International Symposium on Biomedical Imaging (ISBI). Proceedings, (2011), 230-233]. There are several factors complicating the correct segmentation, such as significant amount of background staining and strong variability of the features. For example, it was found that in many cases high intensity-patches of N-Cadherin were misidentified as a lumen, which can even have a lower intensity than some of the background. Making the classifier less sensitive to such additional patches results in it missing some lumen completely. Some examples of correct and incorrect classifications using Ilastik are shown in FIG. 11B, in the central columns.

To improve segmentation, deep convolutional neural networks was used, since in recent years these have been shown to excel at complex segmentation tasks, and are the state of the art for the type of imaging problems described above. Deep convolutional dense nets with 103 layers were trained [Jegou, Simon and Drozdzal, Michal and Vazquez, David and Romero, Adriana and Bengio, Yoshua, The One Hundred Layers Tiramisu: Fully Convolutional DenseNets for Semantic Segmentation, arxiv.org/abs/1611.09326, 2016], adapted for usage with a single channel and written in PyTorch [pytorch.org/], for segmentation of each of the three features. This network was chosen this network as it performs particularly well on segmentation tasks while having very efficient parameter usage, thus reducing the number of parameters that have to be optimized. Data including 100 hand-segmented images randomly chosen from WT and CAG expanded lines was used for training. Increasing the number of training data by data augmentation such as rotation, flipping and random cropping was crucial for reducing the generalization error of the network. The Adam optimization scheme was used [Kingma, D. and Ba, J. (2015) Adam A Method for Stochastic Optimization, Proceedings of the 3rd International Conference on Learning Representations (ICLR 2015)] with a learning rate of 0.0001 and trained the network for 1000 epochs on a standard desktop computer with an Nvidia GeForce GTX 1080 Ti graphics card. It was found that the trained network was almost perfect at segmenting unseen data, as shown for the case of the lumen segmentation, and significantly outperformed filter-based machine learning classifiers, FIG. 11B.

Quantitative PCR: For quantitative PCR (qPCR) experiments, total RNAs were isolated using RNeasy Plus Mini kits (QIAGEN 74134). cDNAs were prepared using Transcriptor First Strand cDNA Synthesis Kit (Roche 04897030001). qPCRs were performed for 45 cycles, 55° C. annealing temperature using Lightcycler 480 instrument and SYBR Green Master Mix (Roche 04887352001). ATP5O was used for internal normalization. PCR primer sequences:

| | | |
|---|---|---|
| ATP5O | ACTCGGGTTTGACCTACAGC (SEQ ID NO: 1) | GGTACTGAAGCATCGCACCT (SEQ ID NO: 2) |
| OCT4 | CAAGCTCCTGAAGCAGAAGAGGAT (SEQ ID NO: 3) | CTCACTCGGTTCTCGATACTGGTT (SEQ ID NO: 4) |
| PAX6 | TCACCATGGCAAATAACCTG (SEQ ID NO: 5) | CAGCATGCAGGAGTATGAGG (SEQ ID NO: 6) |
| OTX2 | GCTGGCTATTTGGAATTTAAAGG (SEQ ID NO: 7) | GGGTTTGGAGCAGTGGAAC (SEQ ID NO: 8) |
| LHX2 | TTACGGCAGGAAAACACGG (SEQ ID NO: 9) | TGCCAGGCACAGAAGTTAAG (SEQ ID NO: 10) |
| FOXG1 | AGAAGAACGGCAAGTACGAGA (SEQ ID NO: 11) | TGTTGAGGGACAGATTGTGGC (SEQ ID NO: 12) |
| PLZF | CCTTTGTCTGTGATCAGTGCG (SEQ ID NO: 13) | CAGTG CCAGTATGGGTCTGC (SEQ ID NO: 14) |

-continued

| | | |
|---|---|---|
| NNAT | ACTGGGTAGGATTCGCTTTTCG (SEQ ID NO: 15) | ACACCTCACTTCTCGCAATGG (SEQ ID NO: 16) |
| COLEC12 | AATCCTTCGGTTACAAGCGGT (SEQ ID NO: 17) | ACTGTGATTGTTAGCAAGGCAC (SEQ ID NO: 18) |
| LY6E | GCCATCCTCTCCAGAATGAA (SEQ ID NO: 19) | GCAGGAGAAGCACATCAGC (SEQ ID NO: 20) |
| FHL1 | CAGCAGCGGGAGAGAAGTC (SEQ ID NO: 21) | CCAGTAGAGCCAGTGAATCCT (SEQ ID NO: 22) |
| DMD | GTGTGTCAACCTGTCTATCAAGG (SEQ ID NO: 23) | CATGGCATCGTAGAAGTGGAAG (SEQ ID NO: 24) |
| MID1 | CGCACCATCTCATGCCATGT (SEQ ID NO: 25) | CGGGCGGTCACTATCTTGT (SEQ ID NO: 26) |
| RHOB | GGGGCTTATCCGCACTTACC (SEQ ID NO: 27) | TGGCCTGATACTCGGTGAACA (SEQ ID NO: 28) |
| COL4A6 | CAGCAGCGGGAGAGAAGTC (SEQ ID NO: 29) | CCAGTAGAGCCAGTGAATCCT (SEQ ID NO: 30) |
| COL22A1 | TCCGACTTCAATGCCATCGAC (SEQ ID NO: 31) | TACACGAACGCTAGGACAGAG (SEQ ID NO: 32) |
| WNT5B | GCTTCTGACAGACGCCAACT (SEQ ID NO: 33) | CACCGATGATAAACATCTCGGG (SEQ ID NO: 34) |
| RSPO3 | TGTGCAACATGCTCAGATTACA (SEQ ID NO: 35) | TGCTTCATGCCAATTCTTTCCA (SEQ ID NO: 36) |
| JUN | TGTACCGACTGAGAGTTCTTGA (SEQ ID NO: 37) | ACAGAGCGAGTGAAAATGTGTAT (SEQ ID NO: 38) |
| CD81 | GCGCCCAACACCTTCTATGTA (SEQ ID NO: 39) | CCAGGAAGCCAACGAACATCA (SEQ ID NO: 40) |
| PUS7L | TGCAGTGCTGGTAATCCGAAT (SEQ ID NO: 41) | AACCAATCGCTTCAAACATTTCC (SEQ ID NO: 42) |
| MITF | GAAATCTTGGGCTTGATGGA (SEQ ID NO: 43) | AGGAGTTGCTGATGGTGAGG (SEQ ID NO: 44) |

Statistical analysis: Statistical analyses were performed by one-way ANOVA with multiple comparison with Tukey's method using Prism 7 software (ns P>0.05, * P<0.05,  P<0.01, * P<0.001, **** P<0.00001).

Antibodies

| NAME | ANTIBODY TYPE | SOURCE | DILUTION |
|---|---|---|---|
| PAX6 | Rabbit Polyclonal | BioLegend 901301 | 1:300 |
| OTX2 | Goat Polyclonal | R&D AF1979 | 1:250 |
| SOX10 | Goat Polyclonal | R&D AF2864 | 1:50 |
| N-CAD | Mouse monoclonal | BioLegend 350802 | 1:200 |
| PAR3 | Rabbit Polyclonal | EMD Millipore 07-330 | 1:200 |
| aPKC | Goat Polyclonal | Santa Cruz Biotechnology sc-216 | 1:200 |
| ZO-1 | Rabbit Polyclonal | Thermo Fisher Scientific 61-7300 | 1:200 |
| OCT4 | Goat Polyclonal | Santa Cruz Biotechnology sc-8628 | 1:400 |
| SIX1 | Rabbit Monoclonal | Cell signaling 12891 | 1:200 |
| TFAP2A | Mouse monoclonal | DSHB 3B5 | 1:200 |
| COL4 | Rabbit Polyclonal | Abcam ab6586 | 1:200 |
| KRT18 | Mouse monoclonal | Abcam ab668 | 1:600 |

-continued

| NAME | ANTIBODY TYPE | SOURCE | DILUTION |
|---|---|---|---|
| STMN2 | Rabbit Polyclonal | Thermo Fisher Scientific 720178 | 1:500 |
| GATA3 | Mouse monoclonal | MA1-028 | 1:200 |
| pSMAD1/5 | Rabbit Polyclonal | 9516 | 1:200, 1:500 (for Western blot) |
| Total SMAD1 | Rabbit monoclonal | 6944 | 1:1000 (for Western blot) |

1 Ozair, M. Z., Kintner, C. & Brivanlou, A. H. Neural induction and early patterning in vertebrates. Wiley interdisciplinary reviews. *Developmental biology* 2, 479-498, doi:10.1002/wdev.90 (2013).
2 Chambers, S. M. et al. Highly efficient neural conversion of human ES and iPS cells by dual inhibition of SMAD signaling. *Nature biotechnology* 27, 275-280, doi: nbt.1529 [pii]10.1038/nbt.1529 (2009).
3 Ozair, M. Z., Noggle, S., Warmflash, A., Krzyspiak, J. E. & Brivanlou, A. 1-1. SMAD7 directly converts human embryonic stem cells to telencephalic fate by a default mechanism. *Stem cells* 31, 35-47, doi:10.1002/stem.1246 (2013).
4 Dincer, Z. et al. Specification of functional cranial placode derivatives from human pluripotent stem cells. *Cell reports* 5, 1387-1402, doi:10.1016/j.ceirep.2013.10.048 (2013).
5 Tchieu, J. et al. A Modular Platform for Differentiation of Human PSCs into All Major Ectodermal Lineages. *Cell stem cell* 21, 399-410 e397, doi:10.1016/j.stem.2017.08.015 (2017).
6 Hemmati-Brivanlou, A. & Melton, D. A. Inhibition of activin receptor signaling promotes neuralization in *Xenopus. Cell* 77, 273-281 (1994).
7 Munoz-Sanjuan, 1. & Brivanlou, A. H. Neural induction, the default model and embryonic stem cells. *Nature reviews. Neuroscience* 3, 271-280, doi:10.1038/nrn786 (2002).
8 Wilson, P. A., Lagna, G., Suzuki, A. & Hemmati-Brivanlou, A. Concentration-dependent patterning of the *Xenopus* ectoderm by BMP4 and its signal transducer Smad1. *Development* 124, 3177-3184 (1997).
9 Bhattacharyya, S. & Bronner-Fraser, M. Hierarchy of regulatory events in sensory placode development. *Curr Opin Genet Dev* 14, 520-526, doi:10.1016/j.gde.2004.08.002 (2004).
10 Litsiou, A., Hanson, S. & Streit, A. A balance of FGF, BMP and WNT signalling positions the future placode territory in the head. *Development* 132, 4051-4062, doi: 10.1242/dev.01964 (2005).
11 Sauka-Spengler, T. & Bronner-Fraser, M. A gene regulatory network orchestrates neural crest formation. *Nature reviews. Molecular cell biology* 9, 557-568, doi:10.1038/nrm2428 (2008).
12 Betancur, P., Bronner-Fraser, M. & Sauka-Spengler, T. Genomic code for Sox10 activation reveals a key regulatory enhancer for cranial neural crest. *Proc Natl Acad Sci USA* 107, 3570-3575, doi:10.1073/pnas.0906596107 (2010).
13 Kwon, H. J., Bhat, N., Sweet, E. M., Cornell, R. A. & Riley, B. B. Identification of early requirements for preplacodal ectoderm and sensory organ development. *PLoS genetics* 6, e1001133, doi:10.1371/journal.pgen.1001133 (2010).
14 Schlosser, G. Early embryonic specification of vertebrate cranial placodes. *Wiley interdisciplinary reviews. Developmental biology* 3, 349-363, dci:10.1002/wdev.142 (2014).
15 Stuhlmiller, T. J. & Garcia-Castro, M. I. FGF/MAPK signaling is required in the gastrula epiblast for avian neural crest induction. *Development* 139, 289-300, dci: 10.1242/dev.070276 (2012).
16 Reichert, S., Randall, R. A. & Hill, C. S. A BMP regulatory network controls ectodermal cell fate decisions at the neural plate border. *Development* 140, 4435-4444, doi:10.1242/dev.098707 (2013).
17 Patthey, C. & Gunhaga, L. Signaling pathways regulating ectodermal cell fate choices. *Experimental cell research* 321, 11-16, doi:10.1016% j.yexcr.2013.08.002 (2014).
18 Leung, A. W. et al. WNT/beta-catenin signaling mediates human neural crest induction via a pre-neural border intermediate. *Development* 143, 398-410, doi:10.1242/dev.130849 (2016).
19 Greenberg, F. DiGeorge syndrome: an historical review of clinical and cytogenetic features. *Journal of medical genetics* 30, 803-806 (1993).
20 Roizen, N. J. & Patterson, D. Down's syndrome. *Lancet* 361, 1281-1289, doi:10.1016/S0140=6736(03)12987-X (2003).
21 Sarkozy, A., Digilio, M. C. & Dallapiccola, B. Leopard syndrome. *Orphanet journal of rare diseases* 3, 13, doi: 10.1186/1750-1172-3-13 (2008).
22 Ferner, R. E. Neurofibromatosis 1. *European journal of human genetics: EJHG* 15, 131-138, doi:10.1038/sj.ejhg.5201676 (2007).
23 Greene, N. D. & Copp, A. J. Neural tube defects. *Annual review of neuroscience* 37, 221-242, doi:10.1146/annurev-neuro-062012-170354 (2014).
24 Elkabetz, Y. et al. Human ES cell-derived neural rosettes reveal a functionally distinct early neural stem cell stage. *Genes & development* 22, 152-165, doi:10.1101/gad.1616208 (2008).
25 Ozair, M. Z. et al. hPSC Modeling Reveals that Fate Selection of Cortical Deep Projection Neurons Occurs in the Subplate. *Cell stem cell* 23, 60-73 e66, doi:10.1016/j.stem.2018.05.024 (2018).
26 Warmflash, A., Sorre, B., Etoc, F., Siggia, E. D. & Brivanlou, A. H. A method to recapitulate early embryonic spatial patterning in human embryonic stern cells. *Nat Methods* 11, 847-854, doi:nmeth.3016 [pii]10.1038/nmeth.3016 (2014).
27 Deglincerti, A., Etoc, F., Ozair, M. Z. & Brivanlou, A. H. Self-Organization of Spatial Patterning in Human Embryonic Stein Cells. *Current topics in developmental biology* 116, 99-113, doi:10.1016/bs.ctdb.2015.11.010 (2016).
28 Etoc, F, et al. A Balance between Secreted Inhibitors and Edge Sensing Controls Gastruloid Self-Organization. *Dev Cell*, doi:10.1016/j.deveel.2016.09.016 (2016).
29 Grenningloh, G., Soehrman, S., Bondallaz, P., Ruchti, E. & Cadas, H. Role of the microtubule destabilizing proteins SCG10 and stathmin in neuronal growth. *Journal of neurobiology* 58, 60-69, doi:10.1002/neu.10279 (2004).
30 Mallika, C., Guo, Q. & Li, J. Y. Gbx2 is essential for maintaining thalamic neuron identity and repressing habenular characters in the developing thalamus. *Developmental biology* 407, 26-39, doi:10.1016/j.ydbio.2015.08.010 (2015).
31 Quina, L. A., Wang, S., Ng, L. & Turner, E. E. Brn3a and Nurr1 mediate a gene regulatory pathway for habenula development. *The Journal of neuroscience: the official*

*journal of the Society for Neuroscience* 29, 14309-14322, doi:10.1523/JNEUROSCI.2430-09.2009 (2009).

32 Hikosaka, O. The habenula: from stress evasion to value-based decision-making. *Nature reviews. Neuroscience* 11, 503-513, doi:10.1038/nrn2866 (2010).

33 Inoue, T., Chisaka, O., Matsunami, H. & Takeichi, M. Cadherin-6 expression transiently delineates specific rhombomeres, other neural tube subdivisions, and neural crest subpopulations in mouse embryos. *Developmental biology* 183, 183-194, doi:10.1006/dbio.1996.8501 (1997).

34 Van de Putte, T. et at. Mice lacking ZFHX1B, the gene that codes for Smad-interacting protein-1, reveal a role for multiple neural crest cell defects in the etiology of Hirschsprung disease-mental retardation syndrome. American journal of human genetics 72, 465-470, doi: 10.1086/346092 (2003).

35 Bolos, V. et al. The transcription factor Slug represses E-cadherin expression and induces epithelial to mesenchymal transitions: a comparison with Snail and E47 repressors. *Journal of cell science* 116, 499-511 (2003).

36 Huang, M. et alt Generating trunk neural crest from human pluripotent stem cells. *Scientific reports* 6, 19727, doi:10.1038/srep19727 (2016).

37 Bhatt, S., Diaz, R. & Trainor, P. A. Signals and switches in Mammalian neural crest cell differentiation. *Cold Spring Harbor perspectives in biology* 5, doi:10.1101/cshperspect.a008326 (2013).

38 Ma, Q., Chen, Z., del Barco Barrantes, L., de la Pompa, J. L. & Anderson, D. J. neurogenin1 is essential for the determination of neuronal precursors for proximal cranial sensory ganglia. *Neuron* 20, 469-482 (1998).

39 Bae, S., Bessho, Y., Hojo, M. & Kageyarna, R. The bHLH gene Hes6, an inhibitor of Hes1, promotes neuronal differentiation. *Development* 127, 2933-2943 (2000).

Byrne, C., Tainsky, M. & Fuchs, E. Programming gene expression in developing epidermis. *Development* 120, 2369-2383 (1994).

41 Moll, R., Divo, M. & Langbein, L. The human keratins: biology and pathology. *Histochemistry and cell biology* 129, 705-733, doi:10.1007/s00418-008-0435-6 (2008).

42 Arabzadeh, A., Troy, T. C. & Turksen, K. Role of the Cldn6 cytoplasmic tail domain in membrane targeting and epidermal differentiation in vivo. *Molecular and cellular biology* 26, 5876-5887, doi:10.1128/MCB.02342-05 (2006).

43 Kaufman, C. K. et al. GATA-3: an unexpected regulator of cell lineage determination in skin. *Genes & development* 17, 2108-2122, doi:10.1101/gad.1115203 (2003).

44 Lavery, D. L., Davenport, L. R., Turnbull, Y. D., Wheeler, G. N. & Hoppler, S. Wnt6 expression in epidermis and epithelial tissues during *Xenopus* organogenesis. *Developmental dynamics: an official publication of the American Association of Anatomists* 237, 768-779, doi:10.1002/dvdy.21440 (2008).

45 Onorati, M. et al. Molecular and functional definition of the developing human striatum. *Nature neuroscience* 17, 1804-1815, doi:10.1038/nn.3860 (2014).

46 Lo Sardo, V. et al. An evolutionary recent neuroepithelial cell adhesion function of huntingtin implicates ADAM10-Neadherin. *Nature neuroscience* 15, 713-721, doi: 10.1038/nn.3080 (2012).

47 Conforti, P. et al. Faulty neuronal determination and cell polarization are reverted by modulating HD early phenotypes. *Proc Natl Acad Sci USA* 115, E762-E771, doi: 10.1073/pnas.1715865115 (2018).

48 Ruzo, A. et al. Chromosomal instability during neurogenesis in Huntington's disease. *Development* 145 (2018).

49 Shelhamer, E., Long, J. & Darrell, T. Fully Convolutional Networks for Semantic Segmentation. *IEEE transactions on pattern analysis and machine intelligence* 39, 640-651, doi:10.1109/TPAMI.2016.2572683 (2017).

50 Barnat, M., Le Friec, J., Benstaali, C. & Humbert, S. Huntingtin-Mediated Multipolar-Bipolar Transition of Newborn Cortical Neurons Is Critical for Their Postnatal Neuronal Morphology. *Neuron* 93, 99-114, doi:10.1016/j.neuron.2016.11.035 (2017).

51 Butler, A., Hoffman, P., Smibert, P., Papalexi, E. & Satija, R. Integrating single-cell transcriptomic data across different conditions, technologies, and species. *Nature biotechnology* 36, 411-420, doi:10.1038/nbt.4096 (2018).

52 Labadorf, A. et al. RNA Sequence Analysis of Human Huntington Disease Brain Reveals an Extensive Increase in Inflammatory and Developmental Gene Expression. *PloS one* 10, e0143563, doi:10.1371/journal-pone.0143563 (2015).

53 Lancaster, M. A. & Knoblich, J. A. Organogenesis in a dish: modeling development and disease using organoid technologies. *Science* 345, 1247125, doi:10.1126/science.1247125 (2014).

54 Lancaster, M. A. et al. Cerebral organoids model human brain development and microcephaly. *Nature* 501, 373-379, doi:10.1038/nature12517 (2013).

55 Xue, X. et al. Mechanics-guided embryonic patterning of neuroectoderm tissue from human pluripotent stem cells. *Nature materials* 17, 633-641, doi:10.1038/s41563-018-0082-9 (2018).

56 Labbadia, J. & Morimoto, R. 1. Huntington's disease: underlying molecular mechanisms and emerging concepts. *Trends in biochemical sciences* 38, 378-385, doi: 10.1016/j.tibs.2013.05.003 (2013).

57 Landles, C. & Bates, G. P. Huntingtin and the molecular pathogenesis of Huntington's disease. Fourth in molecular medicine review series. *EMBO reports* 5, 958-963, doi:10.1038/sj.embor.7400250 (2004).

58 Ruzo, A. et al. Discovery of novel isoforms of huntingtin reveals a new hominid-specific exon. *PloS one* 10, e0127687, doi:10.1371/journal.pone.0127687 (2015).

59 Tourette, C. et al. A large scale Huntingtin protein interaction network implicates Rho GTPase signaling pathways in Huntington disease. *The Journal of biological chemistry* 289, 6709-6726, doi:10.1074/jbc.Mi 13.523696 (2014).

60 Caviston, J. P. & Holzbaur, E. L. Huntingtin as an essential integrator of intracellular vesicular trafficking. *Trends in cell biology* 19, 147-155, doi:10.1016/j.teb.2009.01.005 (2009).

61 Molero, A. E. et al. Selective expression of mutant huntingtin during development recapitulates characteristic features of Huntington's disease. *Proc Natl Acad Sci USA* 113, 5736-5741, doi:10.1073/pnas.1603871113 (2016).

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A method of forming a neural ectodermal lineage cellular structure, comprising:

(a) culturing mammalian stem cells seeded on a circular micropattern substrate under conditions of dual SMAD inhibition for a period of 3 days to 10 days, such that a colony which comprises neural progenitor cells and a lumen and which displays radial organization is formed; and (b) culturing the colony in the presence of a bone morphogenetic protein (BMP) under conditions under which neurulation occurs, thereby forming a disc-shaped neural ectodermal lineage cellular structure which comprises (i) neuroepithelial cells surrounding the lumen, (ii) sensory placodes, (iii) neural crest cells, and (iv) epidermal cells, wherein: the mammalian stem cells are pluripotent stem cells;

the dual SMAD inhibitors are a BMP inhibitor having a concentration range of 0.1 μM to 0.5 μM and a transforming growth factor beta (TGF-β) inhibitor having a concentration range of 0.1 μM to 20 μM:

the BMP of step (b) is a BMP4 at a concentration range of 1 to 100 ng/mL; and the mammalian stem cells are seeded at a density of 500 to 5000 cells per circular micropattern.

2. The method of claim 1, wherein the cells in the center of the colony produced in step (a) express N-CAD.

3. The method of claim 1, wherein the neural ectodermal lineage cellular structure produced in step (b) is 150 μm to 1000 μm in diameter.

4. The method of claim 3, wherein the neural ectodermal lineage cellular structure is 10 μm-100 μm in height.

5. The method of claim 1, wherein the neuroepithelial cells, sensory placodes, neural crest cells, and epidermal cells are radially organized and/or spatially segregated.

6. The method of claim 1, wherein:

(a) the neuroepithelial cells are innermost in the structure and surround the lumen;

(b) the neural crest cells are adjacent to and around the neuroepithelial cells;

(c) the sensory placodes are within and surrounded by the neural crest cells; and (d) the epidermal cells are the outermost cells of the structure and axially overlay the other cell types in the neural ectodermal lineage cellular structure.

7. The method of claim 1, wherein the epidermal cells are arranged in a single layer.

8. The method of claim 1, wherein step (a) comprises culturing the mammalian stem cells in a first medium comprising two SMAD inhibitors.

9. The method of claim 8, wherein the method further comprises the step of removing the first medium between steps (a) and (b) and/or wherein step (b) comprises culturing the cells produced in step (a) in a second medium comprising the BMP4.

10. The method of claim 1, wherein step (b) comprises culturing the cells produced in step (a) in the presence of a TGF-β inhibitor in addition to the BMP4.

11. The method of claim 1, where in the mammalian stem cells are normal cells.

12. The method of claim 1, where in the mammalian stem cells have one or more mutations associated with a disease or condition.

13. The method of claim 12, wherein the mammalian stem cells have one or more mutations associated with a neurodegenerative disorder.

14. The method of claim 1, wherein step (b) comprises culturing the cells produced in step (a) in a second medium comprising 50 ng/ml BMP4.

15. The method of claim 1, wherein step (b) comprises culturing the cells produced in step (a) in a second medium comprising 3 ng/ml to 13 ng/ml BMP4.

16. The method of claim 1, wherein the mammalian stem cells are grown in HUESM medium.

17. The method of claim 1, wherein the pluripotent stem cells are RUES1, RUES2, or RUES 3.

* * * * *

SEQUENCE LISTING

<160> NUMBER OF SEQ ID NOS: 44

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
actcgggttt gacctacagc 20

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
ggtactgaag catcgcacct 20

<210> SEQ ID NO 3
<211> LENGTH: 24
<212> TYPE: DNA
<213> ORGANISM: Artificial Sequence
<220> FEATURE:
<223> OTHER INFORMATION: primer

<400> SEQUENCE: 3
caagctcctg aagcagaaga ggat 24

<210> SEQ ID NO 4
<211> LENGTH: 24
<212> TYPE: DNA
<213> ORGANISM: Artificial Sequence
<220> FEATURE:
<223> OTHER INFORMATION: primer

<400> SEQUENCE: 4
ctcactcggt tctcgatact ggtt 24

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
tcaccatggc aaataacctg 20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
cagcatgcag gagtatgagg 20

<210> SEQ ID NO 7
<211> LENGTH: 23
<212> TYPE: DNA
<213> ORGANISM: Artificial Sequence

```
<220> FEATURE:
<223> OTHER INFORMATION: primer

<400> SEQUENCE: 7

gctggctatt tggaatttaa agg                                              23


<210> SEQ ID NO 8
<211> LENGTH: 19
<212> TYPE: DNA
<213> ORGANISM: Artificial Sequence
<220> FEATURE:
<223> OTHER INFORMATION: primer

<400> SEQUENCE: 8

gggtttggag cagtggaac                                                   19


<210> SEQ ID NO 9
<211> LENGTH: 19
<212> TYPE: DNA
<213> ORGANISM: Artificial Sequence
<220> FEATURE:
<223> OTHER INFORMATION: primer

<400> SEQUENCE: 9

ttacggcagg aaaacacgg                                                   19


<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10

tgccaggcac agaagttaag                                                  20


<210> SEQ ID NO 11
<211> LENGTH: 21
<212> TYPE: DNA
<213> ORGANISM: Artificial Sequence
<220> FEATURE:
<223> OTHER INFORMATION: primer

<400> SEQUENCE: 11

agaagaacgg caagtacgag a                                                21


<210> SEQ ID NO 12
<211> LENGTH: 21
<212> TYPE: DNA
<213> ORGANISM: Artificial Sequence
<220> FEATURE:
<223> OTHER INFORMATION: primer

<400> SEQUENCE: 12

tgttgaggga cagattgtgg c                                                21


<210> SEQ ID NO 13
<211> LENGTH: 21
<212> TYPE: DNA
<213> ORGANISM: Artificial Sequence
<220> FEATURE:
<223> OTHER INFORMATION: primer

<400> SEQUENCE: 13

cctttgtctg tgatcagtgc g                                                21
```

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
cagtgccagt atgggtctgc 20

<210> SEQ ID NO 15
<211> LENGTH: 22
<212> TYPE: DNA
<213> ORGANISM: Artificial Sequence
<220> FEATURE:
<223> OTHER INFORMATION: primer

<400> SEQUENCE: 15
actgggtagg attcgctttt cg 22

<210> SEQ ID NO 16
<211> LENGTH: 21
<212> TYPE: DNA
<213> ORGANISM: Artificial Sequence
<220> FEATURE:
<223> OTHER INFORMATION: primer

<400> SEQUENCE: 16
acacctcact tctcgcaatg g 21

<210> SEQ ID NO 17
<211> LENGTH: 21
<212> TYPE: DNA
<213> ORGANISM: Artificial Sequence
<220> FEATURE:
<223> OTHER INFORMATION: primer

<400> SEQUENCE: 17
aatccttcgg ttacaagcgg t 21

<210> SEQ ID NO 18
<211> LENGTH: 22
<212> TYPE: DNA
<213> ORGANISM: Artificial Sequence
<220> FEATURE:
<223> OTHER INFORMATION: primer

<400> SEQUENCE: 18
actgtgattg ttagcaaggc ac 22

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
gccatcctct ccagaatgaa 20

<210> SEQ ID NO 20
<211> LENGTH: 19
<212> TYPE: DNA
<213> ORGANISM: Artificial Sequence
<220> FEATURE:
<223> OTHER INFORMATION: primer

<400> SEQUENCE: 20
gcaggagaag cacatcagc 19

<210> SEQ ID NO 21
<211> LENGTH: 19
<212> TYPE: DNA
<213> ORGANISM: Artificial Sequence
<220> FEATURE:
<223> OTHER INFORMATION: primer

<400> SEQUENCE: 21
cagcagcggg agagaagtc 19

<210> SEQ ID NO 22
<211> LENGTH: 21
<212> TYPE: DNA
<213> ORGANISM: Artificial Sequence
<220> FEATURE:
<223> OTHER INFORMATION: primer

<400> SEQUENCE: 22
ccagtagagc cagtgaatcc t 21

<210> SEQ ID NO 23
<211> LENGTH: 23
<212> TYPE: DNA
<213> ORGANISM: Artificial Sequence
<220> FEATURE:
<223> OTHER INFORMATION: primer

<400> SEQUENCE: 23
gtgtgtcaac ctgtctatca agg 23

<210> SEQ ID NO 24
<211> LENGTH: 22
<212> TYPE: DNA
<213> ORGANISM: Artificial Sequence
<220> FEATURE:
<223> OTHER INFORMATION: primer

<400> SEQUENCE: 24
catggcatcg tagaagtgga ag 22

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
cgcaccatct catgccatgt 20

<210> SEQ ID NO 26
<211> LENGTH: 19
<212> TYPE: DNA
<213> ORGANISM: Artificial Sequence
<220> FEATURE:
<223> OTHER INFORMATION: primer

<400> SEQUENCE: 26
cgggcggtca ctatcttgt 19

<210> SEQ ID NO 27

<211> LENGTH: 20
<212> TYPE: DNA
<213> ORGANISM: Artificial Sequence
<220> FEATURE:
<223> OTHER INFORMATION: primer

<400> SEQUENCE: 27
ggggcttatc cgcacttacc 20

<210> SEQ ID NO 28
<211> LENGTH: 21
<212> TYPE: DNA
<213> ORGANISM: Artificial Sequence
<220> FEATURE:
<223> OTHER INFORMATION: primer

<400> SEQUENCE: 28
tggcctgata ctcggtgaac a 21

<210> SEQ ID NO 29
<211> LENGTH: 19
<212> TYPE: DNA
<213> ORGANISM: Artificial Sequence
<220> FEATURE:
<223> OTHER INFORMATION: primer

<400> SEQUENCE: 29
cagcagcggg agagaagtc 19

<210> SEQ ID NO 30
<211> LENGTH: 21
<212> TYPE: DNA
<213> ORGANISM: Artificial Sequence
<220> FEATURE:
<223> OTHER INFORMATION: primer

<400> SEQUENCE: 30
ccagtagagc cagtgaatcc t 21

<210> SEQ ID NO 31
<211> LENGTH: 21
<212> TYPE: DNA
<213> ORGANISM: Artificial Sequence
<220> FEATURE:
<223> OTHER INFORMATION: primer

<400> SEQUENCE: 31
tccgacttca atgccatcga c 21

<210> SEQ ID NO 32
<211> LENGTH: 21
<212> TYPE: DNA
<213> ORGANISM: Artificial Sequence
<220> FEATURE:
<223> OTHER INFORMATION: primer

<400> SEQUENCE: 32
tacacgaacg ctaggacaga g 21

<210> SEQ ID NO 33
<211> LENGTH: 20
<212> TYPE: DNA
<213> ORGANISM: Artificial Sequence
<220> FEATURE:
<223> OTHER INFORMATION: primer

<400> SEQUENCE: 33
gcttctgaca gacgccaact 20

<210> SEQ ID NO 34
<211> LENGTH: 22
<212> TYPE: DNA
<213> ORGANISM: Artificial Sequence
<220> FEATURE:
<223> OTHER INFORMATION: primer

<400> SEQUENCE: 34
caccgatgat aaacatctcg gg 22

<210> SEQ ID NO 35
<211> LENGTH: 22
<212> TYPE: DNA
<213> ORGANISM: Artificial Sequence
<220> FEATURE:
<223> OTHER INFORMATION: primer

<400> SEQUENCE: 35
tgtgcaacat gctcagatta ca 22

<210> SEQ ID NO 36
<211> LENGTH: 22
<212> TYPE: DNA
<213> ORGANISM: Artificial Sequence
<220> FEATURE:
<223> OTHER INFORMATION: primer

<400> SEQUENCE: 36
tgcttcatgc caattctttc ca 22

<210> SEQ ID NO 37
<211> LENGTH: 22
<212> TYPE: DNA
<213> ORGANISM: Artificial Sequence
<220> FEATURE:
<223> OTHER INFORMATION: primer

<400> SEQUENCE: 37
tgtaccgact gagagttctt ga 22

<210> SEQ ID NO 38
<211> LENGTH: 23
<212> TYPE: DNA
<213> ORGANISM: Artificial Sequence
<220> FEATURE:
<223> OTHER INFORMATION: primer

<400> SEQUENCE: 38
acagagcgag tgaaaatgtg tat 23

<210> SEQ ID NO 39
<211> LENGTH: 21
<212> TYPE: DNA
<213> ORGANISM: Artificial Sequence
<220> FEATURE:
<223> OTHER INFORMATION: primer

<400> SEQUENCE: 39
gcgcccaaca ccttctatgt a 21

<210> SEQ ID NO 40
<211> LENGTH: 21
<212> TYPE: DNA

-continued

```
<213> ORGANISM: Artificial Sequence
<220> FEATURE:
<223> OTHER INFORMATION: primer

<400> SEQUENCE: 40

ccaggaagcc aacgaacatc a                                          21


<210> SEQ ID NO 41
<211> LENGTH: 21
<212> TYPE: DNA
<213> ORGANISM: Artificial Sequence
<220> FEATURE:
<223> OTHER INFORMATION: primer

<400> SEQUENCE: 41

tgcagtgctg gtaatccgaa t                                          21


<210> SEQ ID NO 42
<211> LENGTH: 23
<212> TYPE: DNA
<213> ORGANISM: Artificial Sequence
<220> FEATURE:
<223> OTHER INFORMATION: primer

<400> SEQUENCE: 42

aaccaatcgc ttcaaacatt tcc                                        23


<210> SEQ ID NO 43
<211> LENGTH: 20
<212> TYPE: DNA
<213> ORGANISM: Artificial Sequence
<220> FEATURE:
<223> OTHER INFORMATION: primer

<400> SEQUENCE: 43

gaaatcttgg gcttgatgga                                            20


<210> SEQ ID NO 44
<211> LENGTH: 20
<212> TYPE: DNA
<213> ORGANISM: Artificial Sequence
<220> FEATURE:
<223> OTHER INFORMATION: primer

<400> SEQUENCE: 44

aggagttgct gatggtgagg                                            20
```